US012690924B2

(12) United States Patent
Ishrak et al.

(10) Patent No.: US 12,690,924 B2
(45) Date of Patent: Jul. 28, 2026

(54) ULTRASOUND IMAGE-BASED GUIDANCE OF MEDICAL INSTRUMENTS OR DEVICES

(71) Applicant: Medtronic, Inc., Minneapolis, MN (US)

(72) Inventors: Syed Omar Ishrak, Laguna Beach, CA (US); Sarah E. Ahlberg, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 398 days.

(21) Appl. No.: 18/054,840

(22) Filed: Nov. 11, 2022

(65) Prior Publication Data

US 2023/0139348 A1    May 4, 2023

Related U.S. Application Data

(63) Continuation of application No. 16/895,564, filed on Jun. 8, 2020, now abandoned.

(Continued)

(51) Int. Cl.
  *A61B 8/08*     (2006.01)
  *A61B 5/349*    (2021.01)
  (Continued)

(52) U.S. Cl.
  CPC .............. *A61B 34/20* (2016.02); *A61B 5/349* (2021.01); *A61B 8/0841* (2013.01);
  (Continued)

(58) Field of Classification Search
  CPC .. A61B 2018/00577; A61B 2034/2051; A61B 2034/2063; A61B 2034/2065;
  (Continued)

(56) References Cited

U.S. PATENT DOCUMENTS 5,131,397 A    7/1992  Crowley
5,311,095 A    5/1994  Smith et al.
           (Continued)

FOREIGN PATENT DOCUMENTS

EP          0844581 B1     7/2007
JP       2004290393 A      10/2004
           (Continued)

OTHER PUBLICATIONS

Guan, SY., Wang, TM., Meng, C. et al. A Review of Point Feature Based Medical Image Registration. Chin. J. Mech. Eng. 31, 76 ( 2018). https://doi.org/1 0.1186/s 1 0033-018-0275-9; also available at https://cjme.springeropen.com/track/pdf/1 0.1186/s1 0033-018-0275-9.pdf (Year: 2018).

(Continued)

*Primary Examiner* — Keith M Raymond
*Assistant Examiner* — Milton Truong
(74) *Attorney, Agent, or Firm* — Shumaker & Sieffert, P.A.

(57)           ABSTRACT

In an example, a system includes an ultrasound sensor configured to transmit ultrasound energy and receive ultrasound energy reflected in a region of a patient and one or more processors configured to generate a reference ultrasound image of the region of the patient based on a portion of the ultrasound energy that was received by the ultrasound sensor prior to a medical instrument or medical device causing obstruction in the received ultrasound energy, generate a live ultrasound image based on a current portion of the received ultrasound energy obtained by the ultrasound sensor, register the reference ultrasound image and the live ultrasound image, and control a display device to display the reference ultrasound image with at least a portion of the live ultrasound image.

66 Claims, 35 Drawing Sheets

Related U.S. Application Data

(60) Provisional application No. 62/910,867, filed on Oct. 4, 2019, provisional application No. 62/863,173, filed on Jun. 18, 2019.

(51) Int. Cl.

| | |
|---|---|
| *A61B 8/00* | (2006.01) |
| *A61B 34/20* | (2016.01) |
| *A61F 2/24* | (2006.01) |
| *A61B 18/00* | (2006.01) |
| *A61F 2/95* | (2013.01) |
| *A61M 60/148* | (2021.01) |
| *A61N 1/362* | (2006.01) |

(52) U.S. Cl.
CPC ............ *A61B 8/0883* (2013.01); *A61B 8/463* (2013.01); *A61F 2/2427* (2013.01); *A61B 8/4245* (2013.01); *A61B 8/5284* (2013.01); *A61B 2018/00351* (2013.01); *A61B 2018/00577* (2013.01); *A61B 2034/2051* (2016.02); *A61B 2034/2063* (2016.02); *A61B 2034/2065* (2016.02); *A61F 2/95* (2013.01); *A61M 60/148* (2021.01); *A61N 1/362* (2013.01)

(58) Field of Classification Search
CPC ....... A61B 34/20; A61B 5/349; A61B 8/0841; A61B 8/0883; A61B 8/4245; A61B 8/463; A61B 8/5246; A61B 8/5284; A61B 8/543
See application file for complete search history.

(56) References Cited

U.S. PATENT DOCUMENTS

| | | | |
|---|---|---|---|
| 5,322,068 A | | 6/1994 | Thiele et al. |
| 5,740,804 A | | 4/1998 | Cerofolini |
| 6,019,724 A | | 2/2000 | Gronningsaeter et al. |
| 6,162,175 A | * | 12/2000 | Marian, Jr. .............. A61B 8/12 |
| | | | 600/447 |
| 6,443,896 B1 | | 9/2002 | Detmer |
| 6,488,629 B1 | | 12/2002 | Saetre |
| 6,524,247 B2 | | 2/2003 | Zhao et al. |
| 6,527,720 B1 | | 3/2003 | Ustuner et al. |
| 6,623,432 B2 | | 9/2003 | Powers et al. |
| 6,645,150 B2 | | 11/2003 | Angelsen et al. |
| 6,656,120 B2 | | 12/2003 | Lee et al. |
| 6,682,488 B2 | | 1/2004 | Abend |
| 6,968,224 B2 | | 11/2005 | Kessman et al. |
| 6,979,292 B2 | | 12/2005 | Kanayama et al. |
| 7,529,393 B2 | | 5/2009 | Peszynski et al. |
| 7,604,601 B2 | | 10/2009 | Altmann et al. |
| 7,758,509 B2 | | 7/2010 | Angelsen et al. |
| 7,921,717 B2 | | 4/2011 | Jackson et al. |
| 8,206,305 B2 | | 6/2012 | Garbini et al. |
| 8,401,616 B2 | | 3/2013 | Verard et al. |
| 8,475,384 B2 | | 7/2013 | Hart et al. |
| 8,556,815 B2 | | 10/2013 | Pelissier et al. |
| 8,801,617 B2 | | 8/2014 | McGee |
| 8,840,557 B2 | | 9/2014 | Casciaro et al. |
| 8,858,443 B2 | | 10/2014 | Zhang |
| 9,226,729 B2 | | 1/2016 | Tashiro et al. |
| 9,326,749 B2 | | 5/2016 | Okamura et al. |
| 9,471,981 B2 | | 10/2016 | Arai et al. |
| 9,524,551 B2 | | 12/2016 | Hashimoto et al. |
| 9,561,017 B2 | | 2/2017 | Burcher |
| 9,675,318 B2 | | 6/2017 | Tashiro et al. |
| 9,713,460 B2 | | 7/2017 | Shin et al. |
| 9,770,331 B2 | | 9/2017 | Gifford, III et al. |
| 10,102,452 B2 | | 10/2018 | Pickie et al. |
| 10,143,398 B2 | | 12/2018 | Altmann et al. |
| 10,194,888 B2 | | 2/2019 | Henderson et al. |
| 10,299,758 B2 | | 5/2019 | Katsuyama |

| | | | |
|---|---|---|---|
| 10,380,399 B2 | | 8/2019 | Call et al. |
| 10,548,666 B2 | | 2/2020 | Girotto et al. |
| 2006/0229594 A1 | | 10/2006 | Francischelli et al. |
| 2006/0241451 A1 | | 10/2006 | Nakaya et al. |
| 2007/0106147 A1 | | 5/2007 | Altmann et al. |
| 2007/0276234 A1 | | 11/2007 | Shahidi |
| 2008/0025145 A1 | | 1/2008 | Peszynski et al. |
| 2008/0249409 A1 | * | 10/2008 | Fraser ..................... A61B 8/14 |
| | | | 600/439 |
| 2008/0267499 A1 | | 10/2008 | Deischinger et al. |
| 2008/0300478 A1 | | 12/2008 | Zuhars et al. |
| 2010/0056917 A1 | | 3/2010 | Karasawa |
| 2010/0160783 A1 | | 6/2010 | Halmann et al. |
| 2010/0240992 A1 | | 9/2010 | Hao |
| 2011/0201936 A1 | | 8/2011 | Miyajima |
| 2011/0249878 A1 | | 10/2011 | Pagoulatos et al. |
| 2012/0172708 A1 | * | 7/2012 | Anand ................... G16H 50/30 |
| | | | 600/411 |
| 2013/0072786 A1 | | 3/2013 | Keogh et al. |
| 2014/0155738 A1 | * | 6/2014 | Cheny ................. A61B 8/5246 |
| | | | 600/424 |
| 2014/0221823 A1 | | 8/2014 | Keogh et al. |
| 2016/0030008 A1 | | 2/2016 | Gerard |
| 2016/0174873 A1 | | 6/2016 | Greenburg et al. |
| 2016/0180521 A1 | | 6/2016 | Mountney et al. |
| 2016/0206289 A1 | | 7/2016 | Yamamoto et al. |
| 2016/0287214 A1 | | 10/2016 | Ralovich et al. |
| 2016/0302759 A1 | | 10/2016 | Shi et al. |
| 2016/0317118 A1 | | 11/2016 | Parthasarathy et al. |
| 2016/0354057 A1 | | 12/2016 | Hansen et al. |
| 2017/0055950 A1 | | 3/2017 | Matsuda |
| 2017/0135760 A1 | | 5/2017 | Girotto et al. |
| 2017/0245835 A1 | | 8/2017 | Okazaki et al. |
| 2017/0325785 A1 | | 11/2017 | Lieblich et al. |
| 2017/0366756 A1 | | 12/2017 | Robert et al. |
| 2018/0085096 A1 | * | 3/2018 | Brandl .................... A61B 8/469 |
| 2018/0125448 A1 | | 5/2018 | Karadayi |
| 2018/0256131 A1 | | 9/2018 | Bracken et al. |
| 2019/0000558 A1 | * | 1/2019 | Abraham ............. A61B 8/0883 |
| 2019/0021699 A1 | | 1/2019 | Bracken et al. |
| 2019/0090951 A1 | | 3/2019 | Camus et al. |
| 2019/0201110 A1 | * | 7/2019 | Kuenen ..................... G06T 5/50 |
| 2019/0209124 A1 | * | 7/2019 | Taniguchi ............ A61B 8/4461 |
| 2019/0307516 A1 | | 10/2019 | Schotzko et al. |
| 2019/0307518 A1 | | 10/2019 | Schotzko et al. |
| 2020/0196983 A1 | | 6/2020 | Kruecker |
| 2020/0222119 A1 | | 7/2020 | Kruecker et al. |
| 2020/0268347 A1 | * | 8/2020 | Kolen .................... A61B 5/066 |
| 2021/0353362 A1 | * | 11/2021 | Vaidya ................. A61B 8/4254 |

FOREIGN PATENT DOCUMENTS

| | | | |
|---|---|---|---|
| JP | 2006346176 A | 12/2006 | |
| JP | 2012245092 A | 12/2012 | |
| JP | 5273945 B2 | 8/2013 | |
| JP | 5820129 B2 | 11/2015 | |
| WO | 2012051308 A2 | 4/2012 | |
| WO | 2018101985 A1 | 6/2018 | |
| WO | 2018122661 A1 | 7/2018 | |
| WO | 2019134959 A1 | 7/2019 | |

OTHER PUBLICATIONS

International Preliminary Report on Patentability from International Application No. PCT/US2020/036819, dated Dec. 30, 2021, 10 pp.
International Search Report and Written Opinion of International Application No. PCT/US2020/036819, mailed Sep. 24, 2020, 19 pp.
Peters et al., "Ultrasound Image Guidance for Cardiac Interventions," Medical Imaging 2011: Ultrasonic Imaging, Tomography, and Therapy, Proc. of SPIE, vol. 7966, No. 1, Mar. 3, 2011, 12 pp.
Prosecution History from U.S. Appl. No. 16/895,564, dated Feb. 10, 2022 through Jul. 20, 2022 pp. 78.
Ren et al., "Varying Ultrasound Power Level to Distinguish Surgical Instruments and Tissue," Med Biol Eng Comput, vol. 56, No. 3, Mar. 2018, pp. 453-467.
Shen et al., "Deep Learning in Medical Image Analysis," Annual review of biomedical engineering. Jun. 2017;19; pp. 221-248.

(56) References Cited

OTHER PUBLICATIONS

Stoll, "Ultrasound Fusion Imaging," Perspectives in Medicine, vol. 1, Sep. 2012, 2 pp.

Trots et al., "Multi-Element Synthetic Transmit Aperture in Medical Ultrasound Imaging," Archives of Acoustic, vol. 35, No. 4, Nov. 19, 2010, pp. 687-699.

Vignon et al., "The Stripe Artifact in Transcranial Ultrasound Imaging," Journal of Ultrasound Medicine, vol. 29, No. 12, Dec. 2010, pp. 1779-1786.

Wachinger et al., "Ultrasound Mosaicing and Motion Modeling, Applications in Medical Image Registration," The Technical University of Munich, Mar. 3, 2011, 263 pp.

* cited by examiner

702

640

642
RECEIVE EVENT DATA

644
DETERMINE CURRENT EVENT FROM EVENT DATA

646
RETRIEVE EVENT-MATCHED REFERENCE IMAGE

648
PRESENT EVENT-MATCHED REFERENCE IMAGE WITH LIVE IMAGE

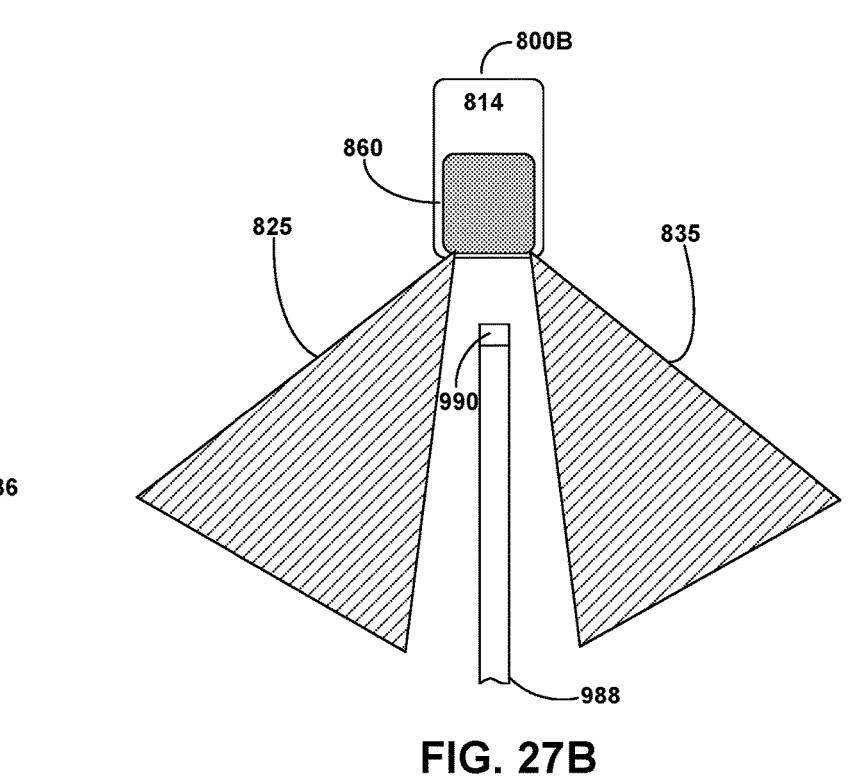
FIG. 27A
FIG. 27B
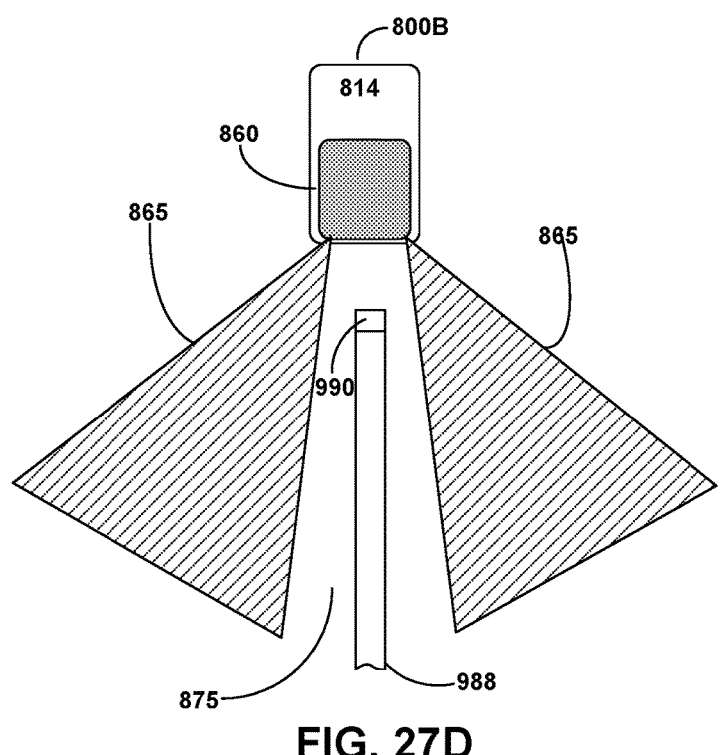
FIG. 27C
FIG. 27D

ULTRASOUND IMAGE-BASED GUIDANCE OF MEDICAL INSTRUMENTS OR DEVICES

This application is a continuation of U.S. patent application Ser. No. 16/895,564, entitled ULTRASOUND IMAGE-BASED GUIDANCE OF MEDICAL INSTRUMENTS OR DEVICES, filed Jun. 8, 2020, and claims the benefit of U.S. Provisional Application No. 62/910,867, entitled ULTRASOUND IMAGE-BASED GUIDANCE OF MEDICAL INSTRUMENTS OR DEVICES, filed Oct. 4, 2019, and of U.S. Provisional Application No. 62/863,173, entitled ULTRASOUND IMAGE-BASED GUIDANCE OF MEDICAL INSTRUMENTS AND/OR DEVICES, filed Jun. 18, 2019, the entirety of all of which are hereby incorporated by reference.

TECHNICAL FIELD

This disclosure relates to the use of imaging for medical instrument or medical device guidance within a patient.

BACKGROUND

Echocardiography and other types of imaging systems may be difficult to use and interpret, especially for implanters (e.g., cardiac surgeons and interventional cardiologists) of various types of medical devices delivered by transcatheter or other medical instruments using minimally-invasive techniques (e.g., coronary stents, heart valves, ablation devices, cardiac leads) or implanters of mechanical circulatory support devices (e.g., Left Ventricle Assist Device (LVAD)). Currently, many surgeons do not use echocardiography during these types of procedures because of inherent shortcomings of available imaging systems (e.g., difficult to interpret, poor image quality, etc.). Further, clinicians are increasingly utilizing more minimally invasive techniques for implanting cardiac devices in contrast to open heart surgery and sternotomies. These minimally invasive techniques require improved imaging systems as the clinician does not have a line-of-sight view of the patient's heart or other anatomy of interest during the implantation procedure.

Image-guided medical and surgical procedures utilize patient images obtained prior to or during a medical procedure to guide a clinician performing the procedure. Recent advances in imaging technology, especially in imaging technologies that produce highly-detailed two, three, and four-dimensional images, such as computed tomography (CT), magnetic resonance imaging (MRI), isocentric C-arm fluoroscopic imaging, positron emission tomography (PET), and ultrasound imaging (US), have heightened the interest in image-guided medical procedures.

At present, cardiac catheterization procedures are typically performed with the aid of fluoroscopic images. Two-dimensional fluoroscopic images taken intra-procedurally allow a physician to visualize the location of a catheter being advanced through cardiovascular structures. Use of such fluoroscopic imaging throughout a procedure, however, exposes both the patient and the operating room staff to radiation and exposes the patient to contrast agents. As a result, the number of fluoroscopic images taken during a procedure is preferably limited to reduce the radiation exposure to the patient and staff. Additionally, since fluoroscopy does not visualize cardiac tissue very well, it is relied upon mostly for visualizing blood with contrast dye injected into it. Therefore, fluoroscopy is not the imaging modality of choice for procedures that require a detailed understanding of the location and motion of cardiac tissue.

Other types of procedures include the use of electro-physiologic mapping catheters to map the heart based on measured electrical potentials. Such mapping catheters are useful in identifying an area of tissue that is either conducting normally or abnormally; however, some mapping catheters may not aid in guiding a medical instrument or medical device to a targeted tissue area for medical treatment.

SUMMARY

In general, this disclosure is directed to various techniques for generating images for image-based guidance of medical instruments or medical devices through a region of a patient's body. When using an ultrasound imaging system for navigation in a region of a patient's body, visual obstructions such as image shadowing or other artifacts may be caused due to reflections of ultrasound energy by a medical instrument or medical device, such as a delivery catheter, a surgical instrument, or an implantable medical device being delivered or implanted in the region.

As used herein, the term "medical instrument or medical device" should be understood to mean "medical instrument and/or medical device" as either a medical instrument or a medical device or both may cause visual obstructions in ultrasound images. Also, as used herein, the term "obstruction" refers to obstruction in reflected ultrasound energy that would cause a visual obstruction if displayed as an ultrasound image, or a visual obstruction in an ultrasound image.

These visual obstructions may obstruct one or more portions of anatomy of interest within the region of the patient imaged by the ultrasound imaging system. For example, during guidance for delivery of a medical instrument or medical device, the medical instrument or medical device or both may reflect ultrasound energy and prevent the ultrasound energy from reaching and returning from anatomy of interest in the region, producing a shadowing effect that may obscure the anatomy of interest in a resultant ultrasound image. When a medical device, such as an implantable medical device, is being implanted, it may be important to locate the medical device in a particular anatomical location within a patient. If visual obstructions are obstructing the anatomy of interest, it may be difficult for a clinician to locate the medical device in the desired location.

This disclosure describes various devices, systems and methods that may be effective in alleviating problems associated with visual obstruction of anatomy of interest in ultrasound images due the presence of medical instruments or medical devices in a region of the patient being imaged. In various examples, the disclosure describes techniques that may improve the ability to effectively use ultrasound imaging for guidance of medical instruments or medical devices within a patient. A device or system, in accordance with various examples of this disclosure, may include one or more imaging systems and a controller configured to control an ultrasound imager and utilize data from the one or more imaging systems to control a display device to present ultrasound imagery, or imagery or information generated using ultrasound images, to provide guidance information to a clinician that is performing a medical procedure involving a medical instrument for delivery or implantation of a medical device within a region of patient.

The device or system may include the use of reference images of a region of a patient. The device or system may include an ultrasound probe with a split-aperture. The device or system may include an ultrasound probe with a wide-angle mode or a toroidal mode. The device or system may also include automation techniques for ultrasound imaging.

In one example, the disclosure describes a system comprising an ultrasound sensor configured to transmit ultrasound energy and receive ultrasound energy reflected in a region of a patient and one or more processors configured to: generate a plurality of reference ultrasound images of the region of the patient based on a portion of the ultrasound energy that was received by the ultrasound sensor prior to a medical instrument or medical device causing obstruction in the received ultrasound energy; generate a live ultrasound image based on a current portion of the received ultrasound energy obtained by the ultrasound sensor; select one of the plurality of reference ultrasound images based on at least one of correspondence with event data received by the one or more processors or a spatial orientation of the live ultrasound image; register the reference ultrasound image and the live ultrasound image; and control a display device to display the selected reference ultrasound image with at least a portion of the live ultrasound image.

In another example, the disclosure describes a method comprising transmitting ultrasound energy, receiving ultrasound energy reflected in a region of a patient, generating a plurality of reference ultrasound images of the region of the patient based on a portion of the received ultrasound energy that was received prior to a medical instrument or medical device causing obstruction in the received ultrasound energy, generating a live ultrasound image based on a current portion of the received ultrasound energy, selecting one of the plurality of reference ultrasound images based on at least one of correspondence with event data received by the one or more processors or a spatial orientation of the live ultrasound image, registering the reference ultrasound image and the live ultrasound image, and controlling a display device to display the selected reference ultrasound image with at least a portion of the live ultrasound image.

In yet another example, the disclosure describes a non-transitory computer readable medium comprising instructions, which when executed, cause one or more processors to generate a plurality of reference ultrasound images of a region of a patient based on a portion of received ultrasound energy that was received prior to a medical instrument or medical device causing obstruction in the received ultrasound energy, generate a live ultrasound image based on a current portion of the received ultrasound energy, select one of the plurality of reference ultrasound images based on at least one of correspondence with event data received by the one or more processors or a spatial orientation of the live ultrasound image, register the reference ultrasound image and the live ultrasound image, and control a display device to display the selected reference ultrasound image with at least a portion of the live ultrasound image.

These and other aspects of the present disclosure will be apparent from the detailed description below. In no event, however, should the above summaries be construed as limitations on the claimed subject matter, which subject matter is defined solely by the attached claims.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

FIGS. 27A, 27B, 27C, and 27D are schematic views of different example modes of operation of an ultrasound imaging system to produce ultrasound images when a medical instrument or medical device is causing obstruction of reflected ultrasound energy in a field of view.

DETAILED DESCRIPTION

Ultrasound imaging is a useful tool for diagnostic imaging. Echocardiography, for example, is widely used as a diagnostic imaging tool to assess cardiac structure and flow dynamics within the heart. Ultrasound imaging may also be useful as a tool to assist with guidance or navigation of medical instruments or medical devices within a patient's body. For example, echocardiography may be used to assist with navigation for minimally invasive cardiac procedures, such as cardiac valve replacement or repair, providing enhanced visualization of cardiac tissue with echo as compared to fluoroscopy.

In contrast to fluoroscopy, ultrasound imaging does not present radiation exposure concerns. When using ultrasound imaging for guidance, however, medical instruments or medical devices in the field of view may cause visual obstructions such as image shadowing or other artifacts, due to reflection or obstruction of ultrasound waves by the medical instrument or the medical device being guided. In the case of mitral valve repair or replacement, as one example, a distal tip of a catheter used for transcatheter delivery may reflect ultrasound energy, causing shadowing or other artifacts that may obscure the catheter and anatomy proximal of the distal tip.

Figure 1:
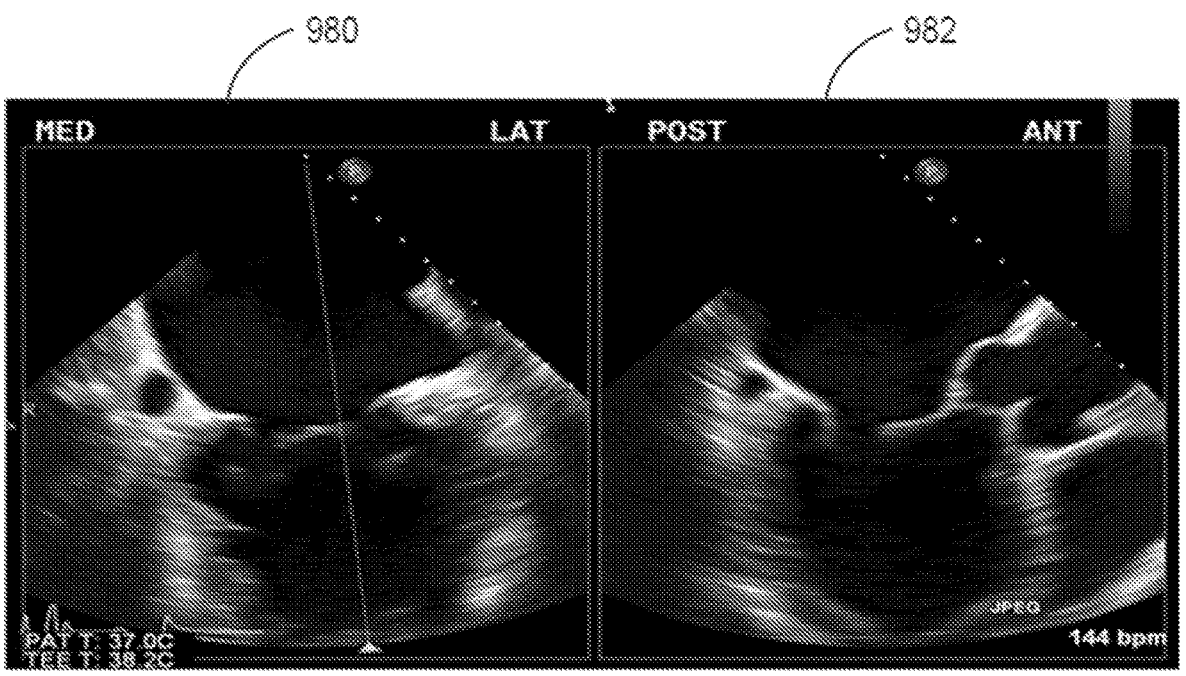
FIG. 1 is a schematic view of an example of a display presenting an ultrasound image.

FIG. 1 is a schematic view of an example of a display of a medial-lateral (MED-LAT) view 980 and posterior-anterior (POST-ANT) view 982 of ultrasound imagery showing anatomy within a heart. In particular, FIG. 1 depicts an example of a left ventricle and left atrium showing the position of the mitral valve. FIG. 1 shows good visualization of cardiac tissue with echocardiography, including visualization of the left atrium, left ventricle mitral valve, and aorta. The imagery shown in FIG. 1 may be useful for guidance and navigation of medical instruments or medical devices within the heart, such as, e.g., guidance for transcatheter mitral valve repair or mitral valve replacement procedures. In the example of FIG. 1, a device such as a catheter for a transcatheter mitral valve repair or replacement procedure is not present. Therefore, FIG. 1 does not show any significant amount of visual obstruction, such as shadowing, that may be caused by a medical instrument or medical device within the field of view of the ultrasound imaging modality in the anatomical region of interest.

Figure 2:
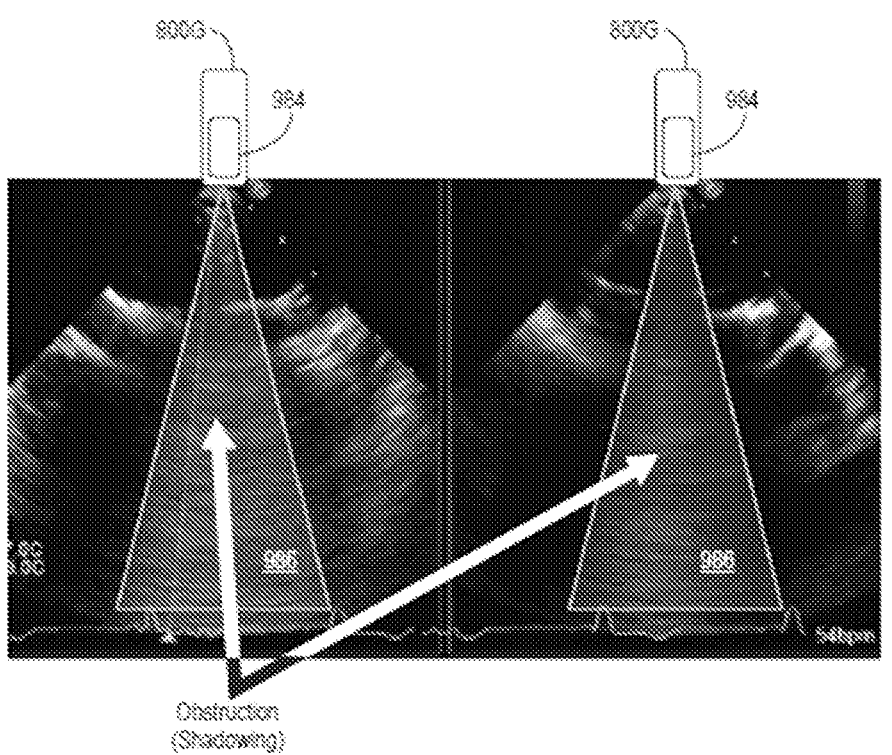
FIG. 2 is a schematic view of an example of an ultrasound image produced with visual obstruction caused by presence of a medical instrument or medical device within the field of view.

FIG. 2 is a schematic view of an example ultrasound imaging system that includes an ultrasound probe 800G and an ultrasound transducer array 984 configured to transmit and receive ultrasound energy. The ultrasound imaging system of FIG. 2 may further include ultrasound workstation 150, not shown in FIG. 2, but shown in FIGS. 3A and 3B. Ultrasound probe 800G may be part of or all of ultrasound imager 140 or 142 of FIGS. 3A and 3B, respectively. In the example of FIG. 2, the ultrasound imaging system may be considered to be operating in a regular, focused imaging mode that would focus on a portion of the cardiac anatomy that would include medical instruments or medical devices in the field of view. In this regular imaging mode, ultrasound transducer array 984 would receive reflected ultrasound energy in a field of view that would include a visually obstructed region. Parameters for the regular imaging mode, such as amplitude, frequency, pulse width, power or phase delay, may vary based on a particular use case. For transesophageal echocardiography to image a mitral valve, for example, the frequency may be in the range of 6-10 MHz.

For example, the field of view of ultrasound transducer array 984 would include visual obstruction, such as shadowing, due to the presence of the medical instruments or medical devices in the field of view. FIG. 2 shows shadowing within portion 986 of the field of view. This shadowing makes it difficult for a clinician to use the imagery of FIG. 2 for guidance and navigation of a medical instrument or medical device within the region of the patient that is imaged. In this case, the shadowing is produced due to reflection from the medical instrument or medical device that actually requires echo-based navigation guidance. When a medical device, such as an implantable medical device, is being implanted, it may be important to locate the medical device in a particular anatomical location within a patient, e.g., relative to a particular anatomy of interest. If visual obstructions are obstructing the anatomy of interest, it may be difficult for a clinician to locate the medical device in the desired location. Therefore, it is desirable to be able to view the anatomy of interest within a region of a patient.

This disclosure describes various examples of techniques, e.g., implemented in devices, systems and methods, that may be configured to alleviate problems associated with visual obstruction of anatomy of interest in ultrasound images due the presence of medical instruments or medical devices in the ultrasound field of view. In some examples, the techniques may use a reference image(s) and overlay, underlay, merge or otherwise present the reference image(s) on the image containing the visual obstruction. In other words, the reference image(s) may be placed on top of, below or may be combined with the live image in an attempt to improve the visibility of the patient's anatomy in a region of interest. The reference image may include generally unobstructed imagery of anatomy of interest, e.g., obtained at a time prior to obstruction. In some examples, the techniques may use ultrasound beamforming methodologies or ultrasound transducer subsets or arrays that may be configured to reduce visual obstruction, such as shadowing, distal to and caused by a medical instrument or medical device in the field of view. Automation and machine learning may also be employed, in some examples, to detect the medical instrument or medical device and adjust the device or system so as to alleviate or mitigate the problems associated with visual obstructions.

Techniques described in this disclosure may be used in imaging and guidance for any of a variety of medical instruments and medical devices including, for purposes of example and without limitation, implantable medical devices, medical implant delivery devices, therapy delivery devices, surgical devices, mechanical circulatory support devices, coronary stent devices, heart valve devices, heart valve repair devices, cardiac ablation devices, cardiac lead devices, drug delivery devices, catheter delivery devices, and endoscopic delivery devices. As one illustration, the techniques may be especially useful in providing ultrasound images to support guidance of transcatheter mitral valve repair or replacement.

In an example, an ultrasound imaging system may generate a reference ultrasound image(s) using reflected ultrasound energy that was received prior to the time that a medical instrument or medical device caused visual obstruction, such as shadowing, in the reflected ultrasound energy obtained for a region of the patient's body. The ultrasound imaging system may control a display device to display the reference ultrasound image, or a portion thereof, with live ultrasound image(s) obtained, e.g., in real time, during guidance of the instrument or device within the region of the patient's body. For example, the ultrasound reference image may be presented on the display device in overlay, in underlay, merge or otherwise present the reference image with a live ultrasound image, e.g., simultaneously, to show the field of view without visual obstruction, such as shadowing, that may otherwise be presented in the live ultrasound imaging data.

In this example, the reference ultrasound image may be obtained before the medical instrument or medical device is guided into the patient's body, or before the medical device or medical instrument is guided into a region of interest within the patient's body, such that the medical instrument or medical device is not in the field of view of the ultrasound transducer array, and is not producing obstruction, at the time the reference ultrasound image is obtained. As an alternative, the reference ultrasound image may be obtained after the medical instrument or medical device has been guided or partially guided into the patient's body, and possibly after the medical instrument or medical device is guided or partially guided into a region of interest within the patient's body, such that the medical instrument or medical device is in the field of view of the ultrasound transducer array, but at a point at which the medical instrument or medical device is not yet producing significant visual obstruction in the ultrasound image. In some cases, this may permit the reference ultrasound image to be obtained closer in time to the live ultrasound image obtained during guidance of the medical instrument or medical device.

In some examples, the ultrasound imaging system may be configured to select the ultrasound reference image from a plurality of reference ultrasound images, based on synchronization with a cardiac event. The cardiac event may be indicated by an ECG signal, e.g., as an ECG component such as P wave, QRS complex or T wave. Alternatively, the cardiac event may be a phase of the cardiac cycle, (e.g., atrial systole, ventricular systole, atrial diastole, or ventricular diastole), which may be derived from the ECG signal or derived from other information such as ultrasound images. The ultrasound reference image alternatively may be selected based on correspondence to a current spatial orientation, such as an orientation of a live ultrasound image, or may be selected based on a combination of both correspondence to a cardiac event and correspondence to a current spatial orientation. In this manner, the reference ultrasound image presented with a live ultrasound image is selected to substantially match the live ultrasound image, e.g., in terms of the current phase of cardiac or other cyclical organ function, or in terms of a spatial orientation of the image, taking into account different degrees of translation, rotation, or perspective of the images. In some examples, the ultrasound imaging system may automatically select the ultrasound reference image.

Alternatively, a series of successive ultrasound reference images may be obtained over the full cycle of a moving anatomical structure, such as the full cardiac cycle of the heart, e.g., as a motion loop of reference images. The reference ultrasound images then may be presented as a series of reference frames, like a motion picture, with live ultrasound images over ensuing cardiac cycles, resetting for replay at the start of each cycle. For example, the motion loop, obtained for a full cardiac cycle, may be started with each cardiac cycle and played for the duration of the cardiac cycle, promoting synchronization with the live ultrasound images. In some examples, an ultrasound imaging system may be configured to apply machine learning techniques to identify substantial correlation between reference ultrasound images and live ultrasound images given different events or spatial orientations. Hence, in some examples, multiple images may be stored and matched to particular orientations and particular events. In some examples, the rate at which the series of reference images is presented like a motion picture may be changed to promote synchronization with the live ultrasound image.

In some examples, multiple reference ultrasound images may be obtained prior to a point at which the medical instrument or medical or device is producing visual obstruction in the ultrasound image. For example, a clinician may prompt an ultrasound imaging system to obtain multiple reference images synchronized with multiple events such as cardiac phases, ECG events or the like, or synchronized with multiple image spatial orientations. The collection of multiple reference images may proceed for a period of time that may be controlled by the clinician or limited by detection of obstruction caused by a medical instrument or medical device in the region of interest.

In one example, an ultrasound transducer array may be configured or controlled to provide a split aperture comprising two or more sections. In this example, an ultrasound transducer array may produce two simultaneous, or substantially simultaneous, ultrasound images on different sides of a medical instrument or medical device such as, e.g., a catheter for transcatheter mitral valve replacement, being guided within the field of view. By providing two or more ultrasound images, e.g., in first and second fields of view, an ultrasound imaging system may, in effect, produce images around (e.g., at the sides) of the medical instrument or medical device that is causing the visual obstruction, providing better visualization of anatomy in the region of interest.

In some examples, the ultrasound transducer array may be controlled, e.g., with beamforming techniques, to produce two separate images with different fields of view, or be constructed with two separate ultrasound transducer sub-arrays with different fields of view. For example, the different fields of view may be on opposite sides of the medical instrument or medical device. In some examples, they may be on the medial and lateral sides, the anterior and posterior sides or both relative to a patient's body. An ultrasound imaging system may process the images to produce a combined ultrasound image with a combined field of view for use in guiding the medical instrument or medical device. Alternatively, the ultrasound imaging system may produce separate ultrasound images showing regions in the different fields of view at different sides of the medical instrument or medical device.

If the images overlap with one another, an ultrasound imaging system may stitch overlapping portions together to maintain image data around the instrument or device. To compensate for reduced resolution that may result from smaller imaging apertures, the ultrasound imaging system may use higher ultrasound imaging frequencies (e.g., harmonics) in the split aperture imaging mode than in other imaging modes. In this manner, in some examples, the use of higher frequency ultrasound energy with smaller imaging apertures may promote image quality. Parameters for the split aperture imaging mode, such as amplitude, frequency, pulse width, power or phase delay, may vary based on a particular use case.

As an alternative to a split aperture, in some examples, other beamforming methods may be applied for other imaging modes to present ultrasound images with other fields of view. In some examples, one other imaging mode may be a wide angle imaging mode wherein the other field of view may be a wide angle field of view. For example, ultrasound energy may be focused so as to form a field of view that is generally trapezoidal in cross-section. In some examples, the field of view may be a generally trapezoidal shape with a curved end distal of the transducer array. These shapes are hereinafter referred to as "generally trapezoidal". Other fields of view with other geometries may also be used, such that the ultrasound imaging system programs the direction of a steered ultrasound beam to avoid a region in which visual obstruction, such as shadowing, is present. In some examples, geometries such as generally trapezoid geometries may provide a wide angle field of view, relative to geometries used in a regular imaging mode. A generally trapezoidal or other similar geometry may, in some examples, provide a reduced imaging depth with enhanced resolution in the near field. Also, a wide angle geometry may, in some examples, more effectively image different fields of view at different sides of the medical instrument or medical device. Parameters for the wide angle imaging mode, such as amplitude, frequency, pulse width, power or phase delay, may vary based on a particular use case.

Other modes with fields of view of other geometries may also be used, such that the ultrasound imaging system programs the direction of a steered ultrasound beam to avoid a region in which visual obstruction, such as shadowing, is present. For example, another imaging mode may be a toroidal imaging mode with a field of view that may be generally toroidal in shape. In this example, the field of view may be 360 degrees around the medical instrument or medical device, but be able to produce an unobstructed image because the medical instrument or medical device is within the cavity in the toroidal field of view. Parameters for the toroidal imaging mode, such as amplitude, frequency, pulse width, power or phase delay, may vary based on a particular use case.

The ultrasound imaging system, in some examples, may be configured to transition between a regular imaging mode and a split aperture, wide angle, or toroidal imaging mode or to display a reference image either manually or automatically. For example, the ultrasound imaging system may select different imaging modes or display the reference image based on user input, e.g., when a user perceives visual obstruction and wishes to change to the split aperture, wide angle or toroidal imaging mode or to display the reference image, or automatically select imaging modes or display the reference image based on whether an obstruction caused by a medical instrument or medical device in the field of view is detected. If such an obstruction is detected, the ultrasound imaging system may automatically change the imaging mode from a first, e.g., regular mode, to a second mode, such as a split aperture, wide angle or toroidal imaging mode, that avoids or reduces effects of visual obstruction on imaging or targets one or more areas in which visual obstruction is not present or is less pronounced or the ultrasound imaging system may begin displaying the reference image.

In some examples, the ultrasound imaging system may be configured to permit a user to manually steer one or more beams of ultrasound energy, e.g., in a regular, single beam mode, a split aperture mode, a wide angle mode, or a toroidal mode, as desired to avoid or reduce the effect of visual obstruction in the field of view. In this case, the ultrasound imaging system may be responsive to user input to steer one or more beams of ultrasound energy and associated fields of view of an ultrasound transducer array or arrays. In other examples, an ultrasound imaging system may configured to automatically steer one or more beams of ultrasound energy in response to, or based on, detection of an obstruction of ultrasound energy in the field of view.

In some examples, for selecting an imaging mode or steering ultrasound energy or beginning to display the reference image, the ultrasound imaging system may detect an obstruction in a variety of ways, such as by analyzing reflected ultrasound energy to identify one or more characteristics of the obstruction or by analyzing image data in one or more ultrasound images produced using the reflected ultrasound energy. In either case, upon detection of an obstruction, the ultrasound imaging system may generate a notification to a user indicating the obstruction. This notification may be visual, audible, tactile, or the like and may be sent to a notification device, such as display device 110, display device 206, ultrasound workstation 150, computing system 100, ultrasound imager 140, ultrasound imager 142 or a speaker (not shown). Alternatively or in addition to providing the notification, the ultrasound imaging system may automatically take action, such as transitioning from a first imaging mode to a different imaging mode or automatically steering or otherwise beamforming ultrasound energy to avoid or reduce obstruction or target areas in which obstruction is not present or less pronounced or beginning to display the reference image.

In various examples, techniques described in this disclosure may be used separately or in any combination. As one example, techniques described in this disclosure for obtaining ultrasound images using ultrasound transducer arrays that are configured or controlled to avoid or reduce effects of visual obstruction caused by the presence of medical instruments or medical devices, e.g., using split aperture mode, wide angle mode, toroid mode, steering or other selected beamforming techniques or geometries, may be used with techniques described in this disclosure that include generation of reference ultrasound images for presentation with live ultrasound images. For example, an ultrasound imaging system may present an image obtained using ultrasound transducer arrays that are configured or controlled to avoid or reduce effects of visual obstruction with a reference ultrasound image obtained prior to a medical instrument or medical device causing visual obstruction, such as shadowing, in the reflected ultrasound energy obtained for a region of the patient's body.

In addition, techniques described in this disclosure for avoiding or reducing effects of visual obstruction caused by the presence of medical instruments or medical devices, e.g., using split aperture mode, wide angle mode, toroidal mode, steering or other selected beamforming techniques or geometries, may be combined with techniques that make use of reference images matched with events such as ECG signals or phases or reference images matched with live image orientation. For example, an ultrasound imaging system may present an image obtained using ultrasound transducer arrays that are configured or controlled to avoid or reduce effects of visual obstruction with a reference ultrasound image selected based on event or orientation matching.

As another example, techniques for using ultrasound transducer arrays that are configured or controlled to avoid or reduce effects of obstruction may be combined with electromagnetic (EM) tracking techniques described in this disclosure in an imaging and guidance system to present ultrasound images with reduced obstruction with imagery or other information indicating position, orientation, or trajectory of a medical instrument or medical device as provided by the EM tracking system and determined by the imaging and guidance system. Likewise, techniques described in this disclosure for generating and presenting ultrasound reference images may be combined with techniques for determining position, orientation, or trajectory of a medical instrument or medical device by EM tracking, such that an imaging and guidance system may display reference ultrasound images, live ultrasound images and position, orientation, or trajectory of a medical instrument or medical device.

Further, an imaging and guidance system may combine each of the techniques described above, i.e., those described in association with avoiding or reducing visual obstruction in ultrasound images, generating and presenting reference ultrasound images, and determining and presenting position, orientation, or trajectory of medical instruments or medical devices using EM tracking. In this case, the output of the system may be presented together on a display device, as guidance information, e.g., simultaneously, live ultrasound images obtained using split aperture, wide angle, or other beamforming techniques, reference ultrasound images, and imagery or information indicating position, orientation, or trajectory of instruments or devices.

Any suitable system or systems may be utilized with the examples of the present disclosure, e.g., the systems described in U.S. Pat. No. 10,548,666 to Girotto et al., entitled SYSTEMS AND METHODS FOR ULTRA-SOUND IMAGE-GUIDED ABLATION ANTENNA PLACEMENT; and U.S. Pat. No. 8,401,616 to Verard et al., entitled NAVIGATION SYSTEM FOR CARDIAC THERAPIES, the entire content of each of which is incorporated herein by reference. Various techniques, devices and systems described in this disclosure may use or be used with techniques, devices and systems described in U.S. Patent Publication No. 2019/0307518, U.S. Patent Publication No. 2019/0307516, and U.S. Provisional Application No. 62/653,988, filed Apr. 6, 2018, the contents of each of which is incorporated herein by reference.

The system for guiding a medical instrument or medical device through a region of the patient may include various imaging and tracking systems and a controller (e.g., comprising one or more processors) that is adapted to utilize data from these imaging and tracking systems and generate an image for display. Such an image may provide any suitable information to a clinician that is performing a medical procedure. For example, in one or more examples, the controller may generate one or more images for display that shows at least one of a position, orientation, and trajectory of a medical instrument or medical device in relation to a plane or 3D image of the region as the clinician guides the medical instrument or medical device into and out of the region of a patient. The controller may also be adapted to provide one or more markers or target zones in the image displayed to guide the clinician to a target region of the patient or to identify a target region of the patient.

In one or more examples, an ultrasound imaging system may be configured to reduce or avoid visual obstructions, such as artifacts or shadowing, caused by medical instruments or medical devices in a field of view of the imaging system. An ultrasound imaging system may be configured so as to transmit pulses of ultrasound energy and receive reflected ultrasound energy (i.e., echoes) in a field of view. In some examples, an ultrasound imaging system may be configured to transmit ultrasound energy and receive reflected ultrasound energy in field(s) of view that entirely or partially avoid the medical instrument or medical device, which would otherwise cause obstructions in the reflected ultrasound energy and, ultimately, visual obstructions, such as shadowing, in an ultrasound image of the anatomical region of interest.

Figure 3A:
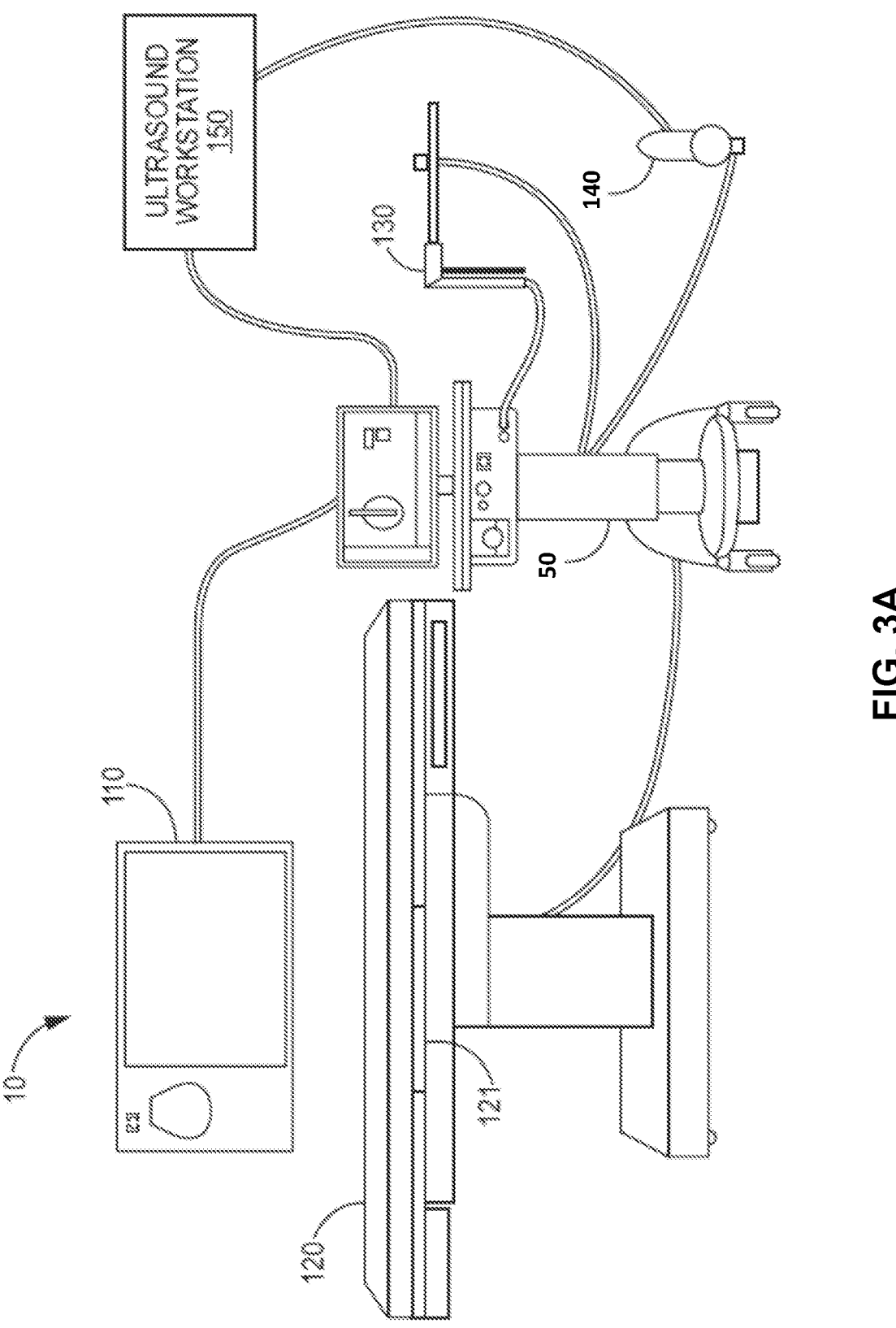
FIG. 3A is a schematic perspective view of one example of a system for guiding a medical instrument or medical device through a region of a patient.

FIG. 3A is a schematic perspective view of one example of a system 10, which includes a guidance workstation 50, a display device 110, a table 120, a medical instrument or medical device 130, an ultrasound imager 140, and an ultrasound workstation 150. Guidance workstation 50 may include, for example, a laptop computer, desktop computer, tablet computer, smart phone, or other similar device. Guidance workstation 50 may be configured to control an electrosurgical generator, a peristaltic pump, a power supply, or any other accessories and peripheral devices relating to, or forming part of, system 10.

Display device 110 is configured to output instructions, images, and messages relating to at least one of a performance, position, orientation, or trajectory of the medical instrument or medical device 130. Further, the display device 110 may be configured to output information regarding the medical instrument or medical device 130, e.g., model number, type, size, etc. Table 120 may be, for example, an operating table or other table suitable for use during a surgical procedure that may optionally include an electromagnetic (EM) field generator 121. EM field generator 121 may be optionally included and used to generate an EM field during the procedure and, when included, may form part of an EM tracking system that is used to track the positions of one or more medical instruments or medical devices within the body of a patient. EM field generator 121 may include various components, such as a specially designed pad to be placed under, or integrated into, an operating table or patient bed. An example of such an EM tracking system is the AURORA™ system sold by Northern Digital Inc. While the present disclosure describes the use of system 10 in a surgical environment, it is also envisioned that some or all of the components of system 10 may be used in alternative settings, for example, in an imaging laboratory or an office setting.

A medical instrument or medical device 130 may also be visualized by using ultrasound imaging. In the example of FIG. 3A, an ultrasound imager 140, such as an ultrasound wand, may be used to image the patient's body during the procedure to visualize the locations of medical instruments or medical devices, such as surgical instruments, device delivery or placement devices, and implants, inside the patient's body. Ultrasound imager 140 may comprise an ultrasound probe having an ultrasound transducer array. In some examples, ultrasound imager 140 may include an ultrasound transducer array, including a plurality of transducer elements, e.g., as shown in FIGS. 16A-F and discussed below. Ultrasound imager 140 may optionally have an EM tracking sensor embedded within or attached to an ultrasound wand or probe, for example, as a clip-on sensor, or a sticker sensor.

Ultrasound imager 140 may image a region or interest in the patient's body. The particular region of interest may be dependent on anatomy and the intended therapy. For example, when placing a cardiac valve, a three chamber cardiac view may be in the region of interest. When ablating for atrial fibrillation, the posterior left atrial wall and pulmonary veins may be in the region of interest.

As described further herein, ultrasound imager 140 may be positioned in relation to medical instrument or medical device 130 such that the medical instrument or medical device is at an angle to the ultrasound image plane, thereby enabling the clinician to visualize the spatial relationship of the instrument or medical device with the ultrasound image plane and with objects being imaged. Further, if provided, the EM tracking system may also track the location of ultrasound imager 140. In one or more examples, one or more ultrasound sensors 140 may be placed inside the body of the patient. The EM tracking system may then track the locations of such ultrasound sensors 140 and the medical instrument or medical device 130 inside the body of the patient. In some examples, the functions of ultrasound workstation 150 may be performed by guidance workstation 50 and ultrasound workstation 150 would not be present.

The location of the medical instrument or medical device 130 within the body of the patient may be tracked during the surgical procedure. An exemplary method of tracking the location of the medical instrument or medical device 130 includes using the EM tracking system, which tracks the location of the medical instrument or medical device by tracking sensors attached to or incorporated in the medical instrument or medical device. Various types of sensors may be used, such as a printed sensor, the construction and use of which is more fully described in co-pending U.S. Patent Publication No. 2016/0174873, entitled MEDICAL INSTRUMENT WITH SENSOR FOR USE IN A SYSTEM AND METHOD FOR ELECTROMAGNETIC NAVIGA- TION, the entire content of which is incorporated herein by reference. Prior to starting the procedure, the clinician may verify the accuracy of the tracking system using any suitable technique or techniques.

Any suitable medical instrument or medical device 130 may be utilized with the system 10. Examples of medical instruments or devices include one or more implantable devices, implant delivery devices, therapy delivery devices, surgical devices, mechanical circulatory support (e.g. LVAD) devices, coronary stent devices, heart valve devices, heart valve repair devices, cardiac ablation devices, cardiac lead devices, drug delivery devices, catheter delivery devices, or endoscopic delivery devices.

Figure 3B:
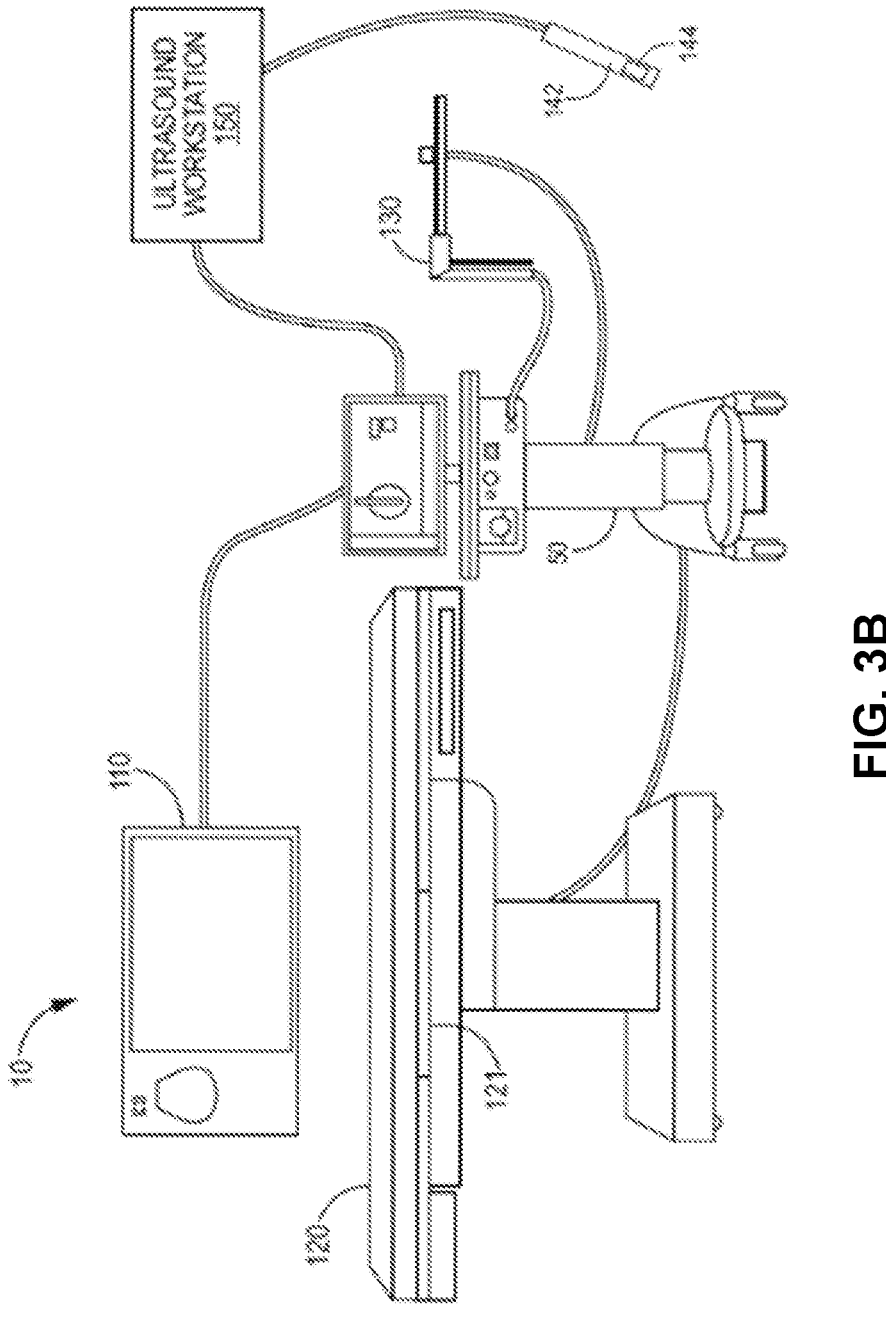
FIG. 3B is a schematic perspective view of another example of a system for guiding a medical instrument or medical device through a region of a patient.

FIG. 3B is a schematic perspective view of another example of a system 10, such as in FIG. 3A, where ultrasound imager 142 is intended for use inside a patient's body, such as with a transesophageal ultrasound probe, sometimes referred to as a transesophageal echocardiogram (TEE) probe. Hence, FIG. 3B substantially corresponds to FIG. 3A but illustrates use of ultrasound imager 142 with a TEE probe. In the example of FIG. 3B, ultrasound imager 142 comprises an ultrasound probe having an ultrasound transducer array 144 including a plurality of ultrasound transducer elements. Ultrasound transducer array 144 may be configured as a single transducer array or multiple transducer arrays, each including a plurality of ultrasound transducer elements, e.g., as shown in FIGS. 15A-15F and discussed below.

Figure 4:
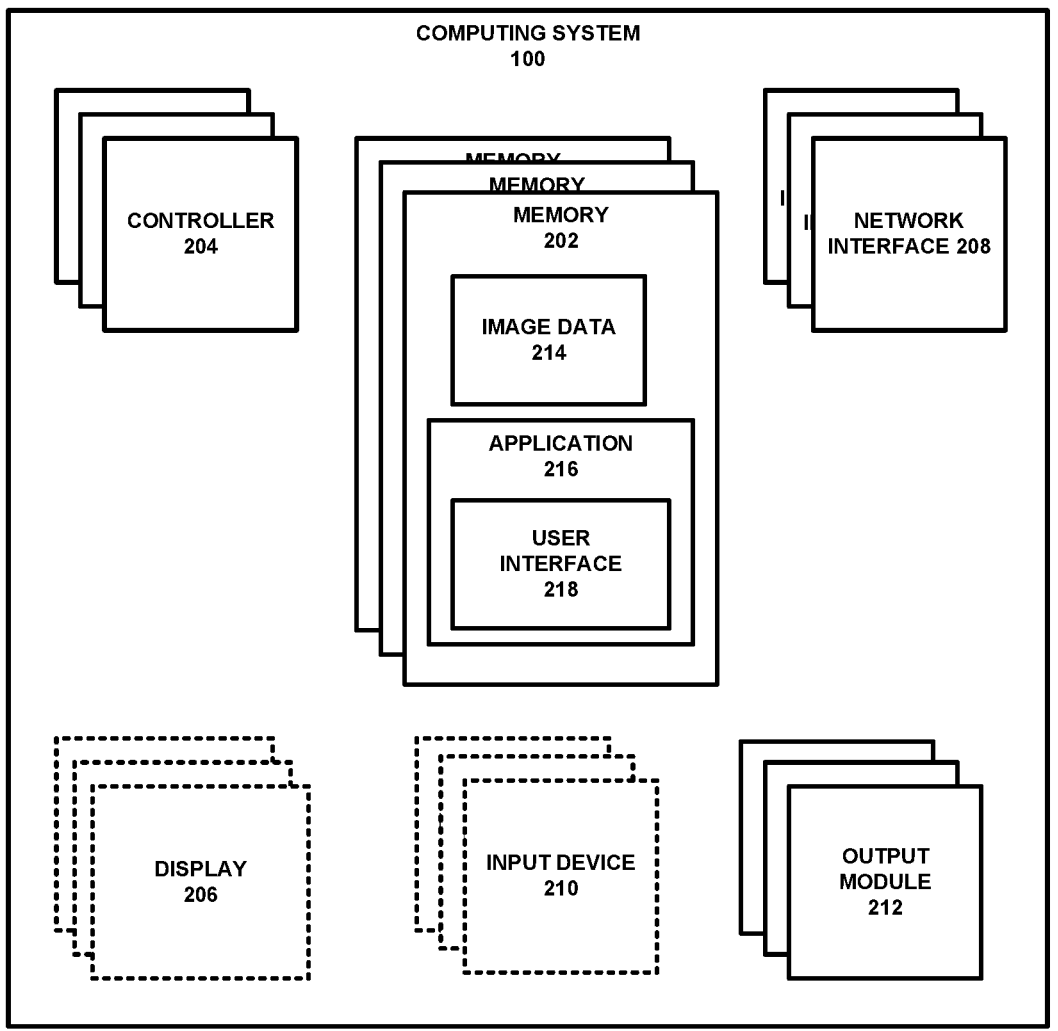
FIG. 4 is a schematic view of one example of a computing system of the system of FIG. 3A or 3B.

FIG. 4 is a schematic view of one example of a computing system 100 of system 10 of FIG. 3A or 3B. Computing system 100 includes computing devices configured to perform processing, control and other functions associated with guidance workstation 50, ultrasound workstation 150, ultrasound imager 140 or 142, and an optional EM tracking system. As shown in FIG. 4, computing system 100 represents multiple instances of computing devices, each of which may be associated with one or more of guidance workstation 50, ultrasound workstation 150, ultrasound imager 140 or 142, or the EM tracking system. Computing system 100 may include, for example, a memory 202, a controller 204, a display device 206, a network interface 208, an input device 210, or an output module 212, each of which may represent any of multiple instances of such a device within the computing system, for ease of description.

Reference to controller 204 refers to any of a plurality of controllers of computing system 100 suitably configured to perform a pertinent operation, including any of one or more controllers of any of guidance workstation 50, ultrasound workstation 150, ultrasound imager 140 or 142, or the EM tracking system, or combinations thereof. A given instance of controller 204 may include one or more processors, and a controller may be referred to in this disclosure, interchangeably, as controller 204, one or more processors, or one or more processors of controller 204.

In some examples, one or more processors associated with controller 204 in computing system may be distributed and shared across any combination of guidance workstation 50, ultrasound workstation 150, ultrasound imager 140 or 142, and the EM tracking system. Additionally, in some examples, control operations, processing operations or other operations performed by controller 204 may be performed by one or more processors residing remotely, such as one or more cloud servers or processors, each of which may be considered a part of computing system 100. Computing system 100 may be used to perform any of the methods described in this disclosure, and may form all or part of devices or systems configured to perform such methods, alone or in conjunction with other components, such as components of guidance workstation 50, ultrasound workstation 150, ultrasound imager 140 or 142, an EM tracking system, or a system including any or all of such systems.

Memory 202 of computing system 100 includes any non-transitory computer-readable storage media for storing data or software that is executable by controller 204 and that controls the operation of guidance workstation 50, ultrasound workstation 150, ultrasound imager 140 or 142, or EM tracking system, as applicable. In one or more examples, memory 202 may include one or more solid-state storage devices such as flash memory chips. In one or more examples, memory 202 may include one or more mass storage devices connected to the controller 204 through a mass storage controller (not shown) and a communications bus (not shown).

Although the description of computer-readable media herein refers to a solid-state storage, it should be appreciated by those skilled in the art that computer-readable storage media may be any available media that may be accessed by the controller 204. That is, computer readable storage media includes non-transitory, volatile and non-volatile, removable and non-removable media implemented in any method or technology for storage of information such as computer-readable instructions, data structures, program modules, or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium that may be used to store the desired information and that may be accessed by computing system 100. In one or more examples, computer-readable storage media may be stored in the cloud or remote storage and accessed using any suitable technique or techniques through at least one of a wired or wireless connection.

Memory 202 may store at least one of application 216 or image data 214 such as reference image data. Application 216 may, when executed by controller 204, cause display device 206 to present user interface 218. In some implementations, display device 206 may be located external to computing system 100.

Controller 204 may be implemented by one or more processors, which may include any number of fixed-function circuits, programmable circuits, or a combination thereof. As described here, guidance workstation 50 may perform various control functions with respect to ultrasound imagers 140 and 142 and may interact extensively with ultrasound workstation 150. Guidance workstation 50 may be linked to ultrasound workstation 150, enabling guidance workstation 50 to control the operation of ultrasound imager 140 or 142 and receive the output of ultrasound imager 140 or 142. In some examples, controller 204 may be considered to include one or more processors in guidance workstation 50, one or more processors in ultrasound workstation 150, one or more processors in ultrasound imager 140 or 142, or any combination thereof. In some examples, ultrasound workstation 150 may control various operations of ultrasound imager 140 or 142.

In various examples, control of any function by controller 204 may be implemented directly or in conjunction with any suitable electronic circuitry appropriate for the specified function. Fixed-function circuits refer to circuits that provide particular functionality and are preset on the operations that may be performed. Programmable circuits refer to circuits that may programmed to perform various tasks and provide flexible functionality in the operations that may be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits.

Instructions may be executed by one or more processors, such as one or more digital signal processors (DSPs), general purpose microprocessors, application specific integrated circuits (ASICs), field programmable gate arrays (FPGAs), graphics processing units (GPUs) or other equivalent integrated or discrete logic circuitry. Accordingly, the term "controller," as used herein may refer to one or more processors having any of the foregoing processor or processing structure or any other structure suitable for implementation of the techniques described herein. In addition, in some aspects, the functionality described herein may be provided within dedicated hardware or software modules configured for encoding and decoding, or incorporated in a combined codec. Also, the techniques could be fully implemented in one or more circuits or logic elements.

Display device 206 may be touch sensitive or voice activated, enabling display device 206 to serve as both an input and output device. Alternatively, a keyboard (not shown), mouse (not shown), or other data input devices may be employed.

Network interface 208 may be adapted to connect to a network such as a local area network (LAN) that includes a wired network or a wireless network, a wide area network (WAN), a wireless mobile network, a Bluetooth network, or the internet. For example, guidance workstation 50 may receive medical image data or one or more other types of image data of a patient from a server, for example, a hospital server, internet server, or other similar servers, for use during the procedure. Patient image data or other image data may also be provided to guidance workstation 50 via a memory 202. Reference image data such as a reference ultrasound image may also be provided to guidance workstation 50 from an imaging system during or prior to the medical procedure. Guidance workstation 50 may receive updates to its software, for example, application 216, via network interface 208. Guidance workstation 50 may also display notifications on display device 206 that a software update is available.

Input device 210 may be any device that enables a user to interact with guidance workstation 50, such as, for example, a mouse, keyboard, foot pedal, touch screen, augmented-reality input device receiving inputs such as hand gestures or body movements, or voice interface.

Output module 212 may include any connectivity port or bus, such as, for example, parallel ports, serial ports, universal serial busses (USB), or any other similar connectivity port known to those skilled in the art.

Application 216 may be one or more software programs stored in memory 202 and executed by controller 204 of guidance workstation 50. As will be described in more detail herein, during the planning phase, an application 216 executed by controller 204 of guidance workstation 50 guides a clinician or physician through a series of steps to identify a target, size the target, size a treatment zone, or determine an access route to the target for later use during the procedure phase. In one or more examples, application 216 is loaded on computing devices in an operating room or other facility where surgical procedures are performed, and is used as a plan or map to guide a clinician performing a surgical procedure, with or without feedback from the medical instrument or medical device 130 used in the procedure to indicate where the medical instrument or medical device 130 is located in relation to the plan. In one or more examples, system 10 provides guidance workstation 50 with data regarding the location of the medical instrument or medical device 130 within the body of the patient, such as by EM tracking, which application 216 may then use to indicate on the plan where the medical instrument or medical devices are located. In one or more examples, the system 10 may provide guidance workstation 50 with data regarding the location of two or more medical instrument or medical devices within the body of the patient.

Application 216 may be installed directly on guidance workstation 50, or may be installed on another computer, for example a central server, and opened on guidance workstation 50 via network interface 208. Application 216 may run natively on guidance workstation 50, as a web-based application, or any other format known to those skilled in the art. In one or more examples, application 216 will be a single software program having all of the features and functionality described in the present disclosure. In one or more examples, application 216 may be two or more distinct software programs providing various parts of these features and functionality. For example, application 216 may include one software program for use during the planning phase and a second software program for use during the procedure phase. In one or more examples, application 216 may include different programs for different types of treatments. In such instances, the various software programs forming part of application 216 may be enabled to communicate with each other or import and export various settings and parameters relating to the treatment or the patient to share information. For example, a treatment plan and any of its components generated by one software program during the planning phase may be stored and exported to be used by a second software program during the procedure phase.

Application 216 communicates with a user interface 218, which generates an image for presenting visual interactive features to a clinician, for example, on display device 206 and for receiving clinician input, for example, via a user input device. Examples of the visual interactive features are described herein with reference to FIGS. 5A-5E and 6.

Guidance workstation 50 may be linked to display device 110, thus enabling guidance workstation 50 to control the output on display device 110 along with the output on display device 206. Guidance workstation 50 may control display device 110 to display output that is the same as or similar to the output displayed on display device 206. For example, the output on display device 206 may be mirrored on display device 110. In one or more examples, guidance workstation 50 may control display device 110 to display different output from that displayed on display device 206. For example, display device 110 may be controlled to display guidance images and information during the surgical procedure, while display device 206 is controlled to display other output, such as configuration or status information.

Figure 5A:
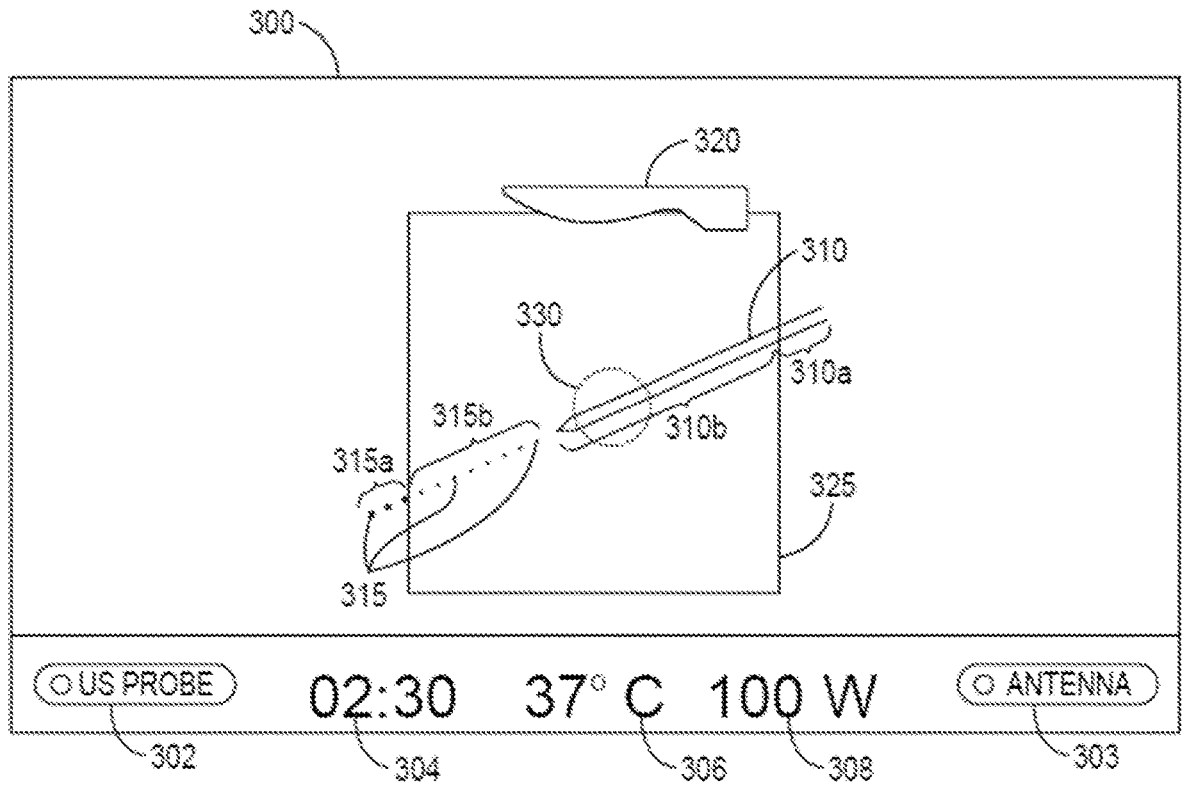
FIG. 5A is a schematic view of one example of a display provided by the system of FIG. 3A or 3B.

FIG. 5A is a schematic view of an image 300 generated by user interface 218 that may be presented by guidance workstation 50 on display device 206 or display device 110. In some examples, image 300 in FIG. 5A, and in FIGS. 5B-5E, and image 301 in FIG. 6, may form part of a graphical user interface (GUI). A user may interact with a GUI associated with image 300 via one or more user input devices such as a pointing device, keyboard, touchscreen, voice command or gesture command. Image 300 includes graphical representation of an antenna 310 corresponding to a medical instrument or medical device 130, a graphical representation of an ultrasound imager 320 corresponding to ultrasound imager 140 or 142, a graphical representation of a trajectory 315 of the medical instrument or medical device, an ultrasound image plane 325, and a projected zone indicator 330 showing a projected region as configured for the current procedure.

Ultrasound image plane 325 may include an ultrasound image (not shown here for the purpose of more clearly depicting the elements being described) based on ultrasound image data captured by ultrasound imager 140 or 142. Image 300 may further include a probe indicator 302 and antenna indicator 303 that indicates whether ultrasound imager 140 or 142 and the medical instrument or medical device 130 are connected to guidance workstation 50 and system 10. Image 300 may also include other indicators of time 304, temperature 306, and wattage 308 or other information related to the procedure, e.g., temperature and wattage of a medical instrument or medical device. In one or more examples, image 300 may further include information regarding the medical instrument or medical device 130, e.g., model, type, dimensions, etc.

Trajectory 315 shows the trajectory at which the medical instrument or medical device 130 is being navigated inside the patient's body. In one or more examples, the length of trajectory 315 corresponds to the length of the medical instrument or medical device 130. In one or more examples, the trajectory of the medical instrument or medical device shown in the display has at least one of a length or width approximately equal to a respective length and width of the medical instrument or medical device. As used herein, the term "approximately equal" means that at least one of the length or width of the trajectory as shown in the image 300 is no greater than or less than 1 cm of the respective length or width of the medical instrument or medical device 130. Thus, when positioning the medical instrument or medical device 130 and ultrasound imager 140 outside the patient's body, trajectory 315 will show the distance the medical instrument or medical device 130 may be navigated into the patient's body. As such, the clinician may determine whether the medical instrument or medical device 130 may reach the target region inside the patient's body before inserting the instrument or medical device into the patient's body.

In one or more examples, image 300 may depict antenna 310 of medical instrument or medical device 130 and at least one of its position, orientation, or trajectory 315 of the medical instrument or medical device as outlines such that the ultrasound image displayed on ultrasound image plane 325 is not obscured by such outlines. Image 300 further shows the antenna 310 of medical instrument or medical device 130 and at least one of its position, orientation, or trajectory 315 in relation to a plane of the ultrasound image data, i.e., the ultrasound image plane 325. In one or more examples, the controller 204 of guidance workstation 50 is further adapted to determine an intersection between the medical instrument or medical device 130 and ultrasound image plane 325 and display an indicator of the intersection between the medical instrument or medical device and the plane of the ultrasound image data in the image 300.

For example, when the medical instrument or medical device 130 does not intersect ultrasound image plane 325, the antenna 310 may be depicted as shadowed (e.g. dimmed or greyed-out). For example, as shown in FIG. 5A, the antenna 310 is depicted in a shadowed section 310b for the portion of the antenna displayed behind ultrasound image plane 325. Likewise, trajectory 315 is depicted as a shadowed section 315b for the portion of trajectory 315 that is behind ultrasound image plane 325. In contrast, the portion of the trajectory 315a that is in front of ultrasound image plane 325 is shown as regular or solid image (of normal brightness and not shadowed or dimmed). In one or more examples, one or more colors may be utilized to depict the shadowed section 315b, and one or more differing colors may be utilized to depict the trajectory 315. Further, in one or more examples, the shadowed section 315b may be depicted in dashed lines and the trajectory 315 may be depicted in solid lines.

Figure 5B:
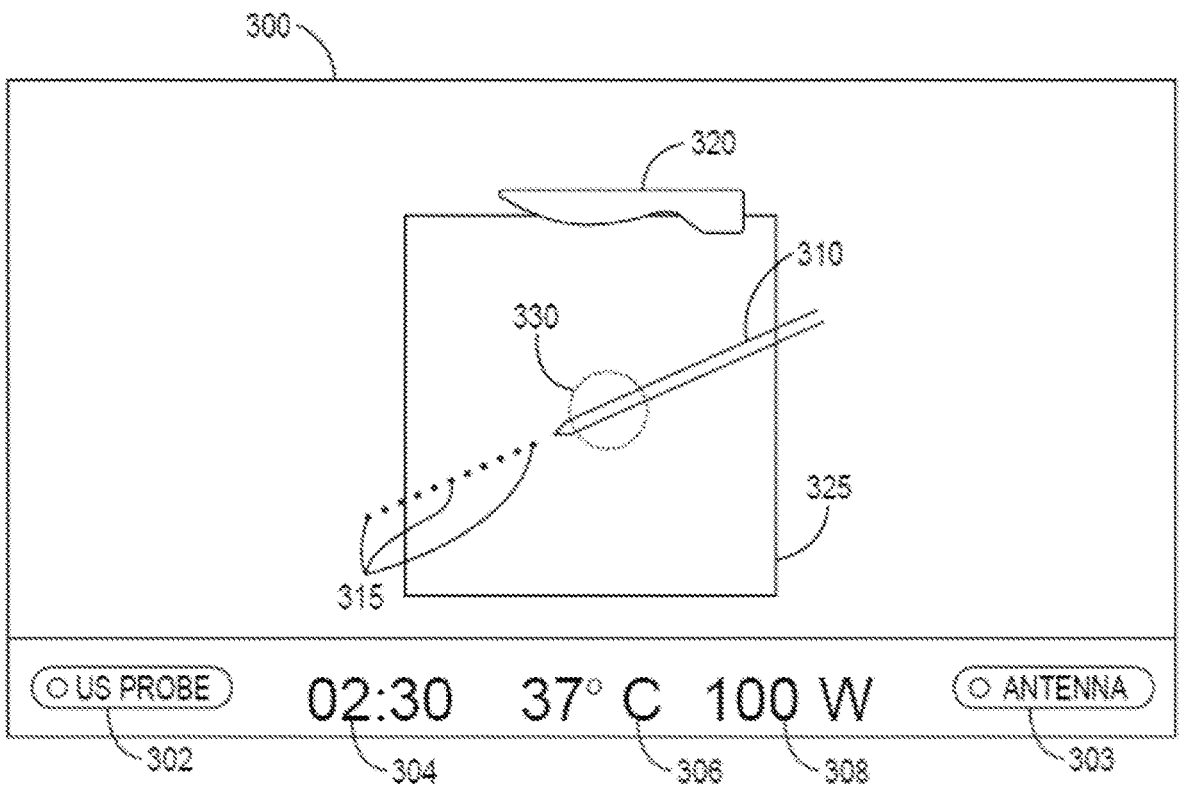
FIG. 5B is a schematic view of another example of a display provided by the system of FIG. 3A or 3B.

While FIG. 5A shows an example where all of the antenna 310 and trajectory 315 are behind ultrasound image plane 325, FIG. 5B shows an example where all of the antenna and trajectory are in front of ultrasound image plane 325. That is, the medical instrument or medical device 130 is located entirely in front of, and does not intersect, ultrasound image plane 325 of the image generated by ultrasound imager 140.

Figure 5C:
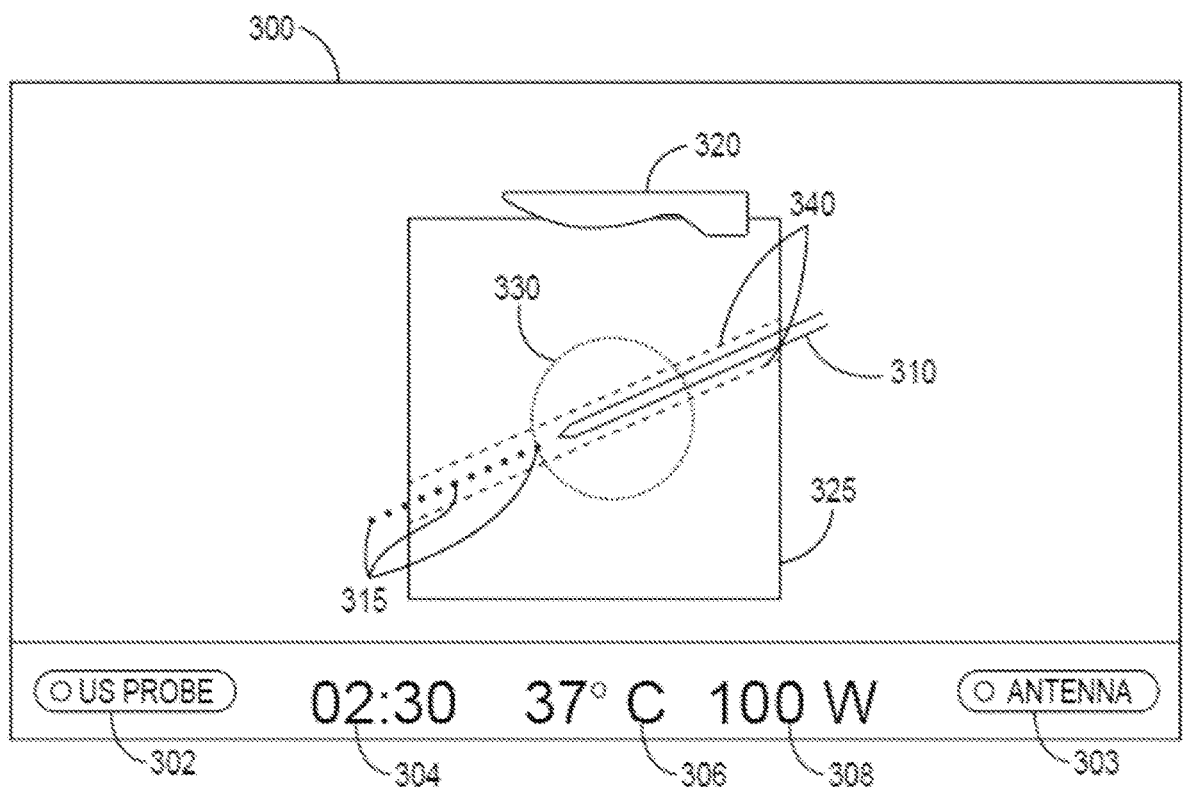
FIG. 5C is a schematic view of another example of a display provided by the system of FIG. 3A or 3B.

FIG. 5C shows another example image 300 generated by user interface 218 that may be displayed by guidance workstation 50 on display device 206 or display device 110. FIG. 5C includes many of the same elements as FIGS. 5A and 5B. Those elements are identified using the same reference numerals as in FIGS. 5A and 5B and will not be described again for purpose of brevity.

FIG. 5C shows an example where the antenna 310 of medical instrument or medical device 130 is co-planar with ultrasound image plane 325. The area of intersection between a plane of the antenna 310 and ultrasound image plane 325 is indicated by an obround 340. Because antenna 310 is co-planar with ultrasound image plane 325, obround 340 is shown as two parallel lines on either side of the antenna 310 and trajectory 315.

Figure 5D:
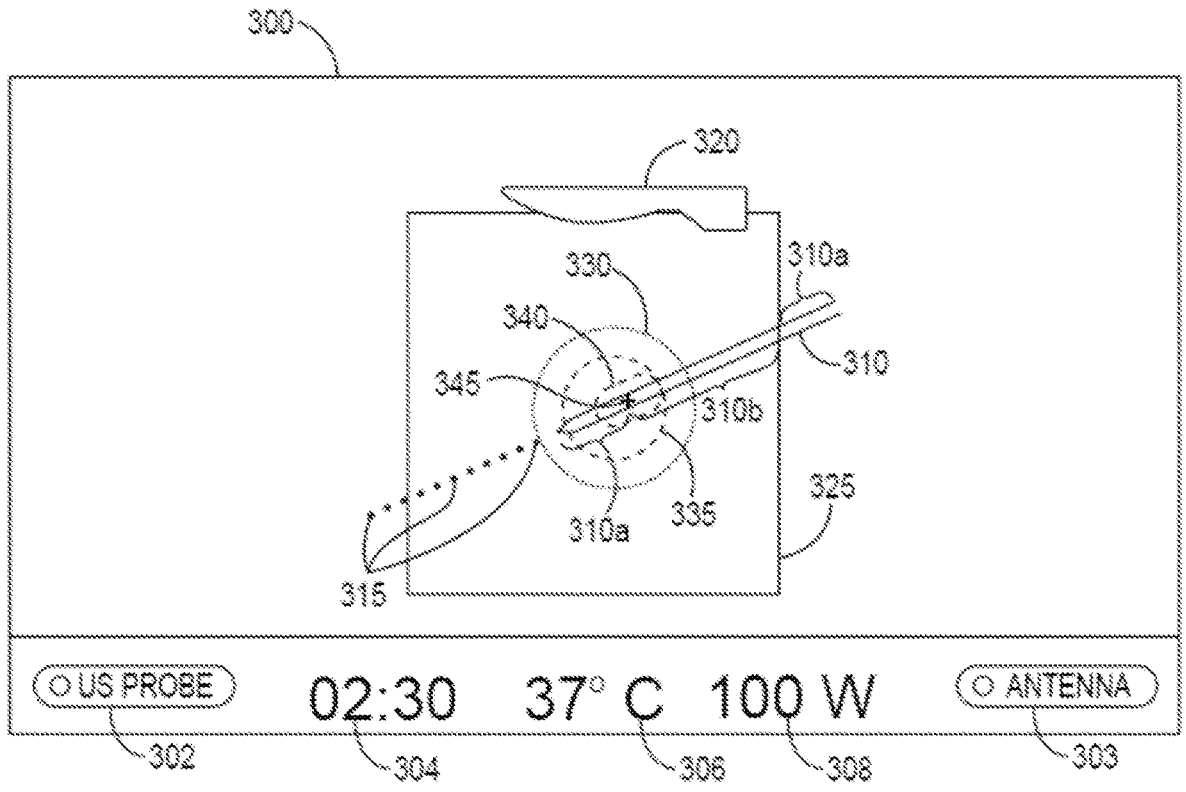
FIG. 5D is a schematic view of another example of a display provided by the system of FIG. 3A or 3B.

FIG. 5D shows another example of image 300, where the antenna 310 of medical instrument or medical device 130 intersects ultrasound image plane 325. Unlike in FIG. 5C, where the antenna 310 is co-planar with ultrasound image plane 325 and obround 340 extends the length of antenna 310 and trajectory 315, in FIG. 5D, obround 340 appears elliptical around the area of intersection between the antenna and ultrasound image plane. The length and position of obround 340 is determined by the angle of intersection between the antenna 310 and ultrasound image plane 325. That is, obround 340 shows the direction and acuteness of the angle of intersection between the antenna 310 and ultrasound image plane 325. The point of intersection between the antenna 310 and ultrasound image plane 325 is shown by intersection indicator 345.

Image 300 may further show a progress indicator 335 after guidance workstation 50 determines that the procedure has been started. The progress indicator 335 may show the progress of the procedure being performed. The progress indicator 335 will start close to the antenna 310 and move out toward projected zone indicator 330 as the procedure proceeds. The progress indicator 335 may be depicted using any suitable images or indicia, e.g., color, line thickness, brightness, etc.

Figure 5E:
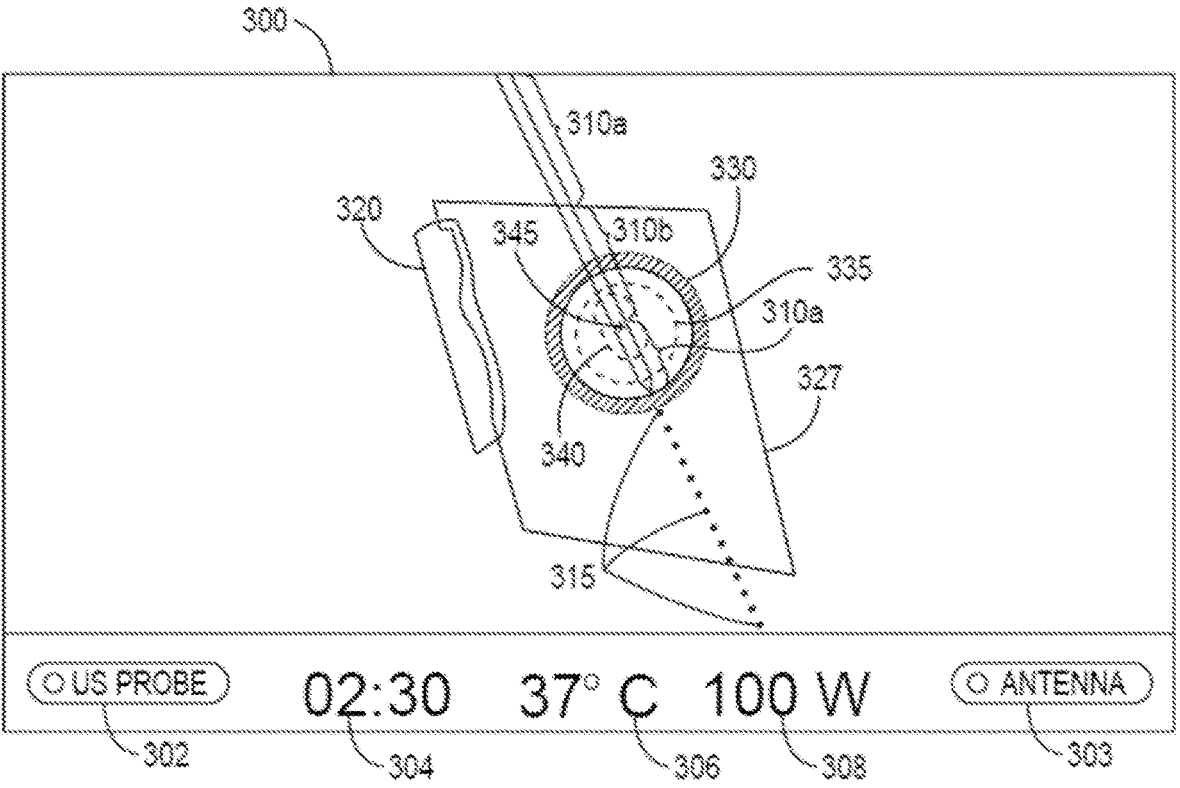
FIG. 5E is a schematic view of another example of a display provided by the system of FIG. 3A or 3B.

FIG. 5E shows another example of image 300 generated by user interface 218 that may be displayed by guidance workstation 50 on display device 206 or display device 110. FIG. 5E includes many of the same elements as FIGS. 5A-5D. Those elements are identified using the same reference numerals as in FIGS. 5A-5D and will not be described again for purpose of brevity.

FIGS. 5A-5D show ultrasound image plane 325 in which the orientation of ultrasound imager 320 and ultrasound image plane 325 are maintained in a fixed orientation normal to image 300. FIG. 5E, in contrast, depicts ultrasound imager 320 and an ultrasound image plane 327 according to an orientation of ultrasound imager 140 within an EM field generated by EM field generator 121. Thus, when the clinician moves ultrasound imager 140 or 142, the depiction of ultrasound imager 320 and ultrasound image plane 327 in image 300 changes according to the movement and angle of ultrasound imager 140 or 142 within the EM field, thereby providing a perspective view of the target region or zone and the position of the medical instrument or medical device 130 therein.

Image 300 may further include a perspective view area configured to correspond to a portion of the EM field that includes the treatment region or target zone. For example, the patient may be positioned on table 120 such that the EM field generated by EM field generator 121 includes the target zone. Guidance workstation 50 may then automatically or with assistance from the clinician select a portion of the EM field that includes the target zone, and may configure application 216 or image 300 to depict the antenna 310, ultrasound imager 320, ultrasound image plane 327, and the various other elements described herein in the perspective view area based on their detected or determined positions within the EM field.

For example, ultrasound image plane 327 and ultrasound imager 320 may only be depicted in the perspective view area when ultrasound imager 140 or 142 is detected to be positioned within the portion of the EM field that is configured to be displayed in the perspective view area of image 300. Likewise, the antenna 310 may only be depicted in the perspective view area when the medical instrument or medical device 130 is detected to be positioned within the portion of the EM field that is configured to be displayed in the perspective view area of image 300. Thus, when ultrasound imager 140 or 142 or the medical instrument or medical device 130 are not in the portion of the EM field that is configured to be displayed in the perspective view area of image 300, image 300 will not display ultrasound imager 320, ultrasound image plane 327, or antenna 310 in the perspective view area. The portion of the EM field that is configured to be displayed in the perspective view area of image 300 may be adjusted during the procedure, such as by moving or zooming in and out.

As depicted in FIG. 5E, ultrasound imager 140 is rotated approximately 90° to the left and obliquely to the plane of the portion of the EM field shown in the perspective view area of image 300. These differences in orientation assist the clinician in understanding how movement of ultrasound imager 140 or 142 affects both ultrasound image plane 327 and ultrasound image plane 325. As depicted in FIG. 5E, projected zone indicator 330 or progress indicator 335 may be three-dimensional (3D) projections. This 3D projection of either projected zone indicator 330 or progress indicator 335 provides greater understanding of how the target zone interacts with all tissue and other structures in the zone during treatment. Further, these features allow the clinician to sweep across the medical instrument or medical device 130 to ascertain with greater clarity the effects of the treatment on the treatment zone.

Figure 6:
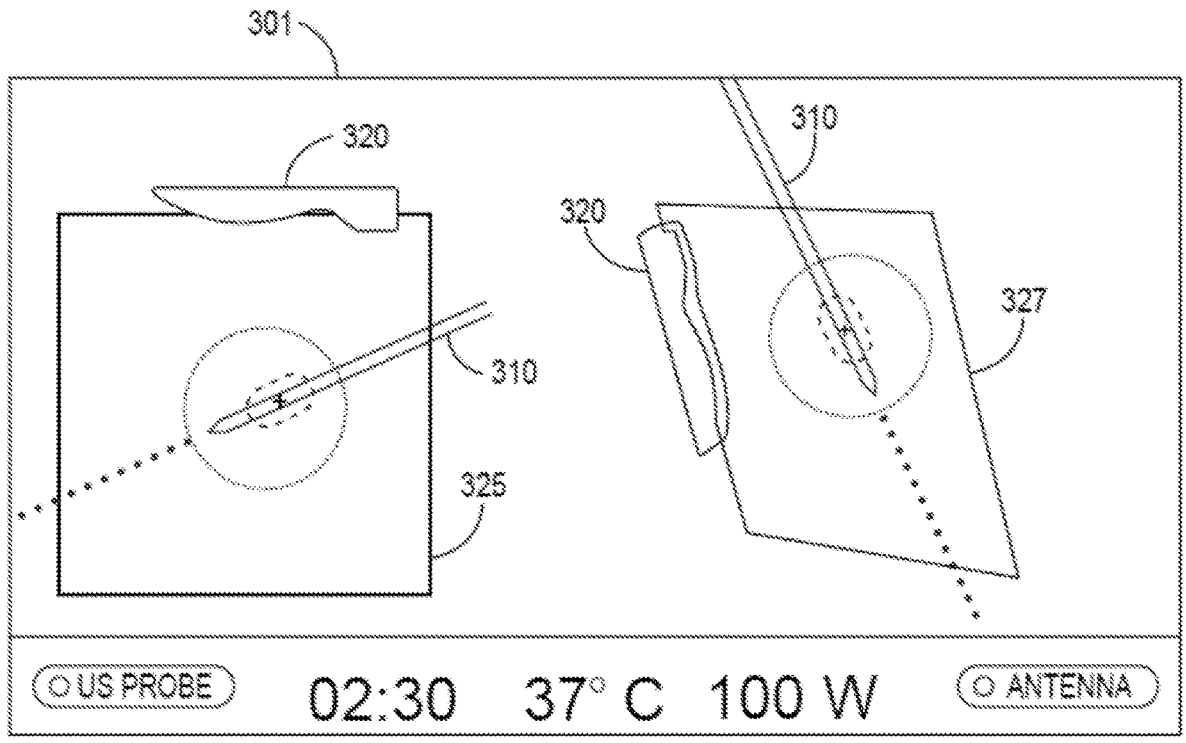
FIG. 6 is a schematic view of another example of a display provided by the system of FIG. 3A or 3B.

FIG. 6 shows another example of an image 301 generated by user interface 218 that may be displayed by guidance workstation 50 on display device 206 or display device 110. FIG. 6 includes many of the same elements as FIGS. 5A-5E. Those elements are identified using the same reference numerals as in FIGS. 5A-5E and will not be described again for purpose of brevity. Again, in some examples, image 301 of FIG. 4 may form part of a graphical user interface (GUI). For example, a user may interact with a GUI associated with image 301 via one or more user input devices such as a pointing device, keyboard, touchscreen, voice command or gesture command.

Image 301 includes side-by-side depictions of ultrasound image plane 325, which is displayed normal to image 300, as shown in FIGS. 5A-5D, and ultrasound image plane 327, which is shown relative to the placement of ultrasound imager 140 or 142 within the EM field generated by EM field generator 121.

In one or more examples, guidance workstation 50 may be adapted to also identify one or more physiological landmarks within the region of the patient and generate one or more markers, icons, or indicia in the image 300 that augments these one or more physiological landmarks so that the clinician may more readily identify them during the procedure. In one or more examples, the physiological landmark of the region of the patient may include any suitable structure or portion of the patient's physiology, one or more portions of the heart including, for example, one or more valves or portions thereof, one or more chambers or portions thereof, the apex or portions thereof, the septum or portions thereof, one or more vessels leading to or from the heart including, for example, the aorta or portions thereof, the pulmonary artery or portions thereof, the pulmonary vein or portions thereof, the superior vena cava or portions thereof, or the inferior vena cava or portions thereof.

Further, in one or more examples, the image 300 includes at least one marker representative of the physiological landmark. In one or more examples, the controller 204 of guidance workstation 50 is adapted to attach these markers to the physiological landmarks such that the markers are dynamic. In other words, the markers are attached to the physiological landmarks such that the markers move in registration with the landmarks in the image 300. Such registration of the markers with the physiological landmarks may aid the clinician in guiding the medical instrument or medical device 130 to the target region of the patient even though the patient or the region is moving in connection, e.g., with inhalation and exhalation or the beating of a heart of the patient.

In one or more examples, guidance workstation 50, upon execution of application 216, may be adapted to use machine learning or artificial intelligence (AI) techniques to identify one or more physiological landmarks within the region of the patient and generate one or more markers, icons, and indicia in the image 300 that augments these one or more physiological landmarks so that the clinician may more readily identify them during the procedure. In one or more examples, application 216 applies one or more machine learning algorithms to identify one or more physiological landmarks within the region of the patient or to provide an optimum trajectory for guiding a medical instrument or medical device, such as a surgical instrument or an implantable device through a region of a patient based on data acquired during the procedure or data acquired prior to the procedure. The machine learning algorithms may also be applied to adjust the trajectory as the procedure advances. For example, one or more algorithms may form a wider trajectory line in the image 300 if there is a large target zone for treatment or it may adjust the trajectory angle once anchored (e.g., the algorithm starts with the trajectory point for entry into the heart but then adjusts the trajectory once that access anchor point is established).

Figure 7:
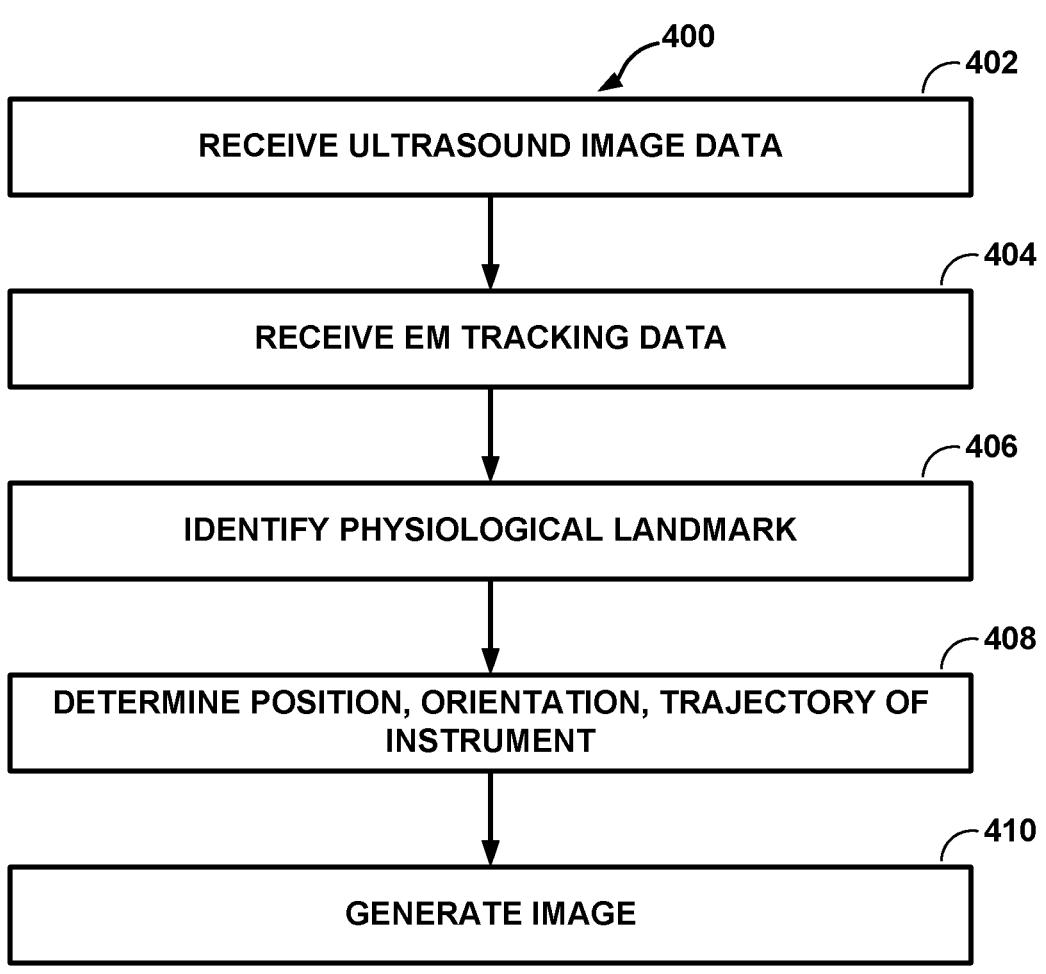
FIG. 7 is a flowchart of one example of a method of guiding a medical instrument or medical device through a region of a patient utilizing the system of FIG. 3A or 3B.

Any suitable technique or techniques may be utilized with the system 10 for guiding a medical instrument or medical device through a region of a patient. For example, FIG. 7 is a flowchart of one method 400 for guiding the medical instrument or medical device 130 through a region of a patient. Although described in reference to system 10 of FIGS. 3A, 3B, and 4-6, the method 400 may be utilized with any suitable system. In one or more examples, controller 204 may be adapted to utilize the method 400. Prior to beginning the procedure, any suitable settings may be entered manually by a clinician as user input data or may be preloaded from a preconfigured configuration settings file that was previously entered by the clinician. The settings may be based on a particular treatment profile specific to the patient or the type of procedure to be performed. Once received, image 300 may display these settings as indicators 304, 306, and 308, respectively.

Ultrasound image data may be received from the ultrasound imager 140 or 142 by guidance workstation 50 (402). The ultrasound image data may be relayed, for example, from ultrasound workstation 150. In some examples, controller 204 may include one or more processors, residing in guidance workstation 50 or on ultrasound workstation 150, configured to control various operations of ultrasound imager 140 or 142. Guidance workstation 50 may receive EM tracking data from the EM tracking system for ultrasound imager 140 and the medical instrument or medical device 130 (404). The EM tracking data is representative of positions and orientations of each of the ultrasound imager 140 or 142 and the instrument or medical device 130 relative to the region of the patient.

The clinician or controller 204 may identify one or more physiological landmarks based on the ultrasound image data using any suitable technique or techniques (406). Guidance workstation 50 may determine at least one of a position, orientation, or trajectory of the medical instrument or medical device 130 based on the EM tracking data (408) using any suitable technique or techniques. The guidance workstation 50 may also determine an intersection between the medical instrument or medical device 130, or the trajectory of the instrument or medical device, and the plane of the ultrasound image data received from ultrasound imager 140 or 142.

Controller 204 may generate an image 300 showing at least one of a position, orientation, or trajectory of the medical instrument or medical device 130 relative to the plane 325 of the ultrasound image data, which is based on the ultrasound image data received from ultrasound imager 140 or 142, and a target zone that is registered with the one or more physiological landmarks identified at 406 (410). Any suitable technique or techniques may be utilized to show the target zone. In one or more examples, the controller 204 of guidance workstation 50 may be adapted to determine the target zone based on user input data and generate the target zone in image 300 based upon the user input data. The guidance workstation 50 may display the image 300 on display device 206 or display device 110.

In one or more examples, the controller 204 may be adapted to determine whether at least one of the position, orientation, or trajectory of the medical instrument or medical device 130 has changed. If yes, then the controller 204 of guidance workstation 50 may be adapted to generate an updated image 300 showing at least one of an updated position, orientation, or trajectory of the medical instrument or medical device. These steps may be performed interchangeably or concurrently and may be performed iteratively throughout the procedure.

The method 400 may further include determining whether at least one of a position or orientation of the ultrasound sensor has changed and generating an updated image 300 showing an updated ultrasound image plane 325 if it is determined that at least one of the position or orientation of the ultrasound sensor has changed. Any suitable technique or techniques may be utilized to generate an updated image 300 if the position or orientation of the ultrasound sensor has changed.

In one or more examples, after updating the image 300, guidance workstation 50 may determine whether the procedure is complete. If yes, processing ends. If not, guidance workstation 50 continues to display the image 300.

In one or more examples, the guidance workstation 50 may determine whether the procedure has started. If yes, guidance workstation 50 may update the image 300 with an indicator of the progress of the procedure, for example, indicator 335 shown in FIGS. 5D and 5E. Thereafter, the guidance workstation 50 may determine whether the procedure has been completed. If yes, processing ends. If not, the image 300 is iteratively updated based on the progress of the procedure. The one or more markers or target zones may remain visible in the image even if the actual target region of the patient becomes obstructed or unavailable to the imaging system, e.g., due to shadowing or other artifacts.

The systems and methods described herein may be utilized for any procedure or treatment. For example, in one or more examples, the system 10 may be utilized for implantation of many different instruments or medical devices, either permanently or temporarily, such as left ventricular assist device (LVAD)s, pacemakers, defibrillators, neurostimulators, muscle stimulators, valves or valve repair or replacement devices (such as a mitral valve), stents, balloons, catheters or surgical devices such as catheters, trocars, canulae, ablation tools, or cutting tools. The system may be used to guide any of a wide variety of medical instruments or medical devices, and in any of a wide variety of surgical, therapeutic, intervention, or implantation procedures, including instruments and medical device separately, and instruments and medical devices together, e.g., where a medical instrument is used to deliver, place or implant a medical device. Systems for guiding a medical instrument or medical device, in accordance with various examples of this disclosure, may be used or adapted for use in guidance of the medical instruments and medical devices discussed above, and additional medical instruments and medical devices associated with various procedures.

Further examples of medical instruments or medical devices include, for purposes of example and without limitation, surgical instruments and medical devices associated with vascular access, transcatheter mitral valve replacement (TMVr) or transcatheter mitral valve repair (TMVR) (e.g., by trans-apical or trans-femoral access), left atrial appendance (LAA) occlusion, renal denervation, endovascular stent placement, cardiac lead implants (by catheter), cardiac lead implants (by stylet), extravascular implantable cardioverter defibrillator (EV-ICD), cardiac ablation, ventricular assist device placement, illiofemoral vein balloon or stent placement, electromechanical wave imaging, breast biopsy, liver ablation, fibroid ablation, lung cancer diagnosis and treatment, image-guided stapling, image-guided pancreas ablation, surgical adhesive or sealant delivery or placement, sacral neuromodulation lead implantation, brain tumor resection navigation, transcranial doppler stroke prediction, drug pump refill, brain structure post-tumor removal, and other medical instruments, medical devices and procedures in which guidance may be useful.

Figure 8:
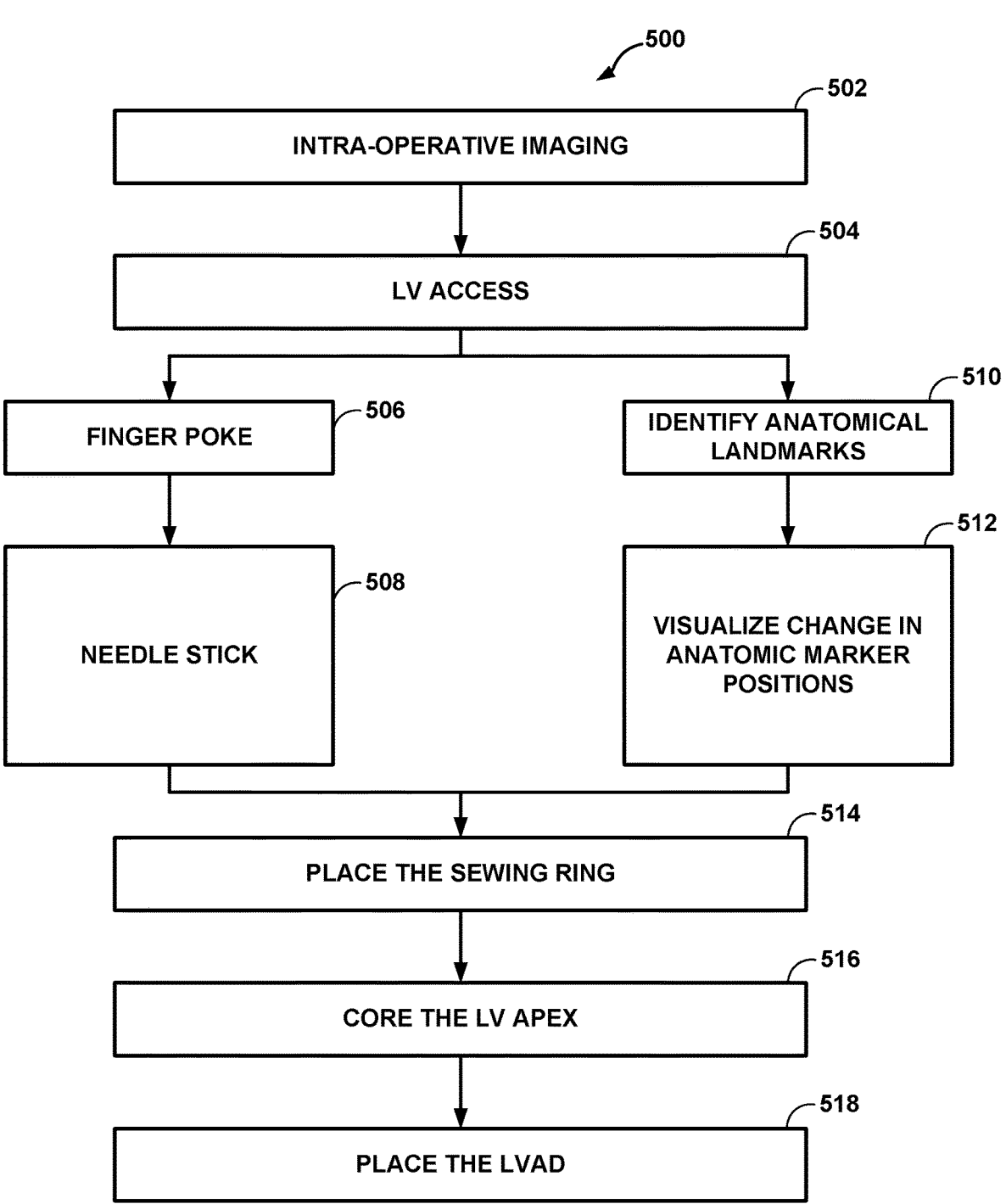
FIG. 8 is a flowchart of one example of a method of implanting a medical device utilizing the system of FIG. 3A or 3B.

FIG. 8 is a flowchart of one example of a method 500 of utilizing system 10 to implant an LVAD, as one example of an instrument or medical device. Although described in reference to the system 10 of FIGS. 3-6, the method 500 may be utilized with any suitable system. In one or more examples, the controller 204 may be adapted to utilize the method 500 of FIG. 8.

A target region within the patient may be intra-operative imaged using any suitable technique or techniques, e.g., echocardiography (502). Any suitable echocardiography techniques may be utilized, e.g., transesophageal echocardiography (TEE). A view of the intraventricular septum and mitral valve location may be imaged using the system 10. In one or more examples, physiological landmarks such as the mitral valve, IV septum, LV apex, aortic valve, etc., may be identified by the system 10 using any suitable technique.

LV access may be gained with the medical instrument or medical device 130 using any suitable technique, e.g., through a sternotomy or a thoracotomy (504). For a sternotomy, a finger poke where the clinician's finger pushes against the myocardium to define the LV apex by viewing the echocardiography image and identifying the indent relative to the geometry of the heart may be performed (506). In one or more examples, this step may not be required as the clinician may be presented with the augmented image of the medical instrument or medical device 130 and physiological markers in the image 300. In one or more examples, the deformation caused by the finger poke may be augmented in the image 300 and indicated with a marker or indicia and connected to a marker that is connected to the LV apex landmark identified by the system 10 or the clinician. Following identification of the LV apex, a needle stick may occur in which a needle may be inserted into the apex (508) and viewed on the echocardiograph image so that the needle is parallel to the septum and the needle trajectory is toward the mitral valve and not angled toward the aortic valve. Once again, this step may be eliminated by tracking the needle (e.g., medical instrument or medical device 130) and providing the user with an augmented image of the needle in the image 300. In one or more examples, one or more sensors may be connected to the needle such that the needle may be tracked using any suitable system, e.g., the EM tracking system.

For a thoracotomy, a clinician may identify anatomical landmarks, for example, by direct visualization through an incision by lifting the heart to the incision and identifying the vasculature to determine where the apex is located (510). Alternatively, controller 204 may identify anatomical landmarks, through, for example, machine vision. In one or more examples, augmented markers indicating various physiological landmarks may be dynamically connected to the landmarks in the image 300. Such markers may be registered with the physiological landmarks following heart elevation with the heart in the new position to help with the LV placement. In one or more examples, new markers may be provided for various physiological landmarks, and the changes between the preprocedural imaging markers and post heart elevation may be augmented in the image 300 so as to visualize a change in anatomic marker positions (512). Further, in one or more examples, a trajectory for the instrument or medical device 130 for implantation may be provided for both the normal vs. elevated positions of the heart.

Following identification of the apex, the clinician may place a sewing ring on the patient's heart using any suitable technique (514). Currently, some clinicians utilize a tissue marking pen to mark where the sewing ring will be placed on the LV apex, and the sewing ring may then be sutured to the heart at that location. In one or more examples, the EM system may be utilized to track the instrument or medical device 130 that will be utilized to place the sewing ring to track at least one of a position, orientation, or trajectory of the medical instrument or medical device. An augmented image of the instrument or medical device 130 may be added to the image 300 as well as an augmented image of the sewing ring. For example, one or more sensors may be added to the sewing ring such that the location of the sewing ring may be determined by the EM system.

Figure 9:
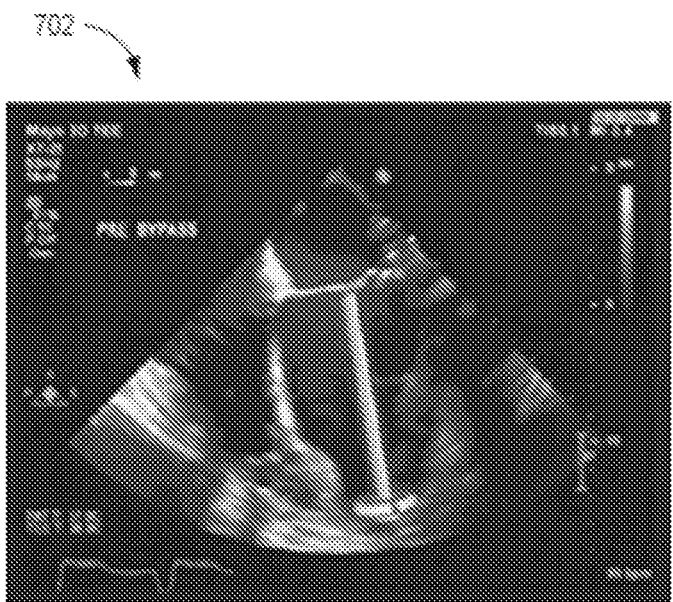
FIG. 9 is a schematic view of an image of an area of interest in a patient's heart with an augmented image of the sewing ring and a projected trajectory.

A trajectory for the medical instrument or medical device 130 may be evaluated relative to marker lines of the IV septum and mitral valve added to the image 300 to ensure proper placement (parallel to IV septum, perpendicular to the MV). Any suitable technique may be utilized to determine the proper trajectory. For example, FIG. 9 is a schematic view of an image 702 with an augmented image of the sewing ring and a projected trajectory. Further, the trajectory may be evaluated in multiple views in the image 702, e.g., cross-sectional, longitudinal, three-dimensional. In one or more examples, the proper trajectory may change color in the image 702 (or provide guideline lanes that indicate boundaries within which the medical instrument or medical device 130 is to be disposed) as the ring is manipulated on the surface of the heart (e.g., red indicates an incorrect placement, green indicates a desired placement, dashed line transitioning to solid line indicates desired placement, brightness of line or text that indicate desired placement). In one or more examples, the controller 204, e.g., of guidance workstation 50, may be adapted to measure one or more distances and angles between augmented markers and the trajectory of the medical instrument or medical device 130 and provide such distances to the clinician in the image 702 (e.g., a distance between the IV septum and a trajectory line of the instrument or medical device toward the apex and basal portion of heart, a distance between IV septum and the medical instrument or medical device trajectory, a distance between the free wall and instrument or medical device trajectory, etc.).

In one or more examples, the sewing ring may include a gimble that allows a desired number of degrees of freedom of an angle of the sewing ring relative to the epicardium of the heart after the ring is sutured to the heart. The augmented trajectory and visualization of the sewing ring in the image 702 may aid with optimizing placement angle of the gimble. The clinician may core the LV apex (516). Following attachment of the sewing ring, the clinician may place the LVAD by connecting the LVAD to the sewing ring (518) using any suitable technique or techniques.

Figure 10:
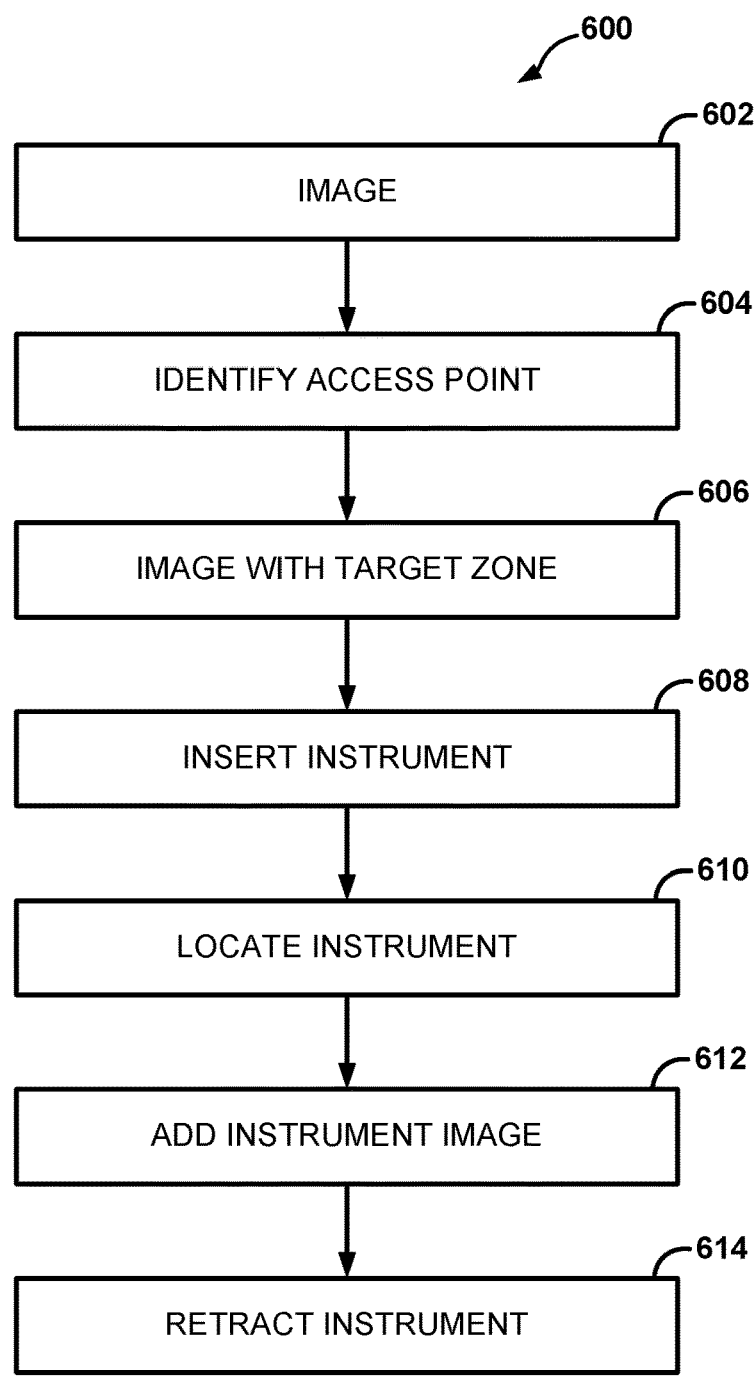
FIG. 10 is a flowchart of one example of a method of implanting a mitral valve utilizing the system of FIG. 3A or 3B.

In one or more examples, the system 10 may be utilized for implantation of a transcatheter mitral valve. For example, FIG. 10 is a flowchart of one example of a method 600 of implanting a transcatheter mitral valve utilizing system 10 in accordance with any of the examples described in this disclosure. Although described in reference to system 10 of FIGS. 3-6, the method 600 may be utilized with any suitable system. In one or more examples, the controller 204 may be adapted to utilize the method 600. A clinician may image the heart of the patient (602) using any suitable technique, e.g., echocardiography. In one or more examples, the LV apex and the mitral valve may be imaged and provided in a bi-plane view to the clinician. Controller 204 may identify an optimal access point near the apex (604), and the access point may provide a central, perpendicular trajectory of a catheter (e.g., or other medical instrument or medical device 130) through the mitral valve in both planes.

Image 300 may be presented with a target zone (606). For example, an access line or target path may be added to the image 300 and attached to one or more identified physiological landmarks such that the target path is registered with the landmark and moves along with the landmark in the image 300. An incision into the LV along the target path may be made, and an access sheath may be placed into the LV.

The catheter (or other medical instrument or medical device) may be inserted (608). The catheter (or other medical instrument or medical device) may be located (610) using any suitable technique or techniques. An augmented image of the catheter (or other medical instrument of medical device) may be added to the image 300, which may be presented on display device 206, (612) based upon detection by the EM tracking system of one or more sensors disposed on the catheter. The catheter may be guided through the valve, and practice steering motions may be performed to aid the clinician to understand how hand motion correlates to tip motion.

Figure 11:
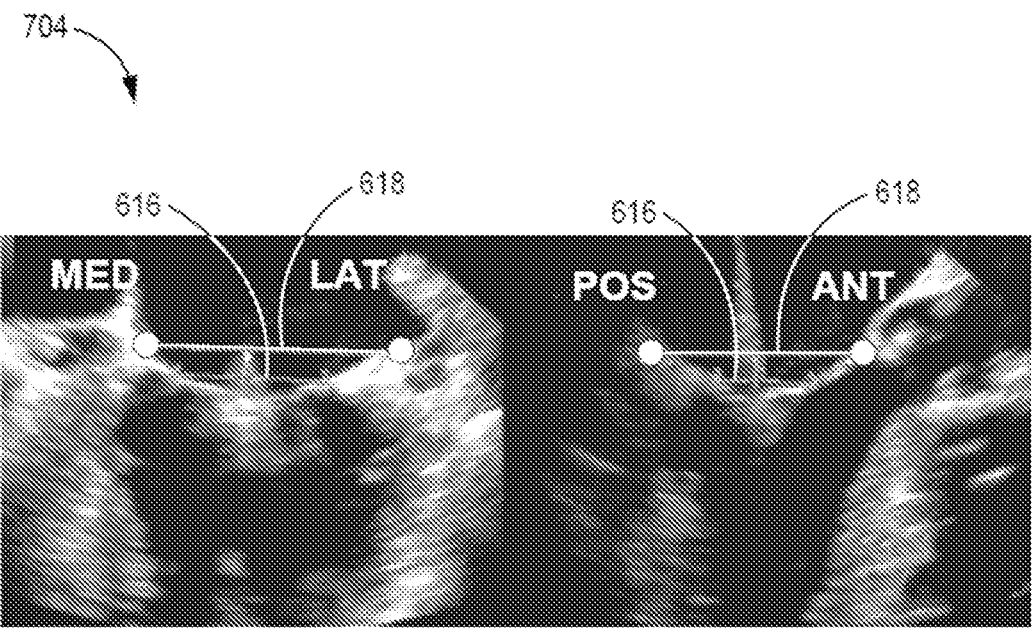
FIG. 11 is a schematic view of an ultrasound image of an area of interest in a patient's heart that includes an augmented mitral annulus line and a parallel target landing line or zone.

The clinician or the system 10 may draw one or more target lines on the image 300 that overlay the real-time echocardiography image. For example, a line parallel to a mitral annulus line (e.g., 6 mm above the mitral annulus line) may be provided in the image 300 to provide a target landing line or zone. For example, FIG. 11 is a schematic view of a display 704 that includes a medial-lateral (MED-LAT) and posterior-anterior (POS-ANT) ultrasound image with an augmented mitral annulus line 616 and a parallel target landing line 618 or zone. This target landing line 618 stays on the display 704 and dynamically moves with the surrounding anatomy once the echocardiography image goes live. Any suitable technique or techniques may be utilized to provide the target landing line, e.g., image recognition software or other soft tissue tracking techniques, machine learning, or AI. In one or more examples, target landing line 618 may change colors if the medical instrument or medical device 130 deviates from the desired trajectory or is disposed at the desired location.

In this example, a capsule of the catheter (or other instrument or medical device) may be retracted (614) to partially expose a replacement valve. The valve may be centered in the target area by the clinician while viewing the image 300 on display device 110 or 206. The catheter may be pulled back to place the valve in the target landing zone, and the valve may be deployed by completing retraction of the capsule. The catheter may be guided out of the patient's body through the middle of the replacement valve and into the access sheath with the use of the display device 110 or 206 at 614.

Systems and methods to alleviate problems associated with visual obstruction of anatomy of interest in ultrasound images due the presence of medical instruments or medical devices in a region of the patient being imaged may include systems and methods utilizing ultrasound reference images. In one or more examples, a controller, such as controller 204 of computing system 100 may overlay, underlay, merge or otherwise present one or more reference images of the target region of the patient with one or more live ultrasound images from the imaging system of the target region of the patient. The live ultrasound images may be obtained by an ultrasound imaging system in real-time, or substantially in real-time, and may also be referred to as live images. In one or more examples, the controller, such as controller 204, is adapted to overlay, underlay, merge or otherwise present the reference image with the current, i.e., live, image such that the reference image is dynamic with the live image. In other words, the reference image is overlaid, underlaid, merged or otherwise presented with the current, live image such that the reference image moves in registration with the live image in the display.

In some examples, the reference image(s) may be a motion picture that may be looped, for instance, when using the system for navigation in heart surgery, where the looped motion picture includes individual images or frames that may be matched with events, e.g., synchronized with cyclical activity such as, e.g., cardiac phase during the beating of the patient's heart. The reference image(s) may remain visible in the display even if one or more portions of the live image of the target region become obstructed or unavailable to the imaging system, e.g., due to shadowing or other artifacts.

With regard to navigating a medical instrument or medical device through a moving body structure, difficulties may arise in attempting to track such a medical instrument or medical device using known tracking technology as the medical instrument or medical device passes adjacent or through the moving body structure, and the virtual representation of the instrument or medical device may be offset from the corresponding anatomy when superimposed onto image data. Accordingly, it may be desirable to acquire image data and track the medical instrument or medical device in a synchronized manner with a reference image acquired prior to the medical instrument or medical device causing visual obstructions such as, e.g., shadowing or other artifacts. The reference image may be obtained, for example, prior to guiding a medical instrument or medical device into an imaging field of view or after the medical instrument or medical device is introduced into the patient but before the medical instrument or medical device causes visual obstruction in the ultrasound image data.

In some examples, a system may be configured to display a reference image and track the medical instrument or medical device in a synchronized manner with a live image, e.g., by synchronizing the reference image with events such as cardiac phases, using gating or synchronization techniques such as ECG gating or respiratory gating, and only displaying the appropriate reference image (from a plurality of reference images for different events) when the functions of the heart or lungs are at a specified event, such as in a specified portion or phase of their respective cycles. For example, an ultrasound imaging and guidance system may store multiple versions of a reference ultrasound images captured in time with particular events such as particular phases of the cardiac cycle (e.g., atrial systole, ventricular systole, atrial diastole, or ventricular diastole, or corresponding ECG events indicated by P wave, QRS complex, and T wave).

The multiple versions of reference ultrasound images may represent motion of an anatomical object of the region of the patient and, in some examples, may be considered part of a motion picture loop. The system may select and present the appropriate reference ultrasound image from storage for the current, live image, based on a match between the event to which the live image corresponds and the event associated with the respective reference image retrieved from storage. If the live image is captured during atrial systole, for example, then the system retrieves the stored reference image associated that was previously captured during atrial systole for the patient, and likewise retrieves the other reference images that correspond to other events associated with successive live images, promoting a better visual match between the reference image and the live image. Alternatively, a series of successive ultrasound reference images may be obtained over the full cycle of a moving anatomical structure, such as the full cardiac cycle of the heart, and be presented as a series of reference images, like a motion picture, with live ultrasound images during each cardiac cycle, e.g., without synchronizing with particular phases of the cardiac cycle.

An imaging and guidance system may store multiple reference images for different spatial orientations. A live image may have different orientations based on changes in the position of the patient or the position of the ultrasound transducer array. In some examples, an imaging and guidance system may be configured to obtain multiple reference images over a range of different spatial orientations and then retrieve from storage a selected one of the reference images that most closely corresponds to a spatial orientation of the current, live image, e.g., in terms of translation, rotation, perspective or other spatial characteristics. In some examples, using machine learning techniques, the system may identify features in the live image to quickly identify particular spatial orientations of the live images, and retrieve reference images corresponding to those spatial orientations. For example, the system may identify the annular plane of a cardiac valve in the live image or any sort of identifiable echogenic anatomical landmark that may be used as an anchor for the reference image. In some examples, the stored reference images may be obtained with different spatial orientations and during different events, such as different phases of cardiac activity. In this case, the system may retrieve reference images that correspond to both the spatial orientation and phase associated with the live image, again thereby promoting a better visual match.

Hence, in some examples, the reference ultrasound image includes a plurality of reference ultrasound images. In this case, one or more processors of an ultrasound imaging system or associated computing system may be configured to receive event data. For example, one or more processors of controller 204 may select one of the plurality of reference ultrasound images based on the event data. The event data may indicate an event associated with an anatomical object of the patient, such as cardiac phase data or other cyclical event data associated with a live ultrasound image. For example, the event data may relate to a cardiac cycle, and the selected reference ultrasound image may correspond to a phase of the cardiac cycle. Hence, the reference ultrasound images may be correlated with respective phases of the cardiac cycle.

In some examples, a cardiac phase may be sensed or predicted based on timing of the cardiac cycle. For example, one or more processors of controller 204 may be configured to determine the phase of the cardiac cycle based on an ECG signal. As one example, the ECG signal may be used to support ECG gating to select reference ultrasound images correlated with particular components of an ECG signal, and thereby synchronize the reference ultrasound images and live ultrasound images according to an ECG signal of the patient. Alternatively, or additionally, one or more processors of controller 204 may be configured to determine the phase of the cardiac cycle based on the reflected ultrasound energy or the live ultrasound image itself. The reflected ultrasound energy may include one or more characteristics, such as reflected energy levels or patterns, that indicate particular phases of cardiac activity. Additionally, or alternatively, the live ultrasound image data may be analyzed to sense movement or shapes that are correlated with particular phases of cardiac activity. In another example, during a procedure, the patient may receive active cardiac pacing, and reference images may be selected in response to phases or cycles of cardiac activity indicated by pacing pulses. In each case, reference ultrasound images may be selected for particular phases of cardiac activity.

In this example, one or more processors of controller 204 may be configured to select the reference ultrasound image based on a correspondence between the selected reference ultrasound image and the event, and control a display device, such as display device 206 or display device 110 to display the selected reference ultrasound image with at least portion of the live ultrasound image. In some examples, the selected ultrasound reference image may be displayed additionally, or alternatively, with a representation of a medical instrument or medical device guided with a region of the patient.

Additionally, or alternatively, a system may store multiple reference ultrasound images and select one of the reference ultrasound images based on one of a plurality of spatial orientations of the live ultrasound image, and control a display device to display the selected reference ultrasound image with the live ultrasound image or a representation of a medical instrument or medical device. Again, in some examples, each of the spatial orientations may include at least one of a particular translation, rotation, or perspective of the live ultrasound image. In some examples, one or more processors of controller 204 may receive both event data and spatial orientation data for a live image, select one of a plurality of reference ultrasound images based on both the event data and spatial orientation data, and present the selected reference ultrasound image with the live ultrasound image or a representation of a medical instrument or medical device.

In one or more examples, the present disclosure may provide a system for guiding a medical instrument or medical device through a region of a patient while identifying and tracking a region of anatomy of the patient during a medical procedure (e.g., an ablation procedure, a valve placement procedure, a lead placement procedure, an LVAD placement procedure, etc.). The system may include various imaging and tracking systems and a controller that incorporates machine learning to identify a region of a patient utilizing data from these imaging and tracking systems and that is adapted to generate an image that may include one or more markers representing one or more target zones to guide the clinician to the target region of interest of the patient. Once the target region of interest of the patient is identified based on the medical procedure and the use of machine learning, one or more markers (e.g., a marker signifying a point or a plane) may be placed in the image to represent the target or landing zone of interest for the medical procedure.

In one or more examples, a marker indicating the target region may also visually change when a medical instrument or medical device reaches the target zone (e.g., target zone changes color from red to green). This may be beneficial especially when the anatomy of interest is not visible. The one or more anatomical markers in the image may remain visible even if the target region of the patient becomes obstructed or unavailable to the ultrasound sensor collecting ultrasound image data, e.g., due to shadowing or other artifacts. The one or more anatomical markers in the image may be utilized as a target for the medical procedure as they are associated with the anatomy of interest that may or may not be visible to the imaging system throughout the entire procedure. Unlike the image of the anatomy of interest that may or may not remain visible in the image throughout the procedure, the one or more markers in the image may remain visible throughout the entire procedure.

In one or more examples, the present disclosure may provide a method for identifying and tracking target anatomy using one or more imaging systems, such as an ultrasound imaging system, during a medical procedure for therapy delivery (e.g., an ablation procedure, a valve placement procedure, a lead placement procedure, a stent placement procedure, an LVAD placement procedure, etc.). The method may use a controller that may be adapted to receive image data from one or more imaging systems and use machine learning to identify an anatomical region of interest of the patient based on the medical procedure to be performed. The method may include using machine learning to identify the anatomy of interest based on the procedure of interest. For example, data sets indicative of an anatomical region of interest for a certain procedure may be provided to one or more processors of controller 204 for analysis. The one or more processors of controller 204 may then learn to identify that anatomical region of interest.

For instance, the anatomical region of interest may be an aorta and the one or more processors of controller 204 may learn to identify the aorta in image data from an ultrasound system. Once the anatomy of interest is identified using machine learning or ultrasound, one or more markers (e.g., one or more point or plane markers) may be placed in the image by the controller to represent the target or landing zone of interest for the medical procedure. The one or more markers may represent the target or landing zone, which may be tracked in time and space and stay visible on the screen in the image, even if the actual anatomical image becomes obstructed or unavailable to the imaging system, e.g., due to shadowing or other artifacts. The one or more point or plane markers may become the target for the medical procedure or therapy delivery as they are associated with the anatomy of interest that may or may not be visible to the imaging system throughout the procedure.

In one or more examples, the present disclosure provides a system and method for storing an image of the anatomy of interest and displaying the image on a display device and overlaid with the live image even when the live image of one or more portions of the anatomy of interest becomes obstructed or unavailable. The method includes imaging a region of interest of the patient and saving the image data as reference data (e.g., echo images) taken prior to the instrument or medical device causing visual obstructions, such as shadows or other artifacts. In some examples, the reference image data may be taken, and stored, after the medical instrument or medical device, or a portion of the medical instrument or medical device, is introduced into the patient or into a region of interest of the patient, but before the medical instrument or medical device has been positioned to a point that the medical causes visual obstructions, such as shadows or other artifacts.

Once the imaging of the area of interest of the patient becomes obstructed or unavailable, the earlier reference (clean) image of the same area of interest of the patient may be overlaid, underlaid, merged or otherwise displayed by the controller, e.g., in a semi-transparent fashion, on the display device using one or more common anatomical reference points (e.g., the coronary sinus or the aorta) between the live image and the stored reference image, thereby anchoring the two images together. The selection of common anatomical regions or features between the two images may be accomplished using image recognition techniques or software or machine learning (e.g., utilizing image recognition/machine learning). The overlaying, underlaying or merging of the live image with the reference image may be facilitated in real time, allowing for a phantom image to be displayed during live echo imaging, e.g., via synchronization with timing or events, such as by ECG gating in the case of cardiac events, for example.

The system and method may allow both the anatomy and the medical instrument or medical device to be viewed on the display device simultaneously even if the live image of the anatomy becomes obstructed or unavailable. The system and method may allow both the anatomy of interest and the medical instrument or medical device to be viewed on the display device without causing interference between each other. In other words, this approach may allow for merging or fusion of the reference image with the live image, providing improved visualization of the anatomy even in the presence of shadowing or reflection effects due to the medical instrument or medical device. As discussed above, this reference image could be a plurality of reference images forming, in effect, a motion picture looped to match the heartbeat of a patient. For example, particular image frames of the motion picture data may correlate with portions or phases of the heartbeat cycle, e.g., with phases of an electrocardiogram, or with particular timing within the heartbeat cycle.

Further, in one or more examples, the system may be adapted to augment current echocardiography or other imaging techniques with targets, lines, markers, icons, or indicia to aid the clinician in implanting medical instruments or medical devices within a patient. For example, for implantation of a mechanical circulatory support (MCS) device, placement of a sewing ring on a left ventricle (LV) apex is desirable for proper positioning of an inflow cannula of the device. In one or more examples, it may be useful for the clinician to register the sewing ring used to attach the device to the heart with one or more images provided by an ultrasound system. When the surgeon holds the sewing ring against the LV, the ultrasound image may show the patient's beating heart in real time, and the controller may be configured to automatically calculate the inflow cannula angle based on where the sewing ring is held and display the trajectory of the inflow cannula on the ultrasound image.

In one or more examples, a feature may be displayed along with an augmented reality trajectory line to help interpret the data shown in the ultrasound image. For example, an augmented marker of one color, e.g., green, may be overlaid on the ultrasound image to show a desired positioning of the sewing ring. Further, an augmented marker of another color, e.g., red, may be overlaid on the ultrasound image to indicate that the sewing ring is not in the desired position. Once the sewing ring is in the desired position, the red augmented marker may transition to green.

In one or more examples, the image presented to the clinician may provide a roadmap for where to place medical instruments or medical devices. For example, an augmented echocardiographic image may include targets or lines disposed onto real-time echocardiographic images for use during a procedure to aid with appropriate implant techniques and alignment of implant tools and devices. A trajectory line for an implant cannula for the MCS device implantation may be overlaid onto a real-time image. Further, one or more physiological landmarks of the region of the patient may be marked in the image for transcatheter mitral valve implantation or location for a transseptal puncture for atrial fibrillation (AF) procedures. In one or more examples, the augmented image presented to the clinician may include augmented markers that highlight the anatomical or physiological landmarks within the target region of a patient.

In one or more examples, the augmented image provided to the clinician may include augmented markers that highlight the position, orientation, and trajectory of a medical instrument or medical device as the medical instrument or medical device is being utilized within the patient. One or more sensors may be disposed on the instrument or medical device such that the medical instrument or medical device may be tracked utilizing, e.g., an electromagnetic (EM) tracking system. Additionally, depending upon a cut plane of the echocardiographic image, the medical instrument or medical device may be visible in one or more views but not in others, and the medical instrument or medical device may be sliced/imaged through the middle of the shaft rather than the tip, causing confusion as to whether the tip is in a ventricle or an atrium. For example, if a view of the medical instrument or medical device is in a plane that cuts across a portion of the ventricle, the tip will appear to be there, but the tip may instead be in the atrium. By overlaying an augmented image of the medical instrument or medical device onto a real-time plane of ultrasound image data, the actual location of the medical instrument or medical device may be seen by the clinician.

The controller 204 of guidance workstation 50 or ultrasound workstation 150 may be configured to process a reference ultrasound image of the region of the patient, e.g., after the instrument or medical device is at least partially introduced into the patient, e.g., into an anatomical region of interest, but prior to the instrument or medical device causing obstructions in reflected ultrasound energy, or visual obstructions in ultrasound images formed based on the reflected ultrasound energy, register the reference ultrasound image with the physiological landmark, and overlay, underlay, merge or otherwise present the registered reference ultrasound image with the live image. Any suitable technique or techniques may be utilized to present the registered reference ultrasound image with the live image on a display device.

This registered reference image may be a moving picture that is looped, e.g., as described above. For example, ultrasound imager 140 or 142 may be configured to acquire reflected ultrasound energy from a beating heart, breathing lungs or other cyclically moving anatomical structure. Controller 204 of guidance workstation 50 or ultrasound workstation 150 may process the reflected ultrasound energy to create image data representing the moving anatomical structure. Successive frames of the ultrasound image data may be stored in memory 202. This ultrasound image data may be later output to display device 110 or 206, e.g., as a motion picture. The motion picture may be synchronized with cyclical activity of a moving anatomical structure, such as cardiac activity of a heart. In some examples, a controller 204 of guidance workstation 50 or ultrasound workstation 150 may be configured to select an ultrasound reference image from a plurality of reference ultrasound images, effectively forming a motion picture, based on correspondence to a current event, such as a current phase during cardiac cycle (e.g., atrial systole, ventricular systole, atrial diastole, or ventricular diastole, or corresponding ECG events indicated by P wave, QRS complex, and T wave). In this example, each ultrasound reference image "frame" in the series of images may be matched to a particular event and presented, e.g., at a time when that event is detected or expected. In some examples, the rate at which the series of reference images is presented like a motion picture may be changed to promote synchronization with the live ultrasound image.

As another example, the series of images may simply be matched to a full cycle of a moving anatomical structure, such as the heart. A clinician may select a portion or segment of the motion picture to store as a series of reference ultrasound images through user interface 218. Alternatively, controller 204, e.g., of guidance workstation 50 or ultrasound workstation 150, may be configured to detect the beginning and end of a full cycle of the moving anatomical structure in the reflected ultrasound energy or image data and to store a full cycle of image data in memory 202 as a series of reference ultrasound images. This series of reference images is, in effect, a motion picture of a full cycle of a cyclical moving anatomical structure. In this case, the reference images do not need to be synchronized with particular events such as phases of cardiac activity, but instead may be synchronized with full cycles of activity, such as full cardiac cycles.

If the length of a cycle varies between the time the reference images are obtained and a later time at which reference images are presented with live images, then the play time of the motion picture may be adjusted to match the change in the length of the cycle. Controller 204, e.g., of guidance workstation 50 or ultrasound workstation 150, could then register the reference image with the physiological landmark and synchronize and overlay, underlay, merge or otherwise present the reference image with the current, i.e., live, image data on display device 110 or 206, by outputting the stored successive frames continuously in synchronization with the real-time movement of the cyclical moving anatomical structure. So, as an example, for each full heartbeat cycle of the live image data, the series of reference images will run once and then restart at the next cycle of the live image data.

In one or more examples, one or more target landing lines or one or more physiological landmark markers may remain visible in the display device 110 or 206 even if the target region of the patient becomes obstructed or unavailable to the imaging system during the procedure. For example, image artifacts and shadowing of the anatomy due to reflection or obstruction of the ultrasound waves by the delivery catheter or the replacement valve may obstruct one or more portions of the target region of the patient to an ultrasound imaging system. In one or more examples, a controller 204, e.g., of guidance workstation 50 or ultrasound workstation 150, may overlay, underlay, merge or otherwise present one or more reference images of the target region of the patient, which were acquired prior to the procedure or prior to the medical instrument or medical device causing visual obstructions, for example, with one or more live images from an imaging system of the target region of the patient during the procedure. In one or more examples, the controller 204 may overlay, underlay, merge, or otherwise present, e.g., in a semi-transparent fashion, one or more reference images of the target region of the patient with one or more live images from the imaging system of the target region of the patient.

In one or more examples, controller 204 is adapted to overlay, underlay, merge or otherwise present the reference image with the live image such that the reference image of the anatomy dynamically moves with the live image of the anatomy. In other words, the reference image may be registered with the live image such that the reference image moves in registration with the live image in the display device 110 or 206. For example, the reference image may be a motion picture loop, as described above, containing a reference image for each phase of the heartbeat in synchronization with the phases of the actual heartbeat of the patient or with ECG events. Alternatively, the motion picture loop may be obtained for a full cardiac cycle and played for the duration of a cardiac cycle, and reset for each later cycle, such that synchronization with particular phases of a cycle may not be needed. The reference and live images may be overlaid, underlaid, merged, registered or otherwise presented together using one or more common anatomical reference points within each image.

The reference image may remain visible in the display device 110 or 206 even if one or more portions of the live image of the target region become obstructed or unavailable to the imaging system, e.g., due to obstruction in reflected ultrasound energy due to the presence of a medical instrument or medical device in a region of interest. In one or more examples, one or more target landing lines or one or more physiological landmark markers may remain visible in the display device 110 or 206 registered to the reference image even one or more portions of the target region of the patient becomes obstructed or unavailable to the imaging system during the procedure.

Figure 12:
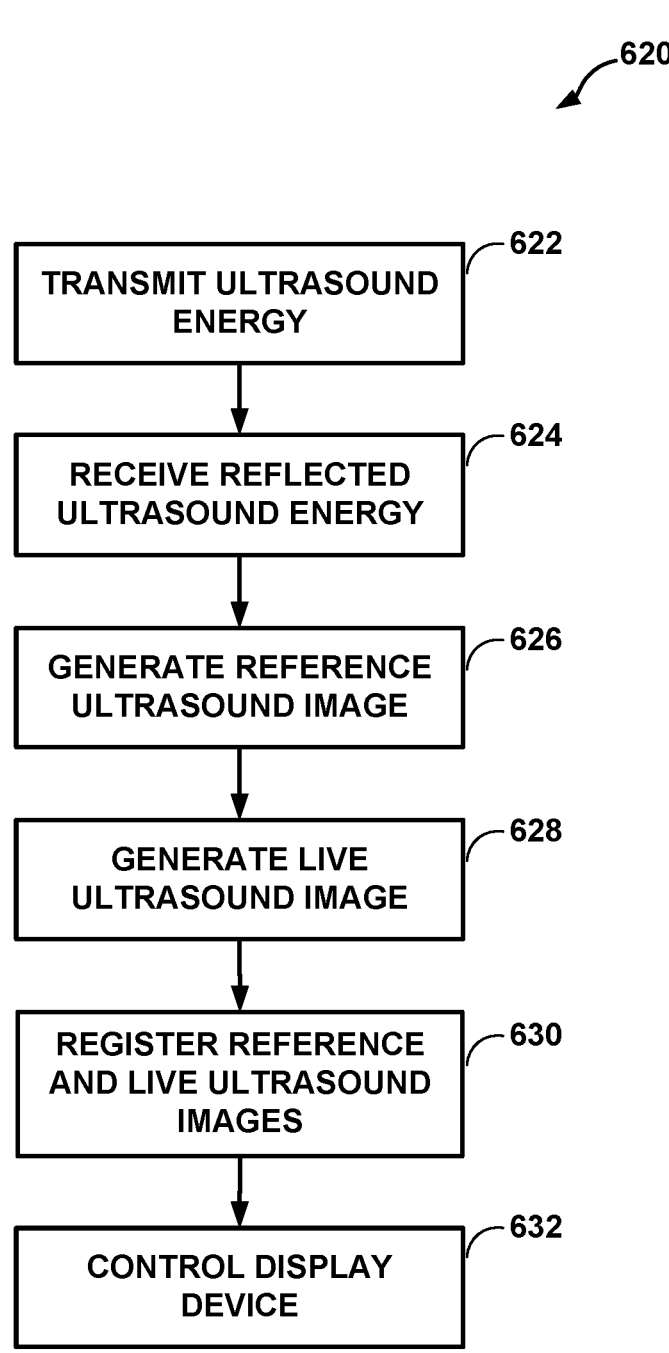
FIG. 12 is a flowchart of one example of presenting a reference ultrasound image and a live ultrasound image in registration.

FIG. 12 is a flowchart of one example of a method 620 of presenting a reference ultrasound image with a live ultrasound image in a method of guiding a medical instrument or medical device through a region of a patient utilizing system 10 of FIG. 3A or 3B, as described above. As shown in FIG. 12, system 10 may transmit ultrasound energy in a region of a patient (622). For example, one or more processors of controller 204 of guidance workstation 50 or ultrasound workstation 150 may control ultrasound imager 140 or 142 to transmit ultrasound energy. Ultrasound imager 140 or 142 may receive ultrasound energy reflected in the region of the patient (624). Ultrasound workstation 150 or guidance workstation 50 may generate a reference image based on the received reflected ultrasound energy (626) prior to a medical instrument or medical device causing obstruction in the received ultrasound energy. For example, ultrasound workstation 150 or guidance workstation 50 may generate a reference image prior to the medical instrument or medical device being introduced into the body of the patient. In another example, ultrasound workstation 150 or guidance workstation 50 may generate a reference image after the medical instrument or medical device is introduced into the body of the patient, but before the medical instrument or medical device enters the region of the patient. In yet another example, ultrasound workstation 150 or guidance workstation 50 may generate a reference image after the medical instrument or medical device enters the region of the patient but before the medical instrument or medical device causes obstruction in the received ultrasound energy. In some examples, ultrasound workstation 150 or guidance workstation 50 may generate multiple reference images. In some examples, ultrasound workstation 150 or guidance workstation 50 may generate a reference image of a full cycle of a moving anatomical structure, e.g., as multiple reference images synchronized, i.e., time or event-matched, with a series of respective events in the cycle. In some examples, ultrasound workstation 150 or guidance workstation 50 may generate a reference image that is a motion picture loop.

Ultrasound workstation 150 or guidance workstation 50 may generate a live ultrasound image of a region of the patient (628). For example, controller 204 of ultrasound workstation 150 or guidance workstation 50 may generate an ultrasound image of a region of the patient in real-time. Ultrasound workstation 150 or guidance workstation 50 may the register the reference ultrasound image and the live ultrasound image (630). For example, controller 204 of ultrasound workstation 150 or guidance workstation 50 may register the reference ultrasound image and the live ultrasound image based on one or more anatomical landmarks in the images as discussed further with respect to FIGS. 13-15. Controller 204 may control display device 110 or display device 206 to display the registered reference ultrasound image and the registered live image overlaid, underlaid, merged or otherwise presented (632).

Figure 13:
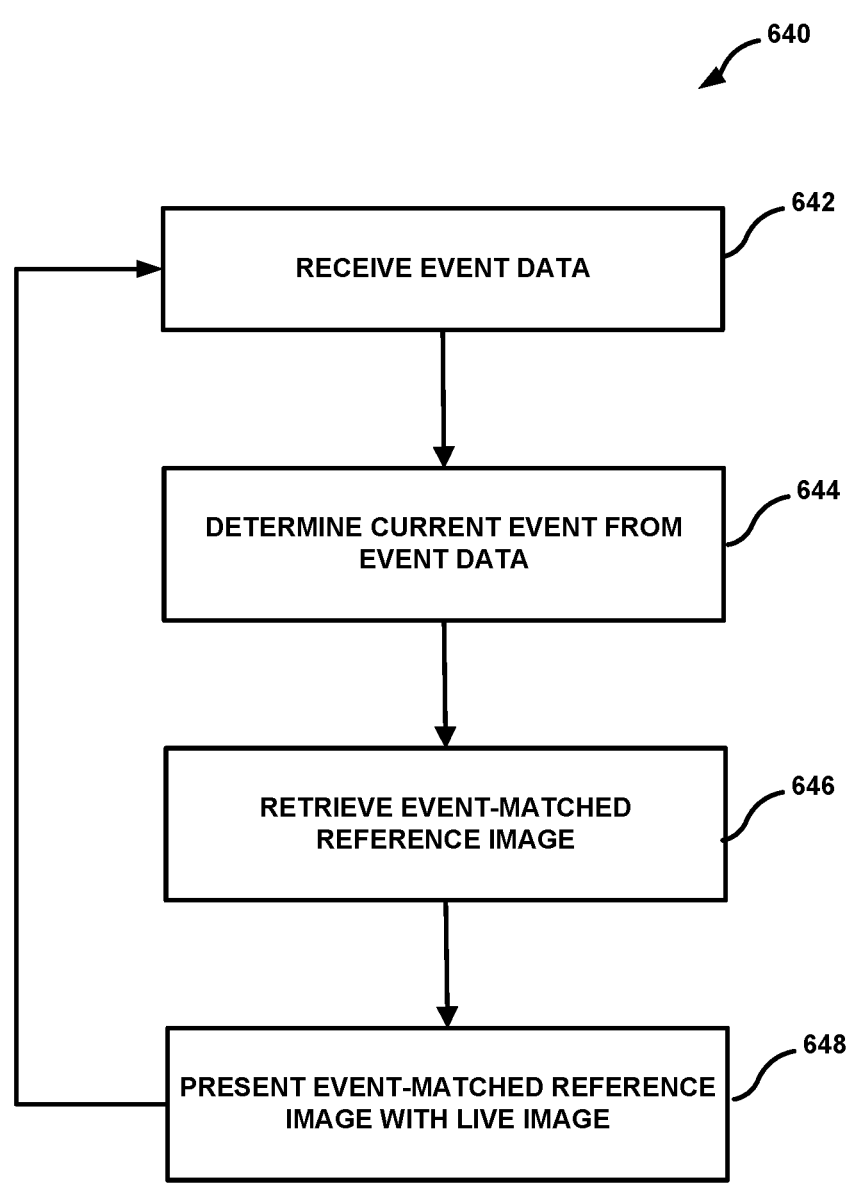
FIG. 13 is a flowchart of one example of a method of presenting an event-matched reference ultrasound image with a live ultrasound image in a method of guiding a medical instrument or medical device through a region of a patient utilizing the system of FIG. 3A or 3B.

FIG. 13 illustrates a method of presenting an event-matched reference ultrasound image with a live ultrasound image (640) for guiding a medical instrument or medical device through a region of a patient utilizing the system of FIG. 3A or 3B. The method, e.g., as performed by one or more processors of controller 204 of system 10 such as controller 204 of guidance workstation 50 or ultrasound workstation 150, may include receiving event data (642), determining a current event from the event data (644), retrieving an event-matched reference ultrasound image (646) and presenting the retrieved (event-matched) reference ultrasound image with a current, live ultrasound image (648).

Again, the reference ultrasound image may be an ultrasound image, or one of a plurality of ultrasound images, obtained at a time when the medical instrument or medical device was not causing obstruction in received ultrasound energy. For example, the reference ultrasound image may be obtained by system 10 prior to the medical instrument or medical device causing obstruction, including prior to the medical instrument or medical device being positioned within an imaged region of the patient, or after the medical instrument or medical device is positioned, at least partially in the imaged region, but before the medical instrument or medical device caused obstruction in the received ultrasound energy.

The event data may include a sensed, expected, or predicted event, or receipt of a control signal, indicating a particular event, such as a particular phase in a cycle of a moving anatomical structure, such as a phase in the cardiac cycle of a patient's heart or a component of an ECG signal, such as a P wave, QRS complex, or T wave. One or more processors of controller 204 may obtain and store multiple reference ultrasound images obtained at different phases of a cardiac cycle. For example, system 10 may store multiple versions of a reference ultrasound images captured in time with particular events such as particular phases of the cardiac cycle (e.g., atrial systole, ventricular systole, atrial diastole, or ventricular diastole, or corresponding ECG events indicated by P wave, QRS complex, and T wave).

Alternatively, rather than presenting reference frames for each cardiac phase or ECG component, a series of successive ultrasound reference images may be obtained over the full cardiac cycle, e.g., as a motion loop of reference images. The reference ultrasound images then may be played, like a motion picture, with live ultrasound images over ensuing cardiac cycles, resetting for replay of the loop at the start of each cardiac cycle. The motion loop, obtained for a full cardiac cycle, may be started with each cardiac cycle and played for the duration of the cardiac cycle.

In another example, during a procedure, the patient may receive active cardiac pacing, and reference images may be selected in response to phases or cycles of cardiac activity indicated by pacing pulses. For example, controller 204, e.g., of guidance workstation 50 or ultrasound workstation 150, may receive information indicating pacing of the patient, such as a clock signal or an explicit signal that a pacing pulse is being delivered, and, based on the pacing information, select particular reference images from memory or start or restart the display of a motion loop of reference images at the start of each cardiac cycle, as indicated by the pacing pulse information. In this example, a motion picture loop may be obtained for a full cardiac cycle and played for the duration of a cardiac cycle, e.g., in synchronization with the active pacing information.

By retrieving reference images corresponding to particular events, such as cardiac phases, system 10 may be configured to display each reference image, and track the medical instrument or medical device, in a synchronized manner with the live image. The selected reference image and live image may be registered, e.g., by controller 204 of guidance workstation 50, based on one or more anatomical landmarks in the images. Controller 204 may register the selected, event-matched reference image and the live image, e.g., based on one or more anatomical landmarks in the images, and present the reference image overlaid, underlaid, merged or otherwise presented in registration with the live image. For example, controller 204 may include a graphics processing unit (GPU) and may create a composite image by layering one of the reference image and the live image over the other. Selecting a reference image based on a cardiac phase may promote a better visual match between the reference image and the live image.

In some examples, cardiac phases may be sensed or predicted based on timing of the cardiac cycles, and corresponding reference frames may be retrieved from memory for presentation with live images. Alternatively, or additionally, one or more processors of controller 204 may be configured to determine the phase of the cardiac cycle based on analysis of one or more characteristics of reflected ultrasound energy or live ultrasound images that indicate particular phases. In each case, the detected cardiac phases may serve as events for selection of corresponding reference images from storage.

Figure 14:
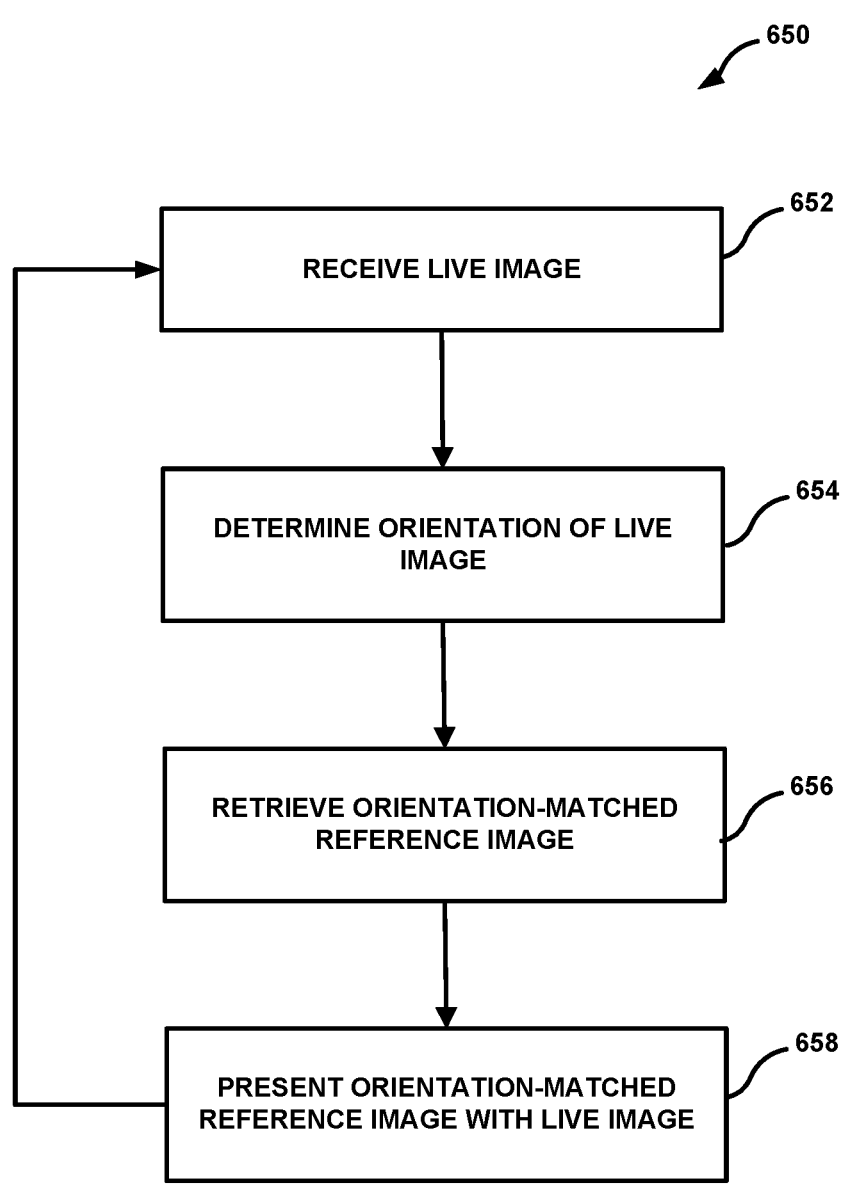
FIG. 14 is a flowchart of one example of a method of presenting an orientation-matched reference image with a current image in a method of guiding a medical instrument or medical device through a region of a patient utilizing the system of FIG. 3A or 3B.

FIG. 14 is a flowchart of one example of a method 650 of presenting an orientation-matched reference image with a current image in a method of guiding a medical instrument or medical device through a region of a patient utilizing system 10 of FIG. 3A or 3B, as described above. As shown in FIG. 14, in method 422, controller 204, e.g., of guidance workstation 50 or ultrasound workstation 150, receives a current, live ultrasound image (652), determines a spatial orientation of the live ultrasound image (654), retrieves one of a plurality of reference ultrasound images that corresponds to the determined spatial orientation of the live image (656), and presents the retrieved, orientation-matched, reference ultrasound image with the live image on display device 206 or display device 110 (658). Selecting a reference image based on orientation may promote a better visual match between the reference image and the live image.

In this example, system 10 obtains and stores multiple reference images obtained for a range of different spatial orientations of ultrasound imager 140, ultrasound imager 142, or the patient. Using machine learning, based on the orientation of one or more anatomical landmarks, such as the annular plane of a cardiac valve or any sort of identifiable echogenic anatomical landmark, within the reference ultrasound images and live images, controller 204 may select, for presentation with the live image, one of the stored reference images that most closely corresponds to the orientation of the live image. For example, reference images could be collected by a clinician at a known position. In the case of imaging a heart of a patient, the clinician may collect a four chamber view of the heart, a two chamber view of the heart and/or a three chamber view of the heart. If obstruction appears in the live image, controller 204 may select an appropriate reference image to present with the live image. In some examples, the orientation may be determined based on at least one of translation, rotation, perspective of the images. Controller 204 may register the selected reference image and the live image, e.g., based on one or more anatomical landmarks in the image (e.g., the coronary sinus, aorta, left atrial appendage or mitral leaflet insertion points if the heart is being imaged), and present the reference image overlaid, underlaid, merged or otherwise presented in registration with the live image.

Figure 15:
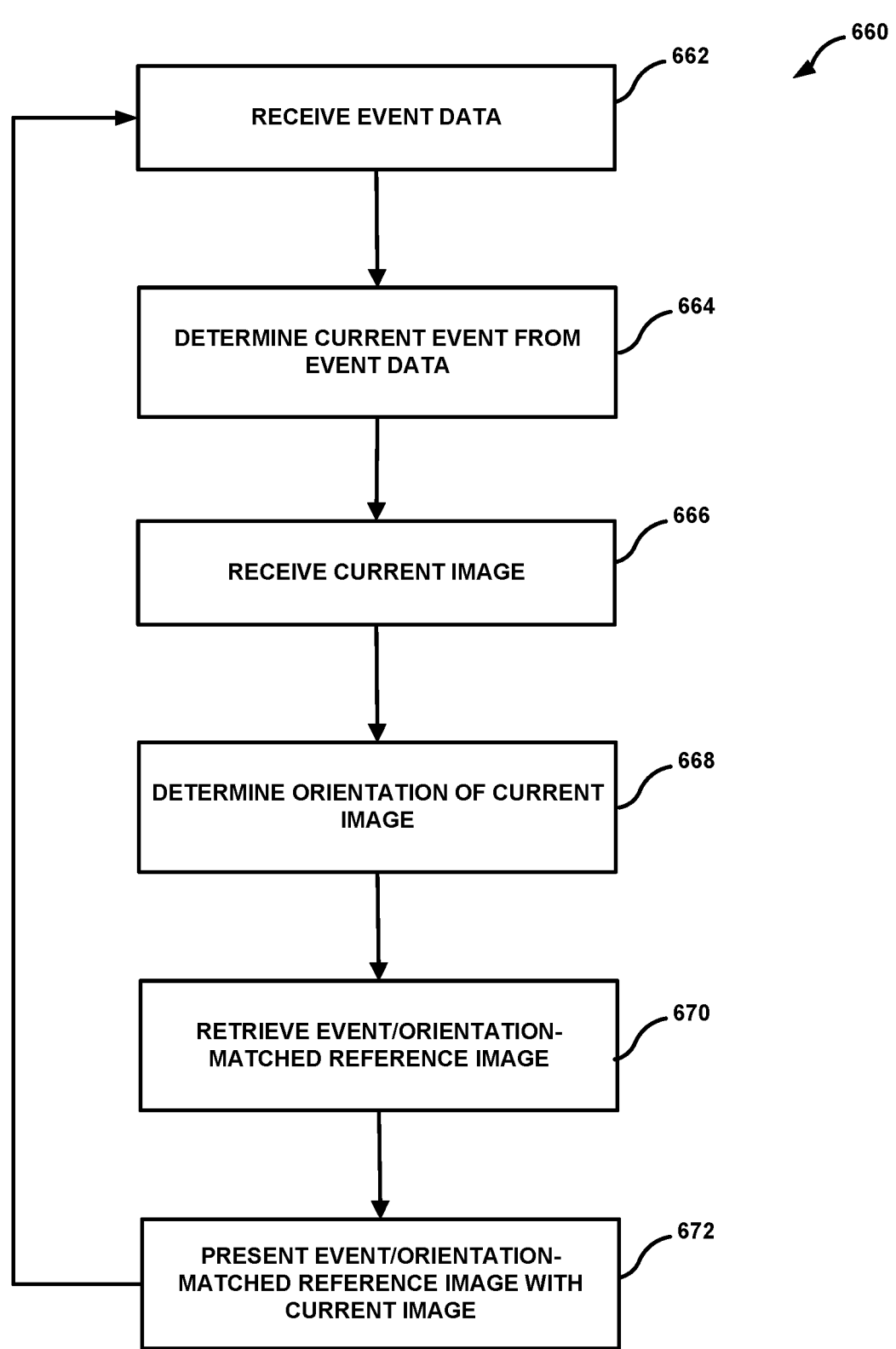
FIG. 15 is a flowchart of one example of a method of presenting an event and orientation-matched reference image with a current image in a method of guiding a medical instrument or medical device through a region of a patient utilizing the system of FIG. 3A or 3B.

FIG. 15 is a flowchart of one example of a method 660 of presenting an event- and orientation-matched reference image with a current image in a method of guiding a medical instrument or medical device through a region of a patient utilizing system 10 of FIG. 3A or 3B, as described above. In this example, method 432 includes receiving event data (662), and determining a current event from the event data (664), such as a cardiac phase or ECG component in one example. The method 432 also includes receiving a current, live image (666) and determining an orientation of the current, live image (668). As further shown in FIG. 15, the method 432 includes retrieving from storage a reference ultrasound image that corresponds to both the event indicated by the event data and the orientation of the live image, i.e., an event/orientation-matched reference image (670), and presenting the retrieved event/orientation-matched reference ultrasound image with the current, live image (672). Hence, method 660, in effect, combines aspects of method 640 of FIG. 13 and method 650 of FIG. 14.

In some examples, system 10 may be configured to obtain multiple reference ultrasound images prior to a point at which the medical instrument or medical or device is producing visual obstruction in the ultrasound image. For example, system 10 may receive user input indicating that system 10 should collect multiple reference ultrasound images, e.g., synchronized with multiple events such as cardiac phases, ECG events or the like, or synchronized with multiple image spatial orientations. In this manner, system 10 may collect and store reference images matched to events, orientations or both. It may be desirable to collect at least enough reference images to fill a full cardiac cycle or match with a set of cardiac phases or ECG events. Likewise, it may be desirable to collect a number of reference images sufficient to match with a desired set of spatial orientations. The collection of multiple reference images may proceed for a period of time that may be controlled by the clinician. However, system 10 may stop collecting reference images upon detection of obstruction caused by a medical instrument or medical device in the region of interest.

FIGS. 16A-16F are block diagrams of examples of an ultrasound probe for use in system 10 to produce ultrasound images for guidance of a medical instrument or medical device within a region of a patient while avoiding or reducing the effects of obstruction, such as shadowing, caused by presence of the medical instrument or device within the region. It should be noted that the ultrasound probes shown in FIGS. 16A-16F may be used as ultrasound imager 140 of FIG. 3A or ultrasound imager 142 of FIG. 3B, or may be part of ultrasound imager 140 or 142. Each of the ultrasound probes in FIGS. 16A-16F includes an ultrasound transducer array, such as ultrasound transducer array 144 of FIG. 3B. While each of FIGS. 16A-16F shows ultrasound transducer elements in linear or matrix array arrangements, the ultrasound transducer elements could be arranged in other ways, such as in a curvilinear array. Ultrasound transducer arrays shown in FIGS. 16A-16F may be configured and or controlled such that ultrasound energy transmitted from the probe or reflected ultrasound energy received by the probe may be oriented in a manner to avoid or mitigate obstruction caused by reflection of ultrasonic energy due to presence of a medical instrument or medical device in the region of the patient.

Figure 16A:
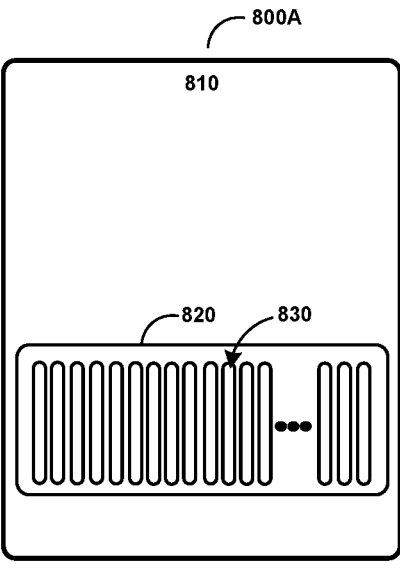
FIG. 16A is a block diagram of one example of an ultrasound probe with an ultrasound transducer array which may be used in the system of FIG. 3A or 3B.

FIG. 16A is a block diagram of one example of an ultrasound probe 800A with an ultrasound transducer array 820 which may be used in the system of FIG. 3A or 3B. In the example of FIG. 16A, an ultrasound probe 800A comprises a housing 810 and an ultrasound transducer array 820 including an array of transducer elements 830. Transducer array 820 forms a linear array of transducer elements 830 extending in one dimension. In some examples, the array of transducer elements may be arranged in a curvilinear array or other fashion. Transducer elements 830 may be evenly spaced and may include any number of transducer elements. Ultrasound transducer array 820 may be generally disposed at the distal end of ultrasound probe 800A, which may form part of an ultrasound imager such as ultrasound imager 140 or 142 of FIGS. 3A and 3B, respectively. In some examples, ultrasound probe 800A may be disposed at a distal end of a catheter such as a transesophageal echocardiography (TEE) catheter. Accordingly, in some examples, ultrasound probe 800A may be sized and configured for use within a human body and, particularly, within a lumen of the human body such as the esophagus. Transducer elements 830 of transducer array 820 are operable to emit ultrasound energy when receiving an excitation signal from, for example, controller 204 of ultrasound workstation 150 or guidance workstation 50, e.g., via associated driver circuitry, and are operable to receive reflected ultrasound energy created by reflections from the ultrasound energy and to transmit data associated with the reflected ultrasound energy to, for example, guidance workstation 50 or ultrasound workstation 150, e.g., via associated sense circuitry.

Figure 16B:
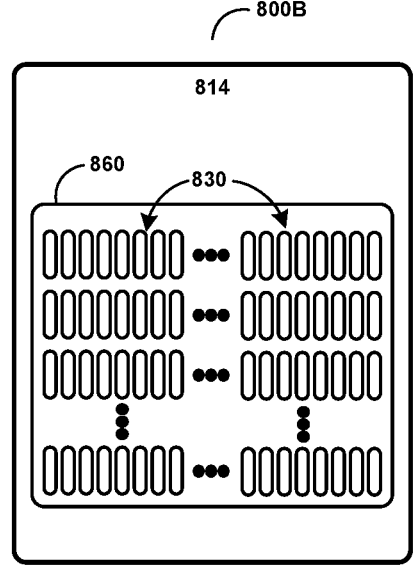
FIG. 16B is a block diagram of another example of an ultrasound probe with a two-dimensional transducer array which may be used in the system of FIG. 3A or 3B.

FIG. 16B is a block diagram of another example of an ultrasound probe 800B with a two-dimensional transducer array 860 which may be used in system 10A or 10B of FIG. 3A or 3B. In FIG. 16B, ultrasound probe 800B comprises a housing 814 and may substantially conform to the description of probe 800A of FIG. 16A, in structure and function, except that, instead of using transducer elements 830 in a single linear transducer array (or curvilinear) as in FIG. 16A, probe 800B provides a plurality of ultrasound transducer elements 830 arranged in two-dimensional array 860. In the example of FIG. 16B, transducer elements 830 in two-dimensional array 860 are arranged in rows and columns extending in an azimuth direction and elevation direction, respectively. Other arrangements may also exist. As in the example of FIG. 16A, the plurality of ultrasound transducer elements 830 in array 860 of FIG. 16B are operable to emit ultrasound energy when receiving an excitation signal from, for example, controller 204 of ultrasound workstation 150 or guidance workstation 50, and are operable to receive reflected ultrasound energy created by reflections from the ultrasound energy and to transmit data representative of the reflected ultrasound energy to, for example, controller 204 of ultrasound workstation 150 or guidance workstation 50.

In FIG. 16B, the plurality of ultrasound transducer elements 830 is shown as arranged in a box-like matrix. This represents just one of many possible implementations as the plurality of transducer elements 830 may be arranged in other manners, for example, to provide various types of multi-dimensional arrays. This plurality of ultrasound transducer elements 830 in array 860 may comprise any number N×M of ultrasound transducer elements, where N designates a number of transducer elements in a row and M designates a number of transducer elements in a column, and where N and M may the same or different. As one non-limiting example, each row or column of transducer array 820 could have at least N=32 transducer elements 830 and, in some cases, at least N=64 transducer elements or at least N=128 transducer elements. Any number of the plurality of ultrasound transducer elements 830 could be active at a given time, including all of them and the plurality of ultrasound transducer elements 830 could be configured in a single array or a plurality of subsets of transducer elements 830.

Another example of an ultrasound system and method that may alleviate problems associated with visual obstruction of anatomy of interest in ultrasound images due the presence of medical instruments or medical devices in a region of the patient being imaged may be an ultrasound probe having a split-aperture mode. For example, an ultrasound system may be configured to control an ultrasound transducer array to transmit a first ultrasound energy in a first direction and transmit second ultrasound energy in a second direction, different than the first direction, e.g., so as to avoid or mitigate the obstruction, such as shadowing, caused by echoes from the medical instrument or medical device. In some examples, the system may select a first subset of transducer elements in the transducer array and control the selected first subset of transducer elements to steer transmitted pulses of first ultrasonic energy in a first direction. In addition, the system may select a second subset of transducer elements in the transducer array and control the selected second subset of transducer elements to steer transmitted pulses of second ultrasonic energy in a second direction. The ultrasound imaging system may control the ultrasound transducer array to receive first reflected ultrasound energy in a first field of view of a region of patient anatomy based at least in part on reflection of the first ultrasound energy and receive second reflected ultrasound energy in a second field of view of the region of patient anatomy based at least in part on reflection of the second ultrasound energy. The first field of view and the second field of view may be determined to direct the first ultrasound energy and the second ultrasound energy in directions such that the first ultrasound energy and the second ultrasound energy do not hit or substantially do not hit the medical instrument or medical device so as to avoid or mitigate obstruction in the first reflected ultrasound energy and the second reflected ultrasound energy.

The second field of view is different than the first field of view. In some examples, the first field of view may be selected to include a first portion of the region of the patient anatomy on a first side of a medical instrument or medical device and the second field of view may be selected to include a second portion of the region of the patient anatomy on a second side of the medical instrument or medical device. In some examples, the second side of the medical instrument or medical device may be opposite the first side of the medical instrument or medical device. In other examples, the second side of the medical instrument or medical device may not be opposite the first side of the medical instrument or medical device. In this manner, the ultrasound imaging system may provide a split aperture having two different sections that produce two ultrasound images on different sides of a medical instrument or medical device. For example, the different fields of view may be on opposite sides of the medical instrument or medical device. In some examples, they may be on the medial and lateral sides, the anterior and posterior sides or both relative to a patient's body. In the case of mitral valve repair or replacement, for example, the ultrasound images may be obtained from different fields of view on different sides of a catheter introduced into the heart to repair a mitral valve or deliver a mitral valve prosthetic. For example, the catheter may have a distal end section and a proximal end section with a central, longitudinal axis therebetween. The first field of view and the second field of view may be different regions extending along different sides of the longitudinal axis of the catheter. In some examples, the different fields of view are approximately 180 degrees apart. In other examples, the different fields of view are not approximately 180 degrees apart. The ultrasound imaging system processes the first reflected ultrasound energy and the second reflected ultrasound energy in first and second fields of view, respectively, to generate one or more ultrasound images that may be used for guidance of the medical instrument or medical device.

In some examples, the first field of view and the second field of view may be any combination of left or right (e.g., along the medial-lateral axis or 0 degrees or 180 degrees) or top or bottom (e.g., along the posterior-anterior axis or 90 degrees or 270 degrees) with respect to the longitudinal axis of the medical instrument or medical device when displaying a two-dimensional image such as a medial-lateral view or a posterior-anterior view of the region of the patient. In other examples, the first field of view and the second field of view may be any combination of locations between left or right (not along the medial-lateral axis or not at 0 degrees or 180 degrees) or top or bottom (not along the posterior-anterior axis or not at 90 degrees or 270 degrees) with respect to the longitudinal axis of the medical instrument or device when displaying a two-dimensional image such as a medial-lateral view or a posterior-anterior view of the region of the patient.

One or more processors of controller 204 100 may control the ultrasound energy generated by the ultrasound transducer array, such as ultrasound transducer array 860, to provide beam steering. For example, the one or more processors of controller 204 may control at least one ultrasound transducer array, e.g., by controlling a phased array of transducer elements, to steer transmitted ultrasound energy in selected directions. In some examples, the one or more processors of controller 204 may control selected subsets of transducer elements in a single transducer array, such as ultrasound transducer array 860, to steer transmitted ultrasound energy in first and second directions and control selected subsets of transducer elements in the single transducer array, such as ultrasound transducer array 860, to focus received ultrasound energy in first and second fields of view, respectively. In this example, the selected subsets of transducer elements may form separate apertures of the ultrasound transducer array.

As an alternative, the ultrasound transducer array may include first and second transducer arrays that are separate from one another and are separately controlled to steer transmitted ultrasound energy in first and second directions, respectively, and receive ultrasound energy in first and second fields of view, respectively. In either case, the system may obtain ultrasound images from different sides of a medical instrument or medical device, in areas selected to avoid or reduce visual obstructions in reflected ultrasound energy, such as shadowing, that may obscure an anatomical region of interest in an ultrasound image formed by the ultrasound imaging system based on received ultrasound energy.

For example, the one or more processors of controller 204 may rearrange which ultrasound transducer elements are used as part of a first subset of ultrasound transducer elements or a second subset of ultrasound transducer elements in order to steer first and second beams of the transmitted ultrasound energy. In other examples, the ultrasound imaging system may control physically separate ultrasound transducer arrays to generate first and second beams, as discussed above. In some examples, the one or more processors of controller 204 may be configured to detect when the medical instrument or medical device is causing visual obstruction, and based on detection of obstruction, transition from a regular imaging mode, e.g., with a single beam or aperture and single field of view, to a split aperture mode with two beams or apertures and two fields of view encompassing regions on different sides of a medical instrument or medical device within a region of interest, or to a wide angle mode with one wider beam with reduced depth and a field of view that encompasses different sides of a medical instrument or medical device within the region of interest.

For example, one or more processors of controller 204, e.g., of guidance workstation 50 or ultrasound workstation 150, may be configured to control an ultrasound transducer array of any of the probes of FIGS. 16A-16F to transmit first ultrasound energy in a first direction and transmit second ultrasound energy in a second direction different than the first direction. The first direction and the second direction may be determined to direct the first ultrasound energy and the second ultrasound energy in directions such that the first ultrasound energy and the second ultrasound energy do not hit or substantially do not hit the medical instrument or medical device so as to avoid or mitigate obstruction in the first reflected ultrasound energy and the second reflected ultrasound energy.

The ultrasound transducer array may be a single transducer array with subsets of transducer elements, such as first and second subsets of transducer elements, that are controlled by controller 204 to transmit the first and second ultrasound energy, respectively. The subsets of transducer elements may be dynamically selectable, including the positions of the transducer elements along the array and the number and particular transducer elements to be activated in each subset. As an alternative to subsets of the same ultrasound transducer array, the ultrasound transducer array may, in some examples, comprise a first transducer array to transmit the first ultrasound energy and a second transducer array, separate from the first transducer array, to transmit the second ultrasound energy.

One or more processors of controller 204 also may control the ultrasound transducer array of any of the probes in FIGS. 16A-16F to receive first reflected ultrasound data in a first field of view of a region of patient anatomy based at least in part on reflection of the first transmitted ultrasound energy and receive second reflected ultrasound energy in a second field of view of the region of patient anatomy based at least in part on reflection of the second transmitted ultrasound energy. The second field of view is different than the first field of view. Again, the ultrasound transducer array may be a single transducer array with subsets of transducer elements, such as first and second subsets of transducer elements, that are controlled to receive the first and second reflected ultrasound energy, respectively. Alternatively, the ultrasound transducer array may comprise a first transducer array to receive the first ultrasound energy and a second transducer array, separate from the first transducer array, to receive the second ultrasound energy.

In some examples, the first field of view and the second field of view may be any combination of left or right (e.g., along the medial-lateral axis or 0 degrees or 180 degrees) or top or bottom (e.g., along the posterior-anterior axis or 90 degrees or 270 degrees) with respect to the longitudinal axis of the medical instrument or medical device when displaying a two-dimensional image. In other examples, the first field of view and the second field of view may be any combination of locations between left or right (not along the medial-lateral axis or not at 0 degrees or 180 degrees) or top or bottom (not along the posterior-anterior axis or not at 90 degrees or 270 degrees) with respect to the longitudinal axis of the medical instrument or device when displaying a two-dimensional image.

Transducer elements used to transmit the first ultrasound energy, whether provided as a subset of transducer elements in a single transducer array or in one of two separate transducer arrays, may be the same as or different than the transducer elements used to receive the first reflected ultrasound energy. Likewise, transducer elements used to transmit the second ultrasound energy, whether provided as a subset of transducer elements in single transducer array or one of two separate transducer arrays, may be the same as or different than the transducer elements used to receive the second reflected ultrasound energy. In some examples, transducer elements used for transmission and reception may be identical, or be partially overlapping with some transducer elements used for both transmission and reception and some transducer elements used only for transmission and some transducer elements used only for reception, or be mutually exclusive with transducer elements used for transmission and not used for reception and vice versa.

Controller 204, e.g., of guidance workstation 50 or ultrasound workstation 150, may provide excitation signals to the ultrasound transducer array to cause the array to transmit the ultrasound energy, and may include any appropriate electronic circuitry to drive the transducer elements in the array to transmit ultrasound energy and sense ultrasound energy received by the transducer elements in the array. Hence, in some examples, one or more processors of controller 204 may control transducer elements for transmission and reception of ultrasound energy via electronic circuitry. The one or more processors of controller 204 are configured to generate one or more ultrasound images based on the first and second reflected ultrasound energy for output to, and presentation by, display device 110 or 206.

In some examples, controller 204 may control transducer elements to transmit third ultrasound energy in a third direction different than the first and second directions and receive third reflected ultrasound energy in a third field of view different than the first and second fields of view. The controller 204 also may be configured to determine that a medical instrument or medical device is causing or is about to cause obstructions in reflected ultrasound energy received by the ultrasound transducer array, and steer the transmitted ultrasound energy or focus the received ultrasound energy so as to avoid or mitigate the effects of the visual obstructions. In one example, the controller 204 may control the transducer array to cease transmitting ultrasound energy in the third direction and cease receiving third reflected ultrasound energy. Controller 204 may control the transducer array to begin transmitting ultrasound energy in the first and second directions and begin receiving first reflected ultrasound energy and second reflected ultrasound energy. As examples, controller 204 may accomplish the steering by mechanically steering the array, or controlling a phased array of transducer elements to steer a beam of transmitted ultrasound energy, and controlling transducer elements to focus reflected ultrasound energy received by the array in a field of view.

Referring back to FIG. 16A, one or more processors of controller 204 may control first and second subsets of transducer elements 830 in transducer array 820 to provide a split aperture imaging mode such that the first and second subsets operate as sub-arrays to separately transmit first and second ultrasound energy and separately receive first and second reflected ultrasound energy. Subsets of transducer elements 830 may transmit the first and second ultrasound energy, e.g., pulses of ultrasound energy, simultaneously or substantially simultaneously (e.g., at the same point in time or within less than one second). Likewise, subsets of transducer elements 830 may receive first and second reflected ultrasound energy simultaneously or substantially simultaneously.

In some examples, the subsets of transducer elements 830 may be selected such that a gap exists between the subsets. The subsets of transducer elements 830 may transmit ultrasound energy and receive reflected ultrasound energy in different fields of view, e.g., as a function of the gap between the transducer subsets, beam steering and focusing of ultrasound energy transmitted or received by the subsets, or both.

Each of the subsets of transducer elements 830 may be independently steerable, e.g., by one or more processors of controller 204, to steer and focus the ultrasound energy. With a split aperture for providing first and second beams of ultrasound energy and first and second fields of view for reflected ultrasound energy, the respective apertures may be reduced in size. When providing reduced imaging apertures in the split aperture design, in some examples, the subsets of transducer elements 830 of transducer array 820 of ultrasound probe 800A may be operated at higher frequencies to compensate for reduced imaging resolution.

Figure 16C:
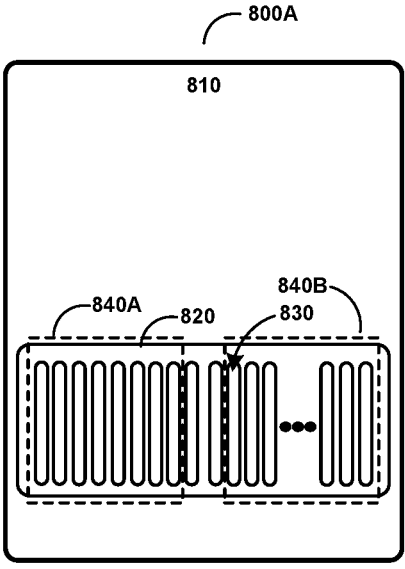
FIG. 16C is a block diagram of another example of an ultrasound probe with an ultrasound transducer array which may be used in the system of FIG. 3A or 3B, illustrating selection of transducer subsets.

FIG. 16C further illustrates the selection of subsets of transducer elements 830 in transducer array 820 of probe 800A to support a split aperture imaging mode, as discussed above with reference to FIG. 16A. As shown in FIG. 16C, transducer array 820 forms a linear array of transducer elements 830 extending in one dimension. In some examples, the array of transducer elements may be arranged in a curvilinear array or other fashion. In FIG. 16C, transducer elements 830 of transducer array 820 are divided into first and second transducer subsets 840A and 840B. In some examples, controller 204 e.g., of guidance workstation 50 or ultrasound workstation 150, may flexibly and independently select individual transducer elements 830 to form respective subsets 840A and 840B. Subsets 840A and 840B may divide the aperture of transducer array 820 into a split aperture comprising two sections of transducer elements 830.

To provide a split aperture imaging mode, in one example, controller 204 may control transducer elements 830 in subset 840A to transmit first ultrasound energy in a first direction, and control transducer elements 830 in subset 840B to transmit second ultrasound energy in a second direction, different than the first direction. The first direction and second direction may be selected such that reflected ultrasound energy may avoid or substantially avoid reflections caused by the medical instrument or medical device, at least to the extent visual obstruction would be produced. In addition, controller 204 may control transducer elements 830 in subset 840A to receive first reflected ultrasound data energy in a first field of view of a region of patient anatomy based at least in part on reflection of the first transmitted ultrasound energy, and control transducer elements 830 in subset 840B to receive second reflected ultrasound data energy in a second field of view of the region of patient anatomy, different than the first field of view, based at least in part on reflection of the second transmitted ultrasound energy.

The split aperture may provide two simultaneous images in a region of a patient on either side of a medical instrument or medical device, such as a mitral valve transcatheter or mitral valve implant. By providing imaging from two sources, e.g., first and second subsets 840A and 840B, probe 800A may allow imaging around the medical instrument or device that is causing shadowing or other visual artifacts. In some example, if fields of view of subsets 840A, 840B overlap, the overlapping portions may be stitched together to maintain ultrasound image data around the device.

This plurality of ultrasound transducer elements 830 in transducer array 820 may comprise any number N of ultrasound transducers. As one non-limiting example, transducer array 820 could have at least N=32 transducer elements 830 and, in some cases, at least N=64 transducer elements or at least N=128 transducer elements. The plurality of ultrasound transducer elements 830 in each of subsets 840A, 840B are operable to transmit ultrasound energy in first and second directions when receiving an excitation signal from, for example, controller 204 of ultrasound workstation 150 or guidance workstation 50, and associated circuitry, and are operable to receive reflected ultrasound energy created by reflections from the ultrasound energy in different fields of view, and to transmit the data representing the reflected ultrasound energy to, for example, controller 204 of ultrasound workstation 150 or guidance workstation 50, for generation of one or more ultrasound images.

Any number of the plurality of ultrasound transducer elements 830 in transducer array 820 could be active at a given time, including all of them. Controller 204 selects each of subsets 840A, 840B to have less than N transducer elements and, in some cases, less than N/2 transducer elements. In some examples, transducer elements 830 selected for subsets 840A and 840B may be mutually exclusive. While the split between subset 840A and 840B is shown in FIG. 16C to divide the transducer elements 830 evenly, this split could be anywhere in the plurality of ultrasound transducer elements 830. Controller 204 may select transducer elements 830 to form subsets 840A, 840B at different positions along transducer array 820. In some examples, subsets 840A, 840B may have the same number of transducer elements 830 or different numbers of transducer elements. There may be an unused space between subsets 840A and 840B, either empty or occupied by unused transducer elements 830. Alternatively, subsets 840, 840B may abut one another such that there is substantially no space and no unused transducer elements 830 between them.

By splitting the plurality of ultrasound transducer elements 830 into at least two subsets, e.g., operating as sub-arrays, the ultrasound energy emanating from the arrays may be steered and pointed in at least two separate directions. Controller 204 may select the individual transducer elements 230 to form each of subsets 840A, 840B automatically or in response to user input. For example, controller 204 may form and control subsets 840A, 840B to provide a split aperture mode of imaging automatically in response to detection of obstruction or in response to user input selecting the split aperture mode, e.g., in the case obstruction is observed by the user. The ultrasound energy of the first subset 840A and the second subset 840B may be independently steerable, e.g., electrically by steering a phased array of the transducer elements 830.

It should also be noted that any or all of the plurality of ultrasound transducer elements 830 may be assigned to subsets 840A, 840B, to receive an excitation signal for transmission of ultrasound energy or to receive reflected ultrasound energy. In some examples, controller 204 may select all of transducer elements 830 of array 820 to form both subsets 840A, 840B such that some of transducer elements 830 are used to form subset 840A and some of transducer elements 830 are used to form subset 840B and all of transducer elements 830 are selected and active (transmitting ultrasound energy and/or receiving reflected ultrasound energy). Alternatively, controller 204 may select less than all transducer elements 830 to form subsets 840A, 840B such that some transducer elements may be unselected and idle, and may not form part of subsets 840A, 840B.

In some examples, controller 204 may control transducer elements to transmit third ultrasound energy in a third direction different than the first and second directions and receive third reflected ultrasound energy in a third field of view different than the first and second fields of view. For example, the third field of view may encompass the area of interest in a region of the patient and may otherwise encompass the location of the medical instrument or medical device. In some examples, the third field of view may include portions of the first and second fields of view and an area between the first and second fields of view. In other examples, the third field of view may include all of the first and second fields of view and an area between the first and second fields of view. In order to avoid obstruction in the third field of view caused by the presence of the medical instrument or medical device, controller 204 may control the transducer array to cease transmitting ultrasound energy in the third direction and cease receiving third reflected ultrasound energy. Controller 204 may begin transmitting ultrasound energy in the first and second directions and begin receiving first reflected ultrasound energy and second reflected ultrasound energy so as to avoid transmitting ultrasound energy to or receiving reflected ultrasound energy from the medical instrument or medical device in order to avoid or substantially avoid the obstruction upon detection of the obstruction.

Figure 16D:
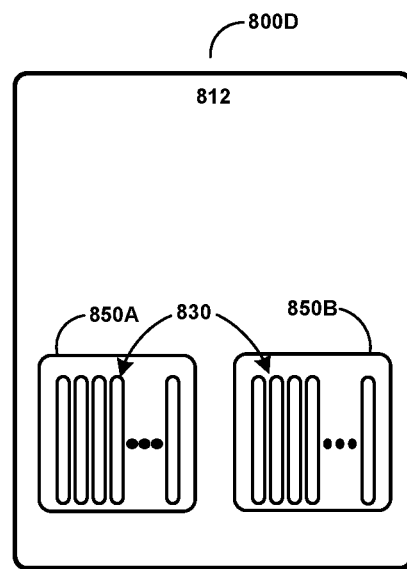
FIG. 16D is a block diagram of another example of an ultrasound probe with first and second transducer arrays which may be used in the system of FIG. 3A or 3B.

FIG. 16D is a block diagram of another example of an ultrasound probe 800D with first and second transducer arrays 850A, 850B which may be used in the system of FIG. 3A or 3B. In the example of FIG. 16D, ultrasound probe 800D comprises a housing 812 and may substantially conform to the description of probe 800A of FIGS. 16A and 16C, in structure and function as described above, except that, instead of dividing transducer elements 830 in a single transducer array 820 into first and second sub-sections 840A, 840B to support a split aperture mode, probe 800D provides a first ultrasound transducer array 850A and a second, separate ultrasound transducer array 850B, each including respective transducer elements 830. The first ultrasound transducer array 880 and the second ultrasound transducer array 890 are operable to transmit ultrasound energy in first and second directions when receiving an excitation signal from, for example, controller 204, e.g., of guidance workstation 50 or ultrasound workstation 150, and are operable to receive reflected ultrasound energy created by reflections from the ultrasound energy in first and second fields of view and to transmit data representative of the reflected ultrasound energy to, for example, controller 204 of ultrasound workstation 150 or guidance workstation 50, e.g., for generation of one or more ultrasound images.

First and second transducer arrays 850A and 850B may be separate arrays that are independently controllable by controller 204 to support a split aperture imaging in manner similar to the use of first and second subsets of transducers, as described above. Any number of the ultrasound transducer elements within the first ultrasound transducer array 850A and the second ultrasound transducer array 850B could be active at a given time, including all of them. In some examples, between the first ultrasound transducer array 850A and the second ultrasound transducer array 850B is a space. In other examples, arrays 850A, 850B may substantially abut one another such that there is no significant space between them.

To provide a split aperture imaging mode, in one example, controller 204 may control transducer elements 830 in transducer array 850A to transmit first ultrasound energy in a first direction, and control transducer elements 830 in transducer array 850B to transmit second ultrasound energy in a second direction, different than the first direction. The first direction and second direction may be selected such that reflected ultrasound energy may avoid or substantially avoid reflections caused by the medical instrument or medical device, at least to the extent visual obstruction would be produced. In addition, controller 204 may control transducer elements 830 in transducer array 850A to receive first reflected ultrasound data energy in a first field of view of a region of patient anatomy based at least in part on reflection of the first transmitted ultrasound energy, and control transducer elements 830 in transducer array 850B to receive second reflected ultrasound data energy in a second field of view of the region of patient anatomy, different than the first field of view, based at least in part on reflection of the second transmitted ultrasound energy.

Hence, controller 204 may control transducer elements 230 in transducer array 850A, 850B to steer transmission of ultrasound energy in first or second directions, respectively, and received reflected ultrasound energy in first or second fields of view, respectively. In addition, in some examples, arrays 850A, 850B may be positioned and a space between the arrays may be sized to further support first ultrasound transducer array 850A and second ultrasound transducer array 850B actively emitting ultrasound energy in first and second directions, and first ultrasound transducer array 850A and second transducer array 850B receiving reflected ultrasound energy in different fields of view of the patient anatomy. In other examples, arrays 850A, 850B may abut one another such that there is substantially no space between them. As in the example of FIGS. 16A and 16C, the ultrasound energy from first ultrasound transducer array 850A and second ultrasound transducer array 850B may be independently steerable.

In some examples, controller 204, e.g., of guidance workstation 50 or ultrasound workstation 150, may control transducer elements to transmit third ultrasound energy in a third direction different than the first and second directions and receive third reflected ultrasound energy in a third field of view different than the first and second fields of view. Controller 204 may control the transducer array to cease transmitting ultrasound energy in the third direction as the third field of view may encompass the medical instrument or medical device and may result in obstruction. Controller 204 may begin transmitting ultrasound energy in the first and second directions which may avoid or substantially avoid the medical instrument or medical device so as to avoid the obstruction upon detection of the obstruction.

Referring back to FIG. 16B, transducer elements 830 in array 860 may be controlled substantially as described with reference to FIGS. 16A, 16C and 16D so that array 860 transmits ultrasound energy in first and second directions and receives ultrasound energy in first and second fields of view to support a split aperture imaging mode, e.g., to obtain images from different sides of a medical instrument or medical device and thereby avoid obstruction, such as shadowing, that may be caused by the medical instrument or medical device.

In some examples, the first field of view and the second field of view may be any combination of left or right (e.g., along the medial-lateral axis or 0 degrees or 180 degrees) or top or bottom (e.g., along the posterior-anterior axis or 90 degrees or 270 degrees) with respect to the longitudinal axis of the medical instrument or medical device when displaying a two-dimensional image. In other examples, the first field of view and the second field of view may be any combination of locations between left or right (not along the medial-lateral axis or not at 0 degrees or 180 degrees) or top or bottom (not along the posterior-anterior axis or not at 90 degrees or 270 degrees) with respect to the longitudinal axis of the medical instrument or medical device when displaying a two-dimensional image.

In some examples, controller 204, e.g., of guidance workstation 50 or ultrasound workstation 150, may control transducer elements to transmit third ultrasound energy in a third direction different than the first and second directions and receive third reflected ultrasound energy in a third field of view different than the first and second fields of view. The controller 204 may control the transducer array to cease transmitting ultrasound energy in the third direction as the third field of view may encompass the medical instrument or medical device and may result in obstruction. Controller 204 may begin transmitting ultrasound energy in the first and second directions which may avoid or substantially avoid the medical instrument or medical device so as to avoid the obstruction upon detection of the obstruction.

Figure 16E:
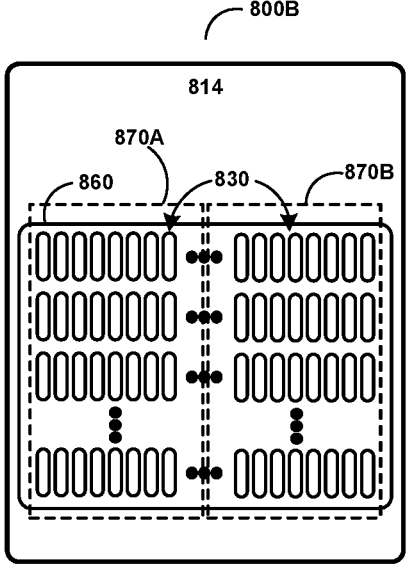
FIG. 16E is a block diagram of another example of an ultrasound probe with a two-dimensional transducer array which may be used in the system of FIG. 3A or 3B, illustrating selection of transducer subsets.

FIG. 16E is a block diagram of another example of ultrasound probe 800B with a two-dimensional transducer array 860 which may be used in the system of FIG. 3A or 3B, illustrating selection of subsets 870A, 870B of transducer elements 830 in array 860. Hence, ultrasound probe 800B in FIG. 16E substantially corresponds to the description in FIG. 16B, but further illustrations subsets 870A, 870B. In this example, the plurality of ultrasound transducer elements 830 in transducer array 860 is split into a first two-dimensional subset 870A of transducer elements 830 and a second two-dimensional subset 870B of transducer elements. While the split between the subsets 870A, 870B within array 860 is shown in a particular fashion in the figure, this split could be anywhere in the plurality of ultrasound transducer elements 830. As described with reference to FIG. 16C, subsets 870A, 870B may each include the same number of transducer elements 830 or different numbers of transducer elements 830, and the subsets 870A, 870B may use all or less than all transducer elements in two-dimensional array 860.

By splitting the plurality of ultrasound transducer elements into at least two arrays, the ultrasound energy emanating from the arrays may be pointed in at least two separate directions, e.g., providing a split aperture for transmission of ultrasound energy and reception of reflected ultrasound energy. To support a split aperture imaging mode, transducer array 860 may be controlled substantially as described with reference to FIGS. 16A, 16C and 16D so that transducer elements 830 transmit ultrasound energy in first and second directions and receive ultrasound energy in first and second fields of view to support a split aperture imaging mode, e.g., to obtain images from different sides of a medical instrument or medical device and thereby avoid or substantially avoid obstruction, such as shadowing, that may be caused by the medical instrument or medical device.

For example, controller 204, e.g., of guidance workstation 50 or ultrasound workstation 150, may control transducer elements 830 in transducer subset 870A to transmit first ultrasound energy in a first direction, control transducer elements 830 in transducer subset 870B to transmit second ultrasound energy in a second direction, different than the first direction. The first direction and second direction may be selected such that reflected ultrasound energy may avoid or substantially avoid reflections caused by the medical instrument or medical device, at least to the extent visual obstruction would be produced. In addition, controller 204 may control transducer elements 830 in transducer subset 870B to receive first reflected ultrasound data energy in a first field of view of a region of patient anatomy based at least in part on reflection of the first transmitted ultrasound energy, and control transducer elements 830 in transducer subset 870B to receive second reflected ultrasound data energy in a second field of view of the region of patient anatomy, different than the first field of view, based at least in part on reflection of the second transmitted ultrasound energy. The ultrasound energy of the first subset 870A and the second array 870B may be independently steerable. It should also be noted that all of the plurality of ultrasound transducer elements 830 of array 860 need not be assigned to subsets 870A, 870B.

In some examples, controller 204, e.g., of guidance workstation 50 or ultrasound workstation 150, may control transducer elements to transmit third ultrasound energy in a third direction different than the first and second directions and receive third reflected ultrasound energy in a third field of view different than the first and second fields of view. The controller 204 may control the transducer array to cease transmitting ultrasound energy in the third direction and begin transmitting ultrasound energy in the first and second directions so as to avoid the obstruction upon detection of the obstruction.

Figure 16F:
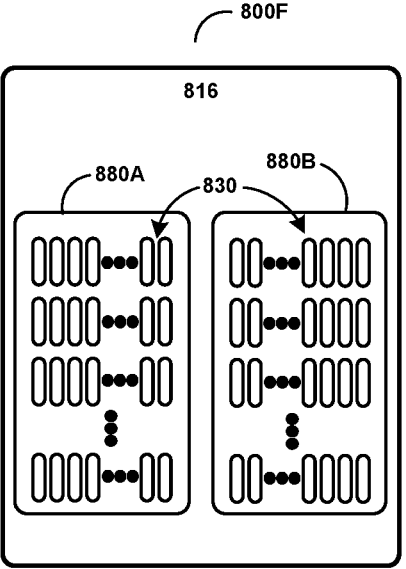
FIG. 16F is a block diagram of another example of an ultrasound probe with first and second two-dimensional transducer arrays which may be used in the system of FIG. 3A or 3B.

FIG. 16F is a block diagram of another example of an ultrasound probe 800F with first and second two-dimensional transducer arrays 880A, 880B which may be used in system 10A or 10B of FIG. 3A or 3B. In the example of FIG. 16F, ultrasound probe 800F comprises a housing 816 and may substantially conform to probe 800B of FIGS. 16B and 16E, except that, instead of the use of transducer elements 830 in a single transducer array 860 as in FIG. 16B or dividing transducer elements 830 in a single, two-dimensional transducer array 860 into first and second two-dimensional subsets 870A, 870B as in FIG. 16E, to support a split aperture mode, probe 800F provides a first two-dimensional ultrasound transducer array 880A and a second, separate two-dimensional ultrasound transducer array 880B, each including respective transducer elements 830. The first ultrasound transducer array 880A and the second ultrasound transducer array 880B are operable to transmit ultrasound energy in first and second directions when receiving an excitation signal from, for example, controller 204 of ultrasound workstation 150 or guidance workstation 50, and are operable to receive reflected ultrasound energy created by reflections from the ultrasound energy in first and second fields of view and to transmit data representative of the ultrasound data reflected ultrasound energy to, for example, controller 204 of ultrasound workstation 150 or guidance workstation 50, e.g., for generation of one or more ultrasound images.

First and second transducer arrays 880A and 880B may be separate arrays that are independently controllable by controller 204 to support a split aperture imaging mode in manner similar to the use of first and second subsets 870A, 870B of transducers in FIG. 16E, as described above. Any number of the transducer elements within the first ultrasound transducer array 880A and the second ultrasound transducer array 880B could be active at a given time, including all of them. In some examples, between the first ultrasound transducer array 880A and the second ultrasound transducer array 880B is a space. In other examples, arrays 880A, 880B may substantially abut one another such that there is no significant space between them.

To provide a split aperture imaging mode, in one example, controller 204 may control transducer elements 830 in transducer array 880A to transmit first ultrasound energy in a first direction, control transducer elements 830 in transducer array 880B to transmit second ultrasound energy in a second direction, different than the first direction. The first direction and second direction may be selected such that reflected ultrasound energy may avoid or substantially avoid reflections caused by the medical instrument or medical device, at least to the extent visual obstruction would be produced. In addition, controller 204 may control transducer elements 830 in transducer array 880A to receive first reflected ultrasound data energy in a first field of view of a region of patient anatomy based at least in part on reflection of the first transmitted ultrasound energy, and control transducer elements 830 in transducer array 880B to receive second reflected ultrasound data energy in a second field of view of the region of patient anatomy, different than the first field of view, based at least in part on reflection of the second transmitted ultrasound energy.

Hence, controller 204 may control transducer elements 230 in transducer arrays 850A, 850B to steer transmitted ultrasound energy in first or second directions, respectively, and received reflected ultrasound energy in first or second fields of view, respectively. In addition, in some examples, arrays 880A, 880B may be positioned and a space between the arrays may be sized to further support first ultrasound transducer array 850A and second ultrasound transducer array 850B actively emitting ultrasound energy in first and second directions, and first ultrasound transducer array 850A and second transducer array 850B receiving reflected ultrasound energy in different fields of view of the patient anatomy. In other examples, arrays 850A, 850B may abut one another such that there is substantially no space between them. As in the example of FIGS. 16A and 16C, the ultrasound energy from first ultrasound transducer array 880A and second ultrasound transducer array 880B may be independently steerable.

In some examples, controller 204, of e.g. guidance workstation 50 or ultrasound workstation 150, may control transducer elements to transmit third ultrasound energy in a third direction different than the first and second directions and receive third reflected ultrasound energy in a third field of view different than the first and second fields of view. A medical instrument or medical device may enter the third field of view and begin causing obstruction. The controller 204 may control the transducer array to cease transmitting ultrasound energy in the third direction so as avoid or substantially avoid ultrasound reflections from the medical instrument or medical device that is causing the obstruction. Controller 204 may begin transmitting ultrasound energy in the first and second directions and receiving reflected ultrasound energy in the first and second fields of view so as to continue to provide images of anatomy of interest while avoiding the obstruction upon detection of the obstruction. In some examples, controller 204 may automatically detect the obstruction and automatically change from controlling the transducer array to transmit in the third direction and receive in the third field of view to transmit in the first and second directions and receive in the first and second fields of view.

Ultrasound probes 800A, 800B, 800D, and 800F, illustrated in FIGS. 16A-16F, each may be configured for use with ultrasound imager 140 of FIG. 3A or disposed at a distal end of a catheter such as a transesophageal echocardiography (TEE) catheter, e.g., for use as an ultrasound transducer array 144 with ultrasound imager 142 of FIG. 3B. Accordingly, in some examples, ultrasound probes 800A. 800B, 800D and 800F may be sized and configured for use outside of a human body or within a human body and, particularly, within a lumen of the human body such as the esophagus.

Figure 17A:
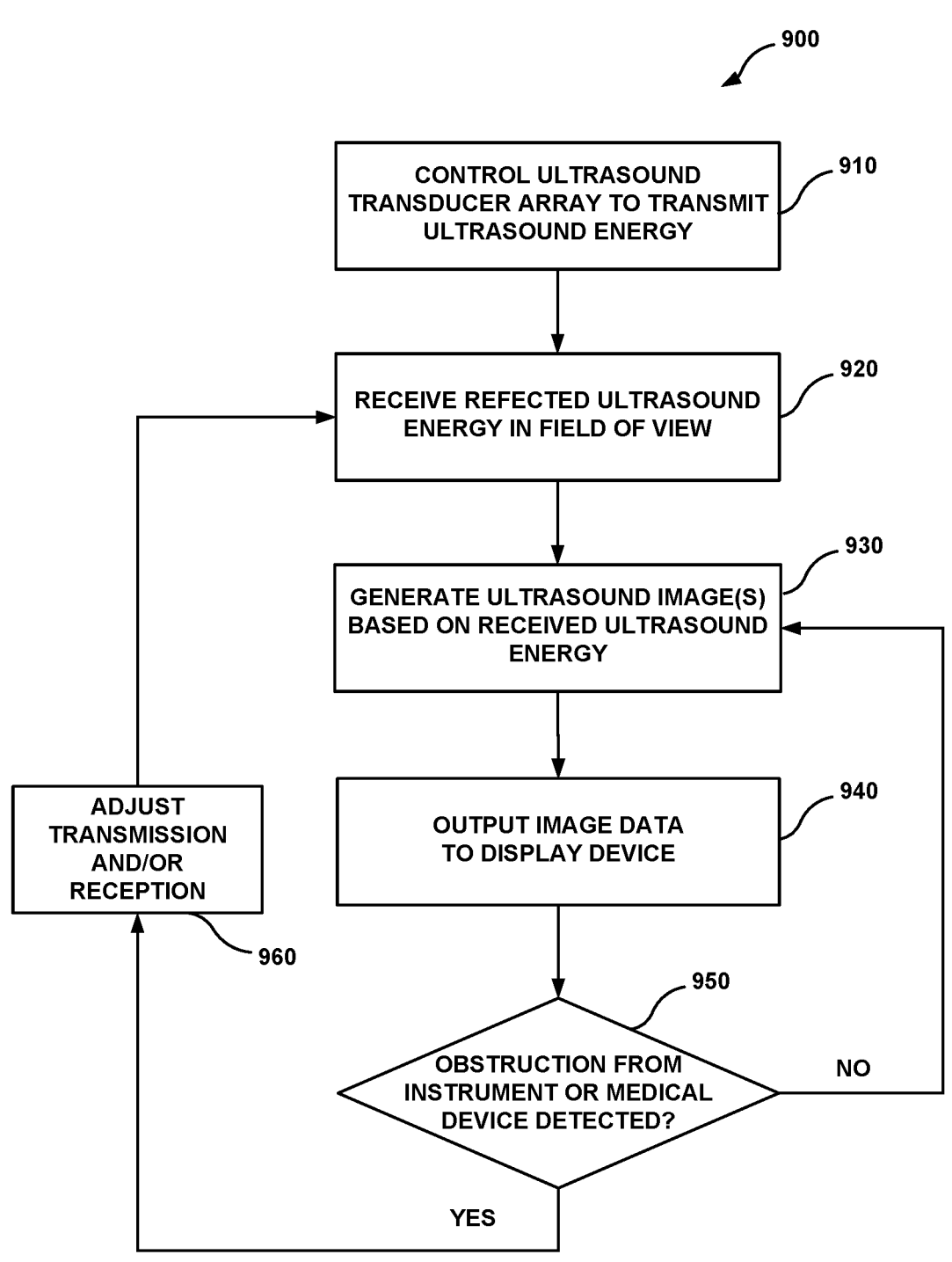
FIG. 17A is a flowchart of one example of a method of operating an ultrasound imaging system.

FIG. 17A is a flowchart of one example of a method of operating an ultrasound imaging system. The ultrasound imaging system may include, for example, ultrasound workstation 150 in combination with ultrasound imager 140 (FIG. 3A) or ultrasound imager 142 (FIG. 3B) or guidance workstation 50 in some examples. FIG. 17A shows a method 900 of controlling an ultrasound probe, such as any of probes 800A, 800B, 800D, 800F (FIGS. 16A-16F), so as to avoid or mitigate visual obstructions in an ultrasound image obtained by the probe. This method 900 could be implemented, as an example, in the guidance workstation 50, in the ultrasound workstation 150, or in the ultrasound imager 140 or 142. For example, instructions for causing one or more processors of controller 204 to control the ultrasound probe may be part or all of application 216 stored in memory 202 and the one or more processors of controller 204 acting on those instructions could execute this method. In other examples, controller 204 could be one or more processors arranged as fixed function circuitry or a combination of programmable and fixed function circuitry. In various examples, the ultrasound probe to be controlled could be a probe 800A, 800B, 800D, 800F, as described herein. For example, one or more processors of controller 204 of ultrasound workstation 150 or guidance workstation 50 may control ultrasound transducer array, such as an ultrasound transducer array described with reference to any of FIGS. 16A-16F, to transmit ultrasound energy (910). In general, the one or more processors associated with controller 204 may control suitable electronic circuitry to provide one or more excitation signals to the ultrasound probe.

Controller 204 then receives reflected ultrasound energy from the ultrasound probe in a field of view (920), e.g., the third field of view discussed above. Controller 204 processes the received ultrasound energy and generates one or more ultrasound images based on the received ultrasound energy (930). Such processing may include the processing described herein with respect to other described figures herein. Controller 204, e.g., of ultrasound workstation 150 or guidance workstation 50, may output image data to a display device, such as display device 206 or display device 110, to control the display device to present the one or more ultrasound images (940). The steps in method 900 are not necessarily performed in the order shown in FIG. 17A. As one example, step 940 of outputting image data may be performed independently and out of order with other steps of method 900.

Controller 204, e.g., ultrasound workstation 150 or guidance workstation 50, may detect whether there is an obstruction in the reflected ultrasound energy, e.g., due to presence of a medical instrument or medical device in the field of view (950). Controller 204 may analyze the reflected ultrasound energy or one or more ultrasound images generated based on the reflected ultrasound energy to determine whether there is an obstruction. For example, controller 204 may distinguish between characteristics of ultrasound energy, or characteristics of ultrasound image data, indicative of obstruction by natural anatomy or foreign objects. For example, characteristics such as amplitude, frequency, spectral content or spatial information of ultrasound energy, or similar image information, such as contrast or pixelation, associated with obstruction by a foreign object may provide a signature that sets it apart from obstruction by a natural anatomic object. A medical instrument or medical device will typically include some material, such as metal, that is different from patient bone or tissue. This difference in material may yield different reflective characteristics that may be apparent in reflected ultrasound energy signals or ultrasound image data, for example, based on amplitude, frequency, spectral content, spatial information, contrast or pixelation. For example, a live ultrasound image that is clear in black and white with anatomical borders that are relatively easy to delineate may become gray or partially gray due to the presence of the medical instrument or medical device. Controller 204 may identify this change.

If an obstruction is detected (the "YES" path), e.g., in the reflected ultrasound energy or in the ultrasound image generated based on the reflected ultrasound energy, e.g., due to a medical instrument or medical device, controller 204 may automatically adjust transmission of ultrasound energy or reception of reflected ultrasound energy (960). For example, controller 204 of ultrasound workstation 150 or guidance workstation 50 may automatically select a split aperture mode and control a transducer array to operate in the split aperture mode, as described in this disclosure. For example, controller 204 may control the transducer array to cease transmitting ultrasound energy in the third direction so as avoid or substantially avoid ultrasound reflections from the medical instrument or medical device that is causing the obstruction. Controller 204 may begin transmitting ultrasound energy in the first or second directions and receiving reflected ultrasound energy in the first or second fields of view so as to continue to provide images of anatomy of interest while avoiding the obstruction. Controller 204 may additionally, or alternatively, automatically and dynamically steer the ultrasound energy in response to further obstruction detection due to movement of the medical instrument or device within a region of a patient anatomy.

Alternatively, a clinician may use one or more user input devices to manually steer the ultrasound energy in directions outside of the area of the patient's anatomy in which the medical instrument or medical device is causing an obstruction. For example, the clinician may actuate manual controls to manually move the ultrasound imager 142. In some examples, controller 204 may provide a visual prompt or target to help guide the clinician on where to move the ultrasound imager 142. In particular, a clinician may view a live ultrasound image in which there is a visual obstruction, and actuate manual controls, e.g., on ultrasound workstation 150 or ultrasound imager 142, to move the ultrasound imager 142 to a position at which the obstruction is eliminated or reduced in the image either, with the aid of the visual prompt or target in some examples. Alternatively, the clinician may enter user input to cause controller 204 to steer the ultrasound energy away from the obstructed region. In some examples, the clinician may enter user input designating selection of a split aperture imaging mode as described in this disclosure, in which case controller 204 may transition from a regular imaging mode to a split aperture mode in which the ultrasound probe images in fields of view at different sides of a medical instrument or medical device.

Figure 19:
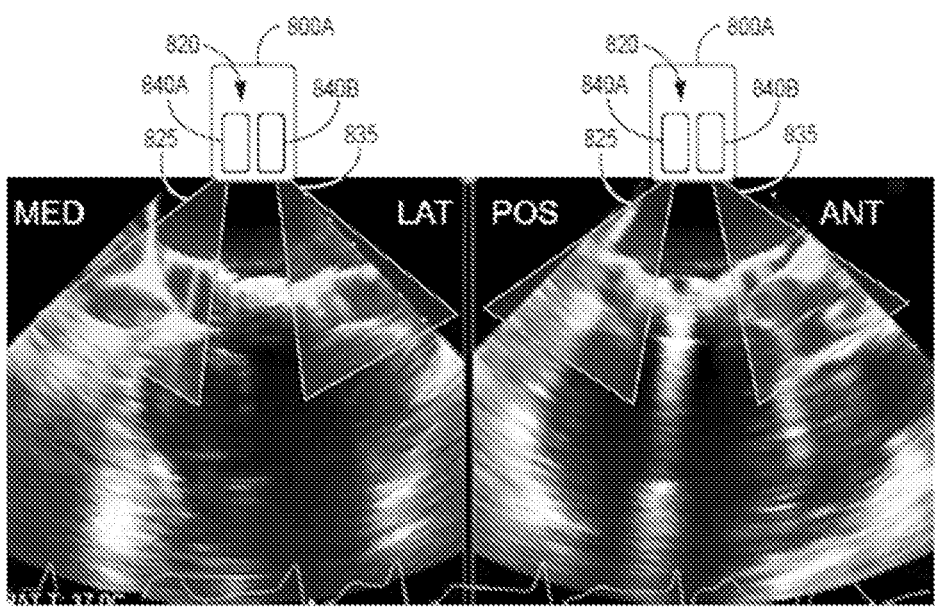
FIG. 19 is a schematic view of an example of the use of the ultrasound imaging system of FIG. 18A to produce ultrasound images.

As an illustration, in a mitral valve replacement or repair surgery, the ultrasound energy could be steered away from a central portion of an anatomical region in which an instrument or medical device resides and toward the outside of the anatomical region. In this example, the anatomical region is the mitral valve area of the left ventricle and left atrium of the heart, e.g., as shown in FIG. 19 (discussed below), and instrument or device may be a catheter delivered for a mitral valve replacement or repair procedure. In one example, as described above, controller 204 or application 216 may be configured to detect when the instrument or medical device is likely to cause visual obstructions, so as to monitor for reflected ultrasound energy that is indicative of the beginning of visual obstructions and automatically beam steer the ultrasound energy to establish one or more fields of view that avoid the instrument or medical device to eliminate or mitigate the visual obstructions.

Once the ultrasound energy has been steered away (for example, by active steering or by changing to a split-aperture mode) from the medical instrument or medical device, the visual obstruction should be avoided or mitigated as reflection of ultrasound energy from the medical instrument or medical device in the field of view will be avoided or lessened. If an obstruction is not detected by controller 204, or if the image data being displayed does not otherwise show visual obstructions, the operation of the ultrasound probe need not be adjusted. In this case (the "NO" path), method 900 may proceed to continue to generate ultrasound images based on received ultrasound energy (930), i.e., without the need for any adjustment with respect to transmitted ultrasound energy or received reflected ultrasound energy. If the clinician nevertheless would like to adjust the probe, the process performed by controller 204 would return to step 910 instead of step 930. It should be noted that step 950 could be placed before step 940 if desired.

Figure 17B:
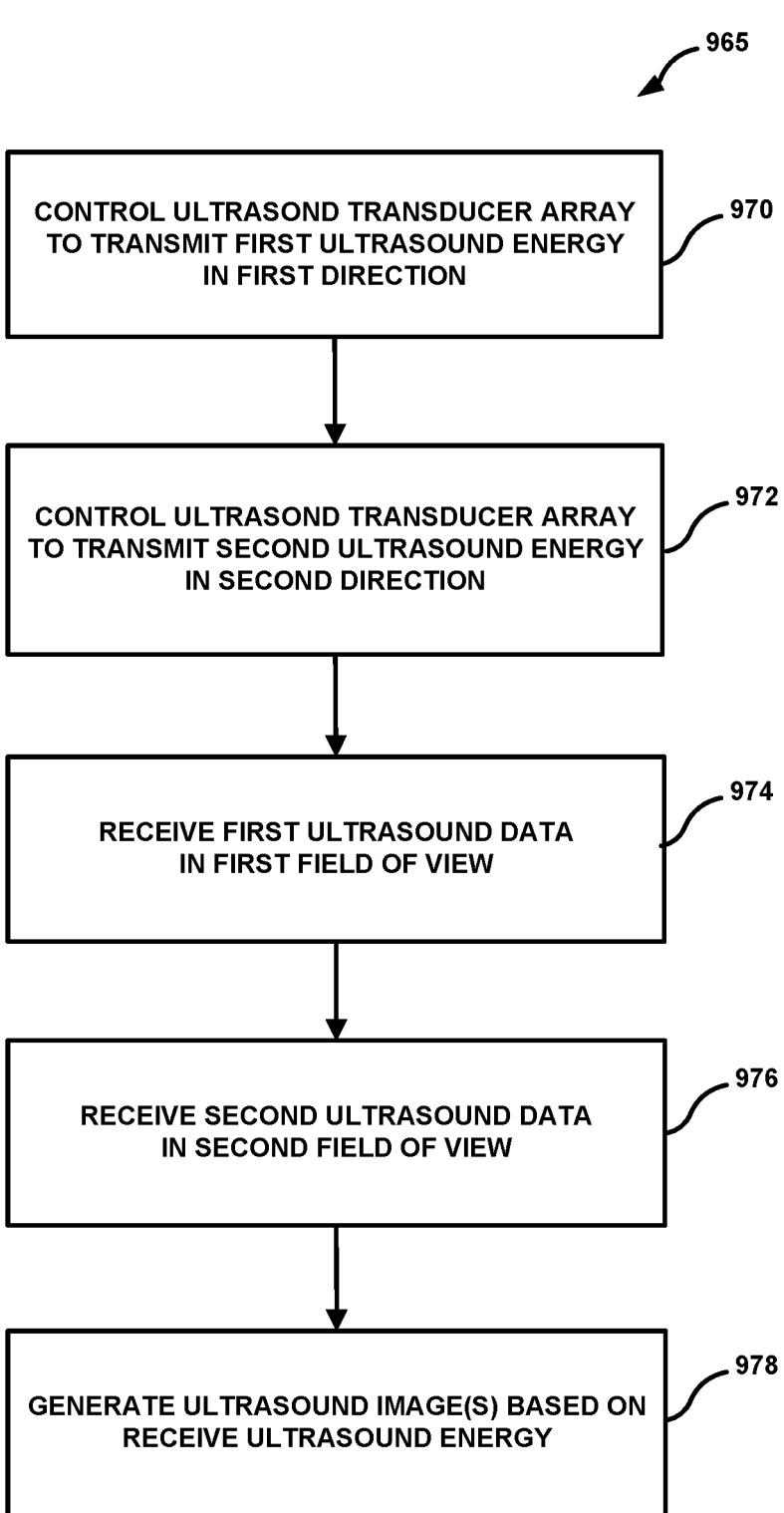
FIG. 17B is a flowchart of another example of a method of operation of an ultrasound imaging system.

FIG. 17B is a flowchart of another example of a method of operation of an ultrasound imaging system. FIG. 17B shows a method 960 of controlling an ultrasound probe, such as any of probes 800A, 800B, 800D, 800F (FIGS. 16A-16F). This method could be implemented, for example, in the guidance workstation 50, in the ultrasound workstation 150, or in the ultrasound imager 140 or 142. For example, instructions for causing one or more processors of controller 204, e.g., of guidance workstation 50 or ultrasound workstation 150, to control the ultrasound probe may be part or all of application 216 stored in memory 202 and the one or more processors of controller 204 acting on those instructions could execute this method. In other examples, controller 204 could be one or more processors arranged as fixed function circuitry or a combination of programmable and fixed function circuitry. In various examples, the ultrasound probe to be controlled could be a probe 800A, 800B, 800D, 800F, as described herein. For example, one or more processors of controller 204 may control the ultrasound transducer array of the ultrasound probe, such as an ultrasound transducer array described with reference to any of FIGS. 16A-16F, to transmit first ultrasound energy in a first direction (970). Controller 204 may accomplish this by providing one of more excitation signals to the ultrasound transducer array of the ultrasound probe. Controller 204 may control the ultrasound transducer array to transmit second ultrasound energy in a second direction (972). Again, controller 204 may accomplish this by providing one or more excitation signals to the ultrasound transducer array of the ultrasound probe. Controller 204 may control the ultrasound transducer array to simultaneously or substantially simultaneously transmit the first ultrasound energy and the second ultrasound energy.

Controller 204 may control the ultrasound transducer array to receive first reflected ultrasound energy in a first field of view of a region of patient anatomy based at least in part on reflection of the first transmitted ultrasound energy (974). In addition, controller 204 may control the ultrasound transducer array to receive second reflected ultrasound energy in a second field of view (976). Controller 204 may control the ultrasound transducer array to simultaneously or substantially simultaneously receive the first reflected ultrasound energy and the second reflected ultrasound energy. As further shown in FIG. 16B, controller 204 may generate one or more ultrasound images based on the received ultrasound energy (978).

Controller 204, e.g., of guidance workstation 50 or ultrasound workstation 150, may control the transducer array, according to a split aperture mode, so that the reflected ultrasound energy received in the first and second fields of view is not obstructed, e.g., by the presence of a medical instrument or medical device that reflects the transmitted ultrasound energy. Rather, in some examples, the first and second fields of view may be selected to include areas at different sides of a longitudinal axis of a medical instrument or medical device, and exclude an area in which the medical instrument or medical device resides. In other examples, the first and second field may be selected to include areas at different sides of a medical instrument or medical device, and also include an area in which the medical instrument or medical device resides.

Hence, one or more processors of controller 204 may control the ultrasound transducer array to transmit and receive ultrasound energy such that the first field of view is selected to include a first portion of the region of the patient anatomy on a first side of at least one of a medical instrument or medical device when the medical instrument or medical device is introduced into the region of the patient anatomy and the second field of view is selected to include a second portion of the region of the patient anatomy on a second side of the at least one of a medical instrument or medical device when the medical instrument or medical device is introduced into the region of the patient anatomy. For this method, controller 204 may control transducer elements in single transducer array, transducer elements in two, separate transducer arrays, or transducer elements forming subsets of a single transducer array, e.g., as described with reference to probes 800A, 800B, 800D, 800F (FIGS. 16A-16F).

Figure 18A:
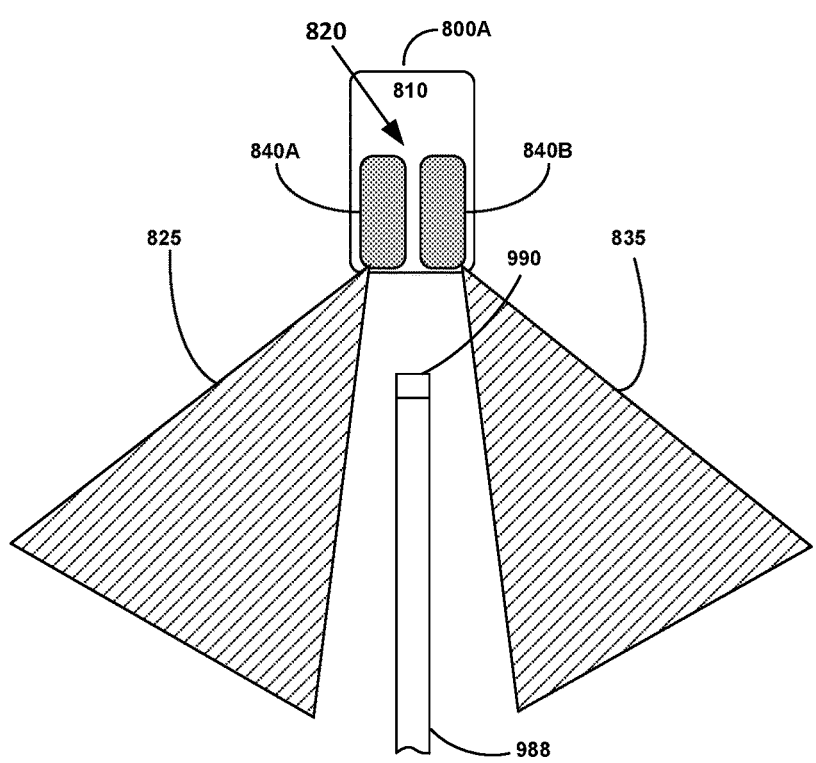
FIG. 18A is a schematic view of an ultrasound imaging system with two fields of view in accordance with an example of this disclosure.

FIG. 18A is a schematic view of an ultrasound imaging system with two fields of view provided by a split aperture imaging mode in accordance with an example of this disclosure. In the example of FIG. 18A, probe 800A (FIGS. 16A and 16C), which alternatively could be any of the probes of FIG. 16B or 16D-16F, transmits and receives ultrasound energy with transducer elements in transducer subset 840A and transducer subset 840B to define a split aperture with first and second fields of view 825, 835 respectively. The ultrasound imaging systems shown in FIGS. 18A-24B and FIGS. 26A-26D may further include ultrasound workstation 150, guidance workstation 50, or ultrasound imager 140 or 142. In this example, controller 204 controls transducer elements in subset 840A and transducer elements in subset 840B to transmit and receive ultrasound energy for imaging in field of view 825 and field of view 835, respectively.

As an alternative, rather than using subsets of transducer elements in a single transducer array, the split aperture could be provided using separate transducer arrays, e.g., as shown in FIG. 16D and FIG. 16F. In either case, as shown in the example of FIG. 18A, the split aperture fields of view 825, 835 include regions at different sides of a medical instrument 988, and do not include medical instrument 988. As result, in some examples, obstruction caused by reflection from medical instrument 988 may be avoided or reduced. In the example of FIG. 18A, medical instrument 988 represents a catheter, with nose cone 990, configured for use in transcatheter mitral valve repair or replacement procedures.

Hence, in some examples, as shown in FIG. 18A, one or both fields of view 825, 835 may be selected to exclude from each field of view a medical instrument or medical device, thereby avoiding obstruction in images produced from the fields of view. In other examples, one or both fields of view 825, 835 may be selected to include regions at different sides of a longitudinal axis of a medical instrument or medical device and include a portion of a region in which the medical instrument or medical device resides. In either case, a split aperture may provide a wider angle of view that may provide enhanced visualization of structures at the sides of region of interest, e.g., on different sides of the longitudinal axis of a medical instrument or medical device in an obstructed region.

Figure 18B:
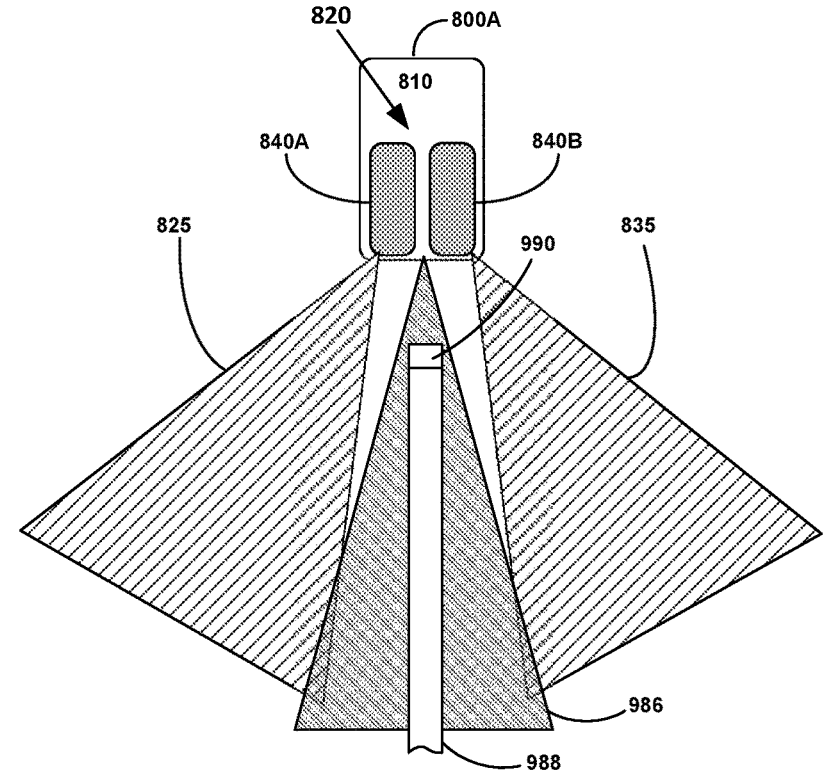
FIG. 18B is another schematic view of the ultrasound imaging system of FIG. 18A with a comparison to the example of FIG. 2.

By controlling transducer elements 830 in subsets 840A, 840B of array 820 to steer and focus ultrasound energy to generate fields of view 825, 835 with a split aperture, probe 800A may avoid the shadowing otherwise caused by medical instrument 988. FIG. 18B shows the system of FIG. 18A, including first and second fields of view 825, 835 in a split aperture imaging mode, in comparison with the obstructed region 986 (FIG. 2), which may be the third field of view described above, inclusive of medical instrument 988, in the regular imaging mode of FIG. 2.

In some examples, system 10 may be configured to provide both a regular imaging mode and a split aperture mode on a selective basis by manual selection by a clinician upon viewing of an obstructed region or upon being automatically notified of an obstruction by controller 204. In other examples, system 10 may be configured to provide both a regular imaging mode and a split aperture mode on a selective basis by automated selection of the split aperture mode by controller 204 upon automatic detection of an obstructed region by controller 204. In some examples, system 10 may be configurable to provide a regular imaging mode and a split aperture mode by procedure-specific selection based on user input indicating a procedure will involve placement of a medical instrument or medical device, e.g., for a transcatheter mitral valve repair or replacement procedures. In other examples, system 10 may provide a regular imaging mode and a split aperture mode by default.

FIG. 19 shows example medial-lateral (MED-LAT) and posterior-anterior (POS-ANT) ultrasound images that could be produced using ultrasound imaging system of FIG. 17A with a split aperture imaging mode as described in this disclosure. In particular, FIG. 19 illustrates how a split aperture ultrasound probe may allow for structures with greater reflection and shadowing risk to be imaged around while still providing relevant imaging data of surrounding anatomy. In FIG. 19, ultrasound probe 800A is shown with ultrasound energy represented as directed to a patient's heart for the purposes of heart surgery, such as transcatheter mitral valve repair or replacement. For example, the image in FIG. 19 is an image of the mitral valve region between the left ventricle and the left atrium. The ultrasound probe 800A could be used in other contexts, such as the placement of other medical instruments or medical devices, either permanently or temporarily, such as with left ventricular assist device (LVAD)s, pacemakers, defibrillators, neurostimulators, muscle stimulators, other valves or valve repair or replacement devices, stents, balloons or surgery using ablation or cutting tools, and with other instruments and medical devices described elsewhere in this disclosure.

While ultrasound probe 800A is shown in this example of FIG. 19, as in FIG. 18A, other ultrasonic probes, such as any of the probes of FIGS. 16B-16F could be used. Transducer elements 830 in ultrasound transducer subset 840A of array 820 transmit first ultrasound energy in first direction and transducer elements 830 in second ultrasound transducer subset 840B of array 820 transmit second ultrasound energy in second direction. The first direction and second direction may be selected such that reflected ultrasound energy may avoid or substantially avoid reflections caused by the medical instrument or medical device, at least to the extent visual obstruction would be produced. As may be seen, the first ultrasound energy and second ultrasound energy are directed in different directions from each other. With this orientation, if a clinician were accessing the central area between the two fields of view of the first and second ultrasound transducer arrays with a medical instrument or medical device, the instrument or medical device would not generate visual obstructions as the ultrasound transducer subsets 840A and 840B are controlled to define fields of view that would not receive ultrasound data reflected from the medical instrument or medical device. Instead, ultrasound transducer subsets 840A and 840B would receive ultrasound data reflected from the anatomical structures at which the ultrasound energy is directed. For example, the different fields of view may be on opposite sides of the medical instrument or medical device. In some examples, they may be on the medial and lateral sides, the anterior and posterior sides or both relative to a patient's body. For instance, the clinician may navigate a catheter loaded with a replacement mitral valve into place by seeing the image of the anatomical structure on either side of the existing mitral valve.

Figure 20:
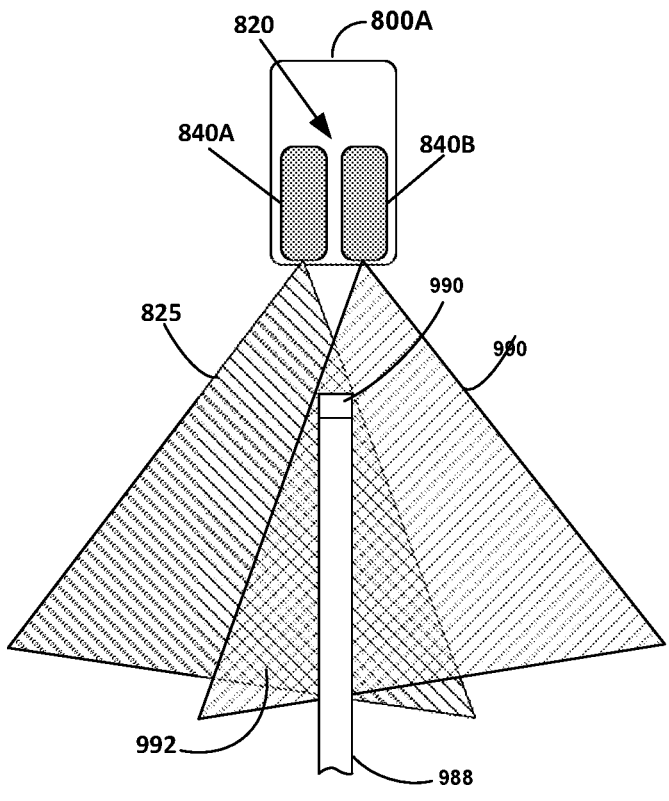
FIG. 20 is a schematic view of an ultrasound imaging system with two fields of view in accordance with another example of this disclosure.

FIG. 20 is a schematic view of an ultrasound imaging system with two fields of view in accordance with another example of this disclosure. In particular, FIG. 20 is a schematic view of an example of an ultrasound imaging system with two overlapping fields of view for a split aperture imaging mode in accordance with an example of this disclosure. In the example of FIG. 20, probe 800A (FIGS. 16A and 16C), which alternatively could be any of the other the probes of FIG. 16B or 16D-16F, transmits and receives ultrasound energy with transducer subset 840A and transducer subset 840B to define a split aperture with first and second fields of view 825, 835, respectively. However, controller 204 controls transducer elements 830 in subsets 840A, 840B, respectively, to steer the transmitted ultrasound energy and focus the received reflected ultrasound energy so that fields of view 825 and 835 overlap at least partially with one another.

Figure 21:
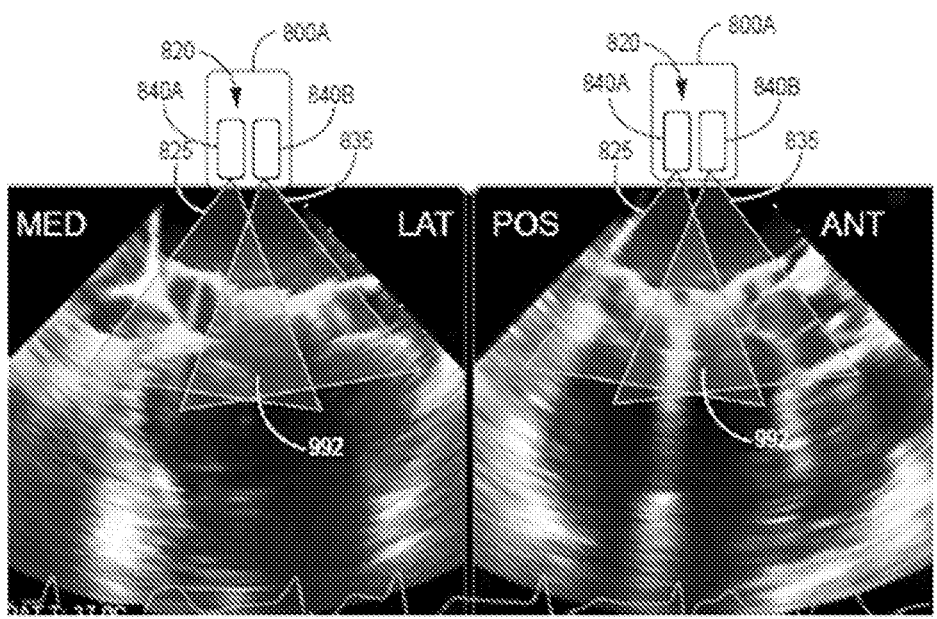
FIG. 21 is a schematic view of an example of the use of the ultrasound imaging system of FIG. 20 to produce ultrasound images.

FIG. 21 illustrates the stitching of images from a split aperture ultrasound probe. In this example, with an overlapping region 992, controller 204 may stitch together images from both fields of view 825, 835 to provide a combined ultrasound image. The combined image may include an obstructed region in which shadowing is caused by medical instrument 988, but further includes side regions on either side of the instrument. In this overlapping split aperture imaging mode, the visualization of more anatomy in these side regions may promote more reliable guidance even though shadowing may appear in the center, overlapping region 992.

FIG. 21 shows example medial-lateral (MED-LAT) and posterior-anterior (POS-ANT) ultrasound images that could be produced using an ultrasound imaging system with a split aperture imaging mode with overlapping fields of view as described in this disclosure and as shown and described with reference to FIG. 20. In particular, FIG. 21 illustrates two overlapping fields of view 825, 835 that produce an overlapping region 992. In FIG. 21, ultrasound probe 800A is shown with ultrasound energy directed to a patient's heart for the purposes of heart surgery, such as mitral valve repair or replacement. Ultrasound probe 800A may be used in other contexts as mentioned above. Again, while ultrasound probe 800A is shown in this example, other ultrasound probes, such as any of the probes of FIG. 16B or 16D-16F could be used. First ultrasound transducer subset 840A transmits first ultrasound energy in a first direction and second ultrasound transducer subset 840B transmits second ultrasound energy in a second direction.

As can be seen in FIG. 21, first field of view 825 and second field of view 835 are directed in different directions from each other. In this example though, controller 204 controls transducer elements 830 in transducer subsets 840A, 840B such that the first ultrasound energy and second ultrasound energy define field of view 825, 835, respectively, that overlap with each other, producing overlapping region 992. For example, the different fields of view may be on opposite sides of the medical instrument or medical device. In some examples, they may be on the medial and lateral sides, the anterior and posterior sides or both relative to a patient's body. It may be desirable to have overlapping region 992 capture some reflected ultrasound energy from the central area. In this example, for a medical instrument or medical device very near the ultrasound probe 800A and between the first field of view 825 and the second field of view 835, ultrasound transducers in subsets 840A, 840B may not receive reflected ultrasound energy from that portion of the medical instrument or medical device in the gap between the two fields of view where the visual obstruction would otherwise be present.

Should a portion of the instrument or medical device fall within the first or second ultrasound fields of view 825 and 835, image processing could be performed in real time, for example, by controller 204 in step 930 (FIG. 17A), to stitch together the image from the reflected ultrasound energy and to remove or mitigate visual obstructions created from the received reflected ultrasound energy associated with the medical instrument or medical device as discussed herein. For example, controller 204 may match the image from the first ultrasound field of view 825 and the image from the second ultrasound field of view 835 based on surrounding anatomy and/or the obstruction and stitch together the image from the first ultrasound field of view 825 and the image from the second ultrasound field of view 835 to produce a more robust image with additional surrounding anatomy and less obstruction.

Figure 22:
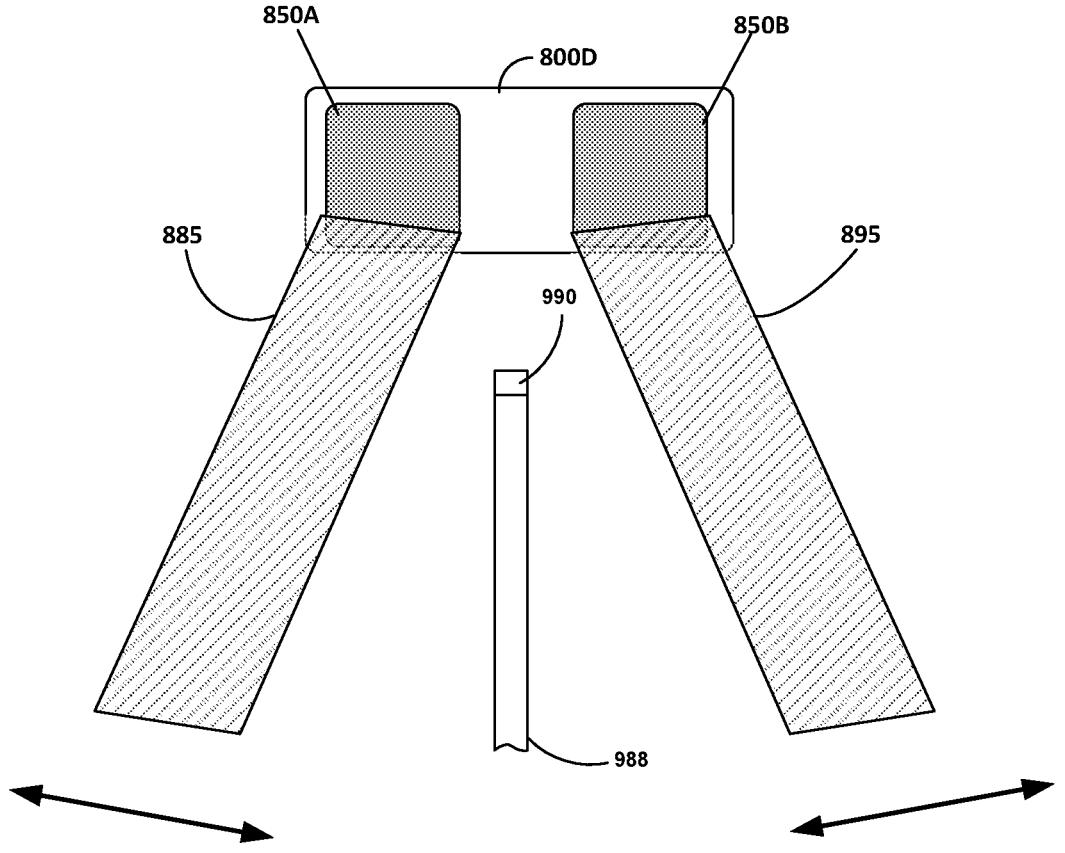
FIG. 22 is a schematic view of another ultrasound imaging system accordance with an example of this disclosure.

FIG. 22 is a schematic view of another ultrasound imaging system in accordance with an example of this disclosure. In the example of FIG. 22, ultrasound probe 800D is shown with a first transducer array 850A and second transducer array 850B, although any of the other probes of FIGS. 16A-16C and 16E-16F may be used. As shown, controller 204 applies beamforming to control first ultrasound energy and second ultrasound energy transmitted by arrays 850A, 850B, respectively, and directed to a patient's heart for the purposes of heart surgery, such as mitral valve repair or replacement. In this example, controller 204 controls arrays 850A, 850B to define fields of view 885 and 895, each of which avoids the region in which medical instrument 988 may cause shadowing.

In general, FIG. 22 illustrates the ability to dynamically steer and focus the ultrasound energy in an adjustable manner to define fields of view that avoid obstructed regions. In this dynamic steering mode example, ultrasound energy beams are steerable to define a variety of different fields of view. In some examples, controller 204 may control arrays 850A, 850B to steer inward or outward relative to medical instrument 988, as indicated by the arrows, permitting dynamic steering to avoid or mitigate obstructions caused by reflection from medical instrument 988.

Controller 204, e.g., of guidance workstation 50 or ultrasound workstation 150, may periodically or continually adjust the steering (e.g., angle, direction or field of view) of ultrasound energy transmitted and received by array 850A and array 850B to avoid or mitigate obstruction caused by the presence of medical instruments or medical devices. Notably, a medical instrument or medical device may move within a region of the patient, presenting a movable source of obstruction for ultrasound imaging and guidance. As the instrument or device moves in the imaging region, it may transition from not causing obstruction to causing substantial obstruction in ultrasound images, or the area that is obstructed from view may move as the device is moved within the patient. Accordingly, it may be desirable to detect obstruction and adjust or select an ultrasound imaging mode to eliminate or mitigate the resulting obstruction. As a medical instrument or medical device moves within an imaging region, controller 204 may detect obstruction and control each of arrays 850A, 850B to automatically steer and focus ultrasound energy to define a different field of view that does not include the medical instrument or medical device or, alternatively, does not present significant obstruction.

Each time that an obstruction is detected, either by a user or automatically by controller 204, the controller may update the steering to include a different field of view that avoids the medical instrument or medical device or, alternatively, does not present significant obstruction. This process may continue on an iterative basis so that system 10 may generally avoid generating images with obstruction. In some examples, controller 204 may continue to steer among different positions until an obstruction is eliminated or mitigated. In some examples, the different positions may be specified by a predefined set or sequence of positions of fields of view. Alternatively, the different positions may be selected based on the output of a machine learning algorithm that generates field of view positions for steering based on spatial or other characteristics of the obstruction, e.g., as indicated by analysis of received ultrasound energy or ultrasound images produced based on the ultrasound energy. Although this process is described with reference to two arrays 850A, 850B, and could be performed with transducer subsets as described with reference to FIGS. 16A-16F, in some examples, a single beam from a single array or subset may be steered to produce an image that avoids obstruction due to presence of medical instrument or medical device, such as in a wide-angle mode or toroidal mode as discussed herein.

Figure 23:
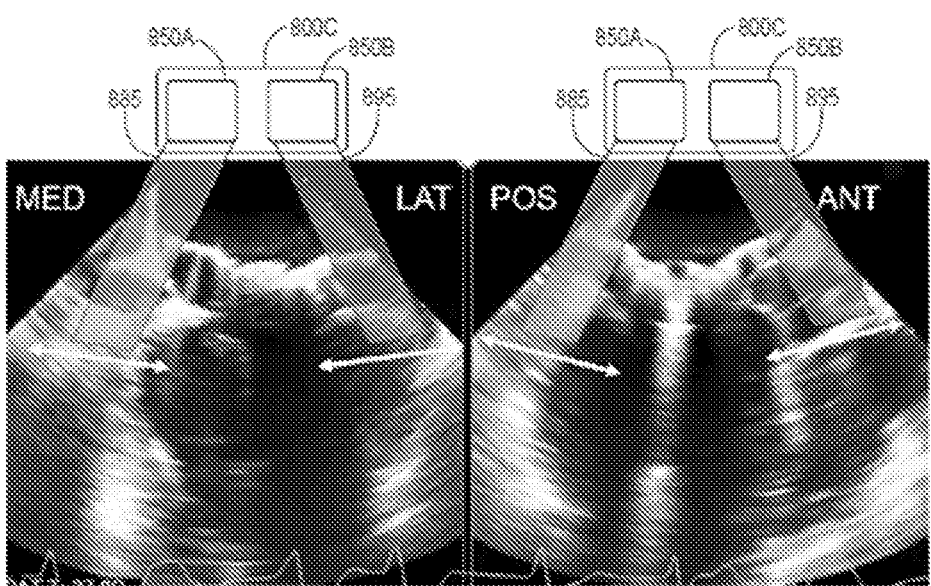
FIG. 23 is a schematic view of an example of the use of the ultrasound imaging system of FIG. 22 to produce ultrasound images.

FIG. 23 is a schematic medial-lateral (MED-LAT) and posterior-anterior (POS-ANT) view of one example of ultrasound energy that could be produced by an ultrasound imaging system with steerable beams as shown in FIG. 22. As shown in FIG. 23, controller 204 may control transducer arrays 850A, 850B such that beams of ultrasound energy may be steered and focused on a selective basis. In some examples, a user may manually control system 10, via user input, to steer beams back and forth to selectively and dynamically define fields of view 885, 895.

Ultrasound probes with fields of view other than the split aperture field of view discussed above may be used that may alleviate problems associated with visual obstruction of anatomy of interest in ultrasound images due the presence of medical instruments or medical devices in a region of the patient being imaged. One such example, may be an ultrasound probe having a wide field of view mode. For example, one or more processors of controller 204, e.g., of guidance workstation 50 or ultrasound workstation 150, may be configured to control an ultrasound transducer array of any of probes of FIGS. 16A-16F to transmit ultrasound energy in a field of view having a generally trapezoidal cross-section, or other selected geometric shapes, that may also provide a wider angle, near field view than when operating in a normal mode with a narrower field of view. A generally trapezoidal or other similar geometry may, in some examples, provide a reduced imaging depth with enhanced resolution in the near field. In this case, the field of view may include less of a medical instrument or medical device, and possibly produce less shadow.

Another example of an ultrasound probe that may alleviate problems associated with visual obstruction of anatomy of interest in ultrasound images due the presence of medical instruments or medical devices in a region of the patient being imaged is an ultrasound probe with a generally toroidal field of view mode. In this example, the field of view may surround the medical instrument or medical device, but not include the medical instrument or medical device. The medical instrument or medical device may be in the cavity in the generally toroidal field of view and therefore not reflect any ultrasound energy that may cause visual obstructions.

One or more processors of controller 204 also may control the ultrasound transducer array of any of the probes in FIGS. 16A-16F to receive ultrasound data in a wide field of view of a region of patient anatomy based at least in part on reflection of the transmitted ultrasound energy. Transducer elements used to transmit the ultrasound energy, may be the same as or different than the transducer elements used to receive the reflected ultrasound energy. In some examples, transducer elements used for transmission and reception may be identical, or be partially overlapping with some transducer elements used for both transmission and reception and some transducer elements used only for transmission and some transducer elements used only for reception, or be mutually exclusive with transducer elements used for transmission and not used for reception and vice versa.

Controller 204, e.g., of guidance workstation 50 or ultrasound workstation 150, may provide excitation signals to the ultrasound transducer array to cause the array to transmit the ultrasound energy, and may include any appropriate electronic circuitry to drive the transducer elements in the array to transmit ultrasound energy and sense ultrasound energy received by the transducer elements in the array. Hence, in some examples, one or more processors of controller 204 may control transducer elements for transmission and reception of ultrasound energy via electronic circuitry. The one or more processors of controller 204 are configured to generate one or more ultrasound images based on the reflected ultrasound energy for output to, and presentation by, display device 110 or 206.

In some examples, controller 204 may control transducer elements to transmit ultrasound energy in a first direction and receive first reflected ultrasound energy in a first field of view. The controller 204 also may be configured to determine that a medical instrument or medical device is causing or is about to cause visual obstructions in reflected ultrasound energy received by the ultrasound transducer array, and steer the transmitted ultrasound energy or focus the received ultrasound energy so as to avoid or mitigate the effects of the visual obstructions. In some examples, the controller 204 may control the transducer array to cease transmitting ultrasound energy in the first direction and begin transmitting ultrasound energy in a second direction. In one example, the second direction may have a wider field of view than the first direction or the field of view of the second direction may have a generally trapezoidal cross-section. In another example, the second direction may have a generally toroidal field of view. As examples, controller 204 may accomplish the steering by mechanically steering the array, or controlling a phased array of transducer elements to steer a beam of transmitted ultrasound energy, and controlling transducer elements to focus reflected ultrasound energy received by the array in a field of view.

Referring back to FIG. 16B, one or more processors of controller 204 may control transducer elements 830 in transducer array 860 to provide a second field of view, such as a wide field of view imaging mode or a toroidal field of view imaging mode, such that the transducer array 860 may transmit ultrasound energy, e.g., pulses of ultrasound energy and may receive reflected ultrasound energy. The wide field of view may be wider and shallower than a field of view in a normal operating mode. The toroidal field of view may be circular with a cavity in the center. In some examples, one or more processors of controller 204 may control a display, such as display device 206 or display device 110, to display a medial-lateral view and/or posterior-anterior view based on the reflected ultrasound energy received by transducer array 860. Each of the transducer elements of FIGS. 16A and 16C-16F may be similarly controlled.

Referring back to FIG. 17A, in one example, a method of operating an ultrasound imaging system with an ultrasound probe having a wide field of view mode or a toroidal field of view mode is now described. One or more processors of controller 204 of ultrasound workstation 150 or guidance workstation 50 may control ultrasound transducer array, such as an ultrasound transducer array described with reference to any of FIGS. 16A-16F, to transmit ultrasound energy (910). In general, the one or more processors associated with controller 204 may control suitable electronic circuitry to provide one or more excitation signals to the ultrasound probe.

Controller 204 then receives reflected ultrasound energy from the ultrasound probe in a first field of view (920). Controller 204 processes the received ultrasound energy and generates one or more ultrasound images based on the received ultrasound energy (930). Such processing may include the processing described herein with respect to other described figures herein. Controller 204, e.g., of ultrasound workstation 150 or guidance workstation 50, may output image data to a display device, such as display device 206 or display device 110, to control the display device to present the one or more ultrasound images (940). The steps in method 900 are not necessarily performed in the order shown in FIG. 16A. As one example, step 940 of outputting image data may be performed independently and out of order with other steps of method 900.

Controller 204, e.g., of ultrasound workstation 150 or guidance workstation 50, may detect whether there is an obstruction in the reflected ultrasound energy, e.g., due to presence of a medical instrument or medical device in the first field of view (950). For example, controller 204 may analyze the first reflected ultrasound energy or one or more ultrasound images generated based on the first reflected ultrasound energy to determine whether there is an obstruction. For example, characteristics such as amplitude, frequency, spectral content or spatial information of ultrasound energy, or similar image information, such as contrast or pixelation, associated with obstruction by a foreign object may provide a signature that sets it apart from obstruction by a natural anatomic object. A medical instrument or medical device will typically include some material, such as metal, that is different from patient bone or tissue. This difference in material may yield different reflective characteristics that may be apparent in reflected ultrasound energy signals or ultrasound image data, for example, based on amplitude, frequency, spectral content, spatial information, contrast or pixelation.

If an obstruction is detected, e.g., in the first reflected ultrasound energy or in the ultrasound image generated based on the first reflected ultrasound energy, e.g., due to a medical instrument or medical device, controller 204 may automatically adjust transmission of ultrasound energy or reception of reflected ultrasound energy (960). For example, controller 204 of ultrasound workstation 150 or guidance workstation 50 may automatically control a transducer array to cease transmitting ultrasound energy in the first direction and may automatically select a wide field of view mode and control a transducer array to transmit second ultrasound energy in a second direction, receive second reflected ultrasound energy in a second field of view, the second field of view being wider than the first field of view. Alternatively, controller 204 of ultrasound workstation 150 or guidance workstation 50 may automatically select a toroidal field of view mode and control a transducer array to transmit second ultrasound energy in a second direction, receive second reflected ultrasound energy in a second field of view, the second field of view being 360 degrees around the medical instrument or medical device. Controller 204 may also dynamically steer the ultrasound energy in response to further obstruction detection due to movement of the medical instrument or device within a region of a patient anatomy.

Figure 24A:
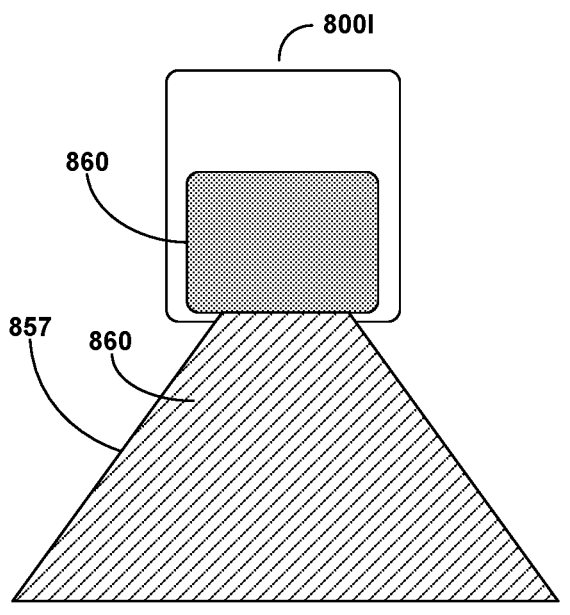
FIGS. 24A and 24B are schematic views of an ultrasound imaging system with a wide field of view in accordance with an example of this disclosure.

FIG. 24A is a schematic view of an ultrasound imaging system with another field of view in accordance with an example of this disclosure. In particular, FIG. 24A shows the use of beamforming to define a generally trapezoidal imaging region for purposes of illustration. Additional imaging geometries may be defined with beamforming depending on the use case. In some examples, the field of view may be considered to be a wide angle field of view, compared to a regular imaging mode in which a more focused or narrow field of view may be used. In the example of FIG. 24A, a probe 8001, which may be the same as or similar to any of the probes of FIGS. 16A-16F, includes an ultrasonic transducer array 860 including a plurality of transducer elements that are controlled by controller 204 to form a wide angle, e.g., generally trapezoidal, field of view. Controller 204 may control the transducer elements with beamforming techniques to transmit ultrasound energy and receive reflected ultrasound energy in field of view 857. In some examples, the transducer array 860 may be controlled such that the field of view 857 is wider than a field of view used in a regular imaging mode. For example, controller 204 may adjust a virtual apex of transducer array 860 to reside behind the face of the transducer array, producing the generally trapezoidal shape of FIG. 24A.

In some examples, a field of view as shown in FIG. 24A may include a region in which a medical instrument or medical device is present, e.g., in a transcatheter mitral valve repair or replacement procedure, but also include regions on different sides of the longitudinal axis of a medical instrument or medical device. In this manner, probe 8001 may permit visualization of anatomy on sides of the medical instrument or medical device that may help in guidance, even though there may be some shadowing caused by the medical instrument or medical device. In some examples, controlling array 860 with beamforming to define a field of view with a generally trapezoidal cross-section, or other selected geometric shapes, may also provide a wider angle, near field view. A generally trapezoidal or other similar geometry may, in some examples, provide a reduced imaging depth with enhanced resolution in the near field when compared to a normal operating mode, such as is shown in FIG. 2. In this case, the field of view may include less of a medical instrument or medical device, and possibly produce less shadow. Additional imaging geometries may be defined with beamforming depending on the use case.

Figure 24B:
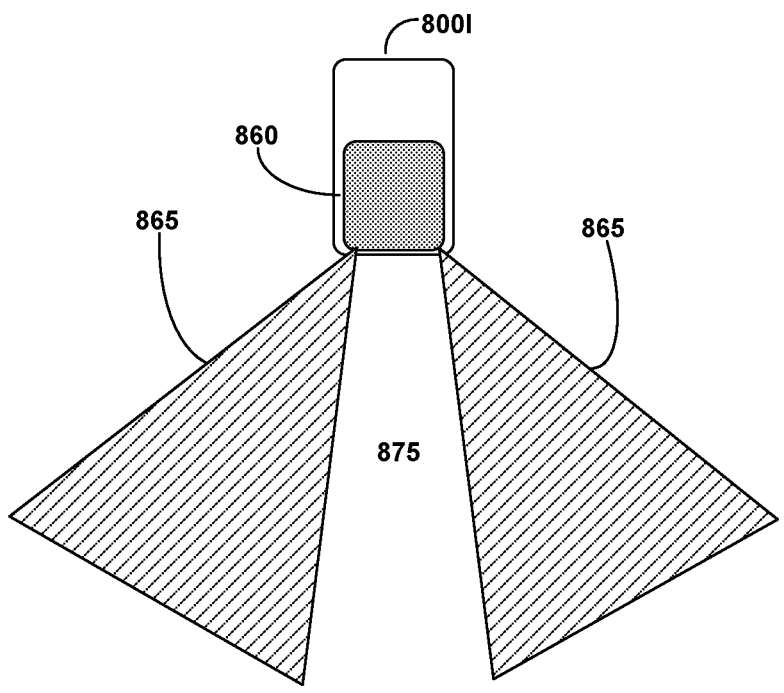

FIG. 24B is a schematic view of an ultrasound imaging system with another field of view in accordance with an example of this disclosure. In particular, FIG. 24B shows the use of beamforming to define a generally toroidal imaging region for purposes of illustration. Additional imaging geometries may be defined with beamforming depending on the use case. In some examples, the field of view may be considered to be a toroidal field of view, compared to a regular imaging mode in which the field of view that is generally more focused and narrow may be used. In the example of FIG. 24B, a probe 8001, which may be the same as or similar to any of the probes of FIGS. 16A-16F, includes an ultrasonic transducer array 860 including a plurality of transducer elements that are controlled by controller 204 to form a generally toroidal field of view. Controller 204 may control the transducer elements with beamforming techniques to transmit ultrasound energy and receive reflected ultrasound energy in field of view 865. In the example of FIG. 24B, the generally toroidal field of view is shown as a cross-section. The field of view 865 makes a 360-degree circle around cavity 875.

In some examples, a field of view as shown in FIG. 24B may not include a region in which a medical instrument or medical device is present, e.g., in a transcatheter mitral valve repair or replacement procedure, but include regions 360 degrees around the medical instrument or medical device. In this manner, probe 8001 may permit visualization of anatomy on sides of the medical instrument or medical device that may help in guidance, while probe 8001 may avoid visual obstructions such as shadowing caused by the medical instrument or medical device. In some examples, controlling array 860 with beamforming to define a field of view with a generally toroidal shape.

Figure 25A:
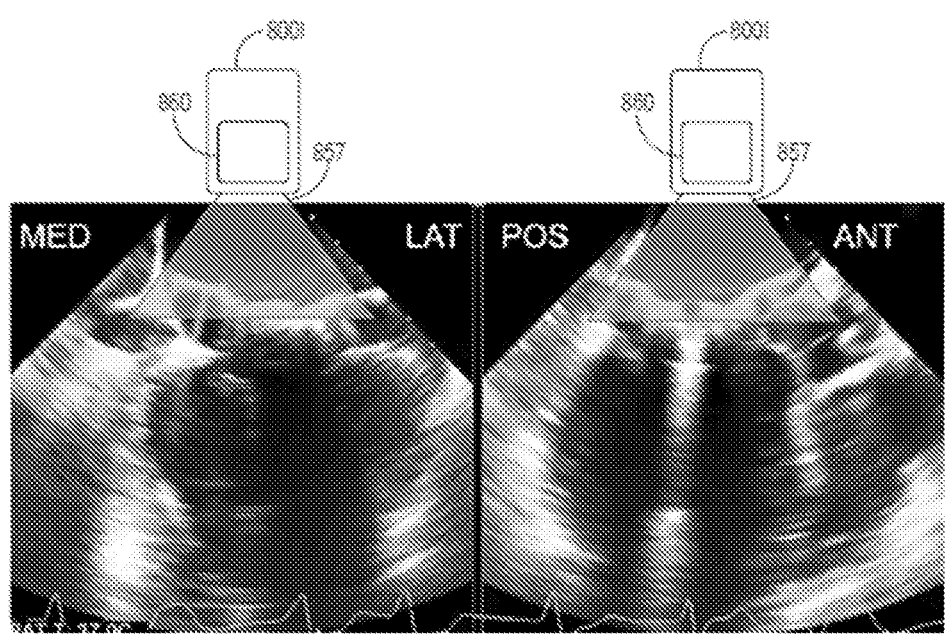
FIGS. 25A and 25B are schematic views of examples of the use of the ultrasound imaging systems of FIGS. 24A and 24B to produce ultrasound images.

FIG. 25A is a schematic medial-lateral (MED-LAT) and posterior-anterior (POS-ANT) view of one example of ultrasound energy that could be produced by an ultrasound imaging system with a generally trapezoidal field of view as described with reference to FIG. 24A. In FIG. 25A, ultrasound probe 8001 is shown with a single beam of ultrasound energy in field of view 857 directed to a portion of a patient's heart for the purposes of heart surgery, such as mitral valve repair or replacement. As with ultrasound probe 800A, ultrasound probe 8001 may be used in other contexts, such as the placement of medical instruments or medical devices, either permanently or temporarily, such as left ventricular assist device (LVAD)s, pacemakers, defibrillators, neurostimulators, muscle stimulators, valves or valve repair or replacement devices, stents, balloons or surgery using ablation or cutting tools, and with other instruments and medical devices described elsewhere in this disclosure. While ultrasound probe 8001 is shown in this example, it could be any of the ultrasound probes of FIG. 16A-16F or another ultrasound probe.

In the example of FIG. 25A, controller 204 controls transducer array 860 to produce a field of view 857 that is generally trapezoidal in cross-section. FIG. 25A depicts two images: a medial-lateral image and a posterior-anterior image. To form a beam of ultrasound energy with a desired shape, controller 204 may control transducer elements to have a virtual apex of ultrasound energy that is be behind the outer face of the plurality of ultrasound transducer elements 830 in transducer array 860. For example, controller 204 could control the depth of the ultrasound energy to select field of view 857 by changing which of the plurality of ultrasound transducer elements are receiving excitation signals. A shallower shape, such as a shape with a generally trapezoidal cross-section, may be desirable to avoid or mitigate visual obstructions that may appear with deeper fields of view. Also, in some examples, a field of view with a generally trapezoidal cross-section or other similar geometry may provide a reduced imaging depth with enhanced resolution in the near field. Other shapes of ultrasound energy could be utilized through beamforming.

Figure 25B:
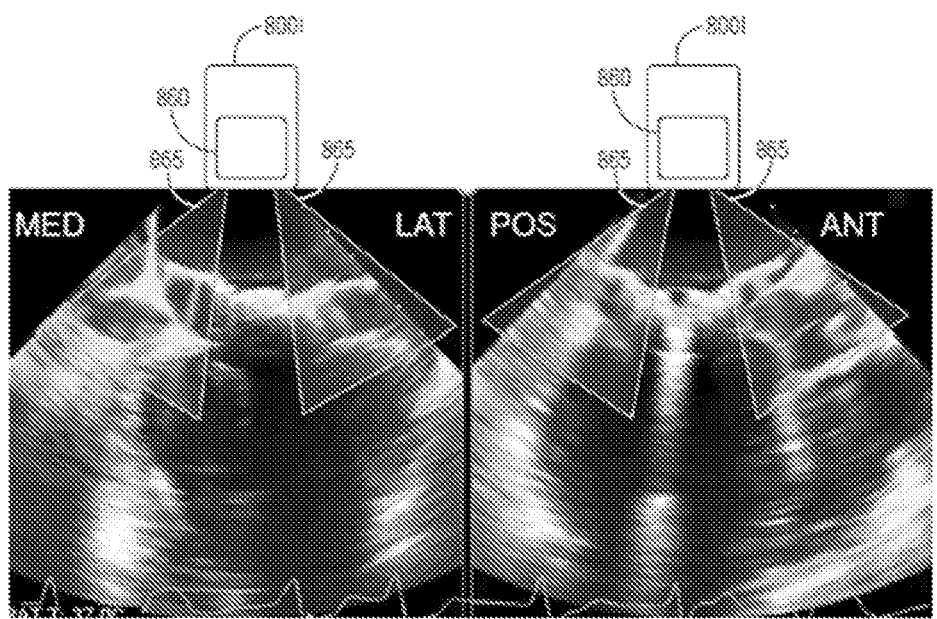

FIG. 25B is a schematic medial-lateral (MED-LAT) and posterior-anterior (POS-ANT) view of one example of ultrasound energy that could be produced by an ultrasound imaging system with a generally toroidal field of view as described with reference to FIG. 24B. In FIG. 25B, ultrasound probe 8001 is shown with a cross-section of single beam of ultrasound energy in field of view 865 directed to a patient's heart for the purposes of heart surgery, such as mitral valve repair or replacement. As with ultrasound probe 800A, ultrasound probe 8001 may be used in other contexts, such as the placement of medical instruments or medical devices, either permanently or temporarily, such as left ventricular assist device (LVAD)s, pacemakers, defibrillators, neurostimulators, muscle stimulators, valves or valve repair or replacement devices, stents, balloons or surgery using ablation or cutting tools, and with other instruments and medical devices described elsewhere in this disclosure. While ultrasound probe 8001 is shown in this example, it could be any of the ultrasound probes of FIGS. 16A-16F or another ultrasound probe. In the example of FIG. 25B, controller 204 controls transducer array 860 to produce a field of view 865 that is generally toroidal in shape, e.g., in other words generally circular with a cavity. For instance, the clinician may navigate a catheter loaded with a replacement mitral valve into place by seeing the image of the anatomical structure on all sides of the existing mitral valve.

Controller 204 may periodically or continually steer or adjust the steering (e.g., angle, direction or field of view) or shape of ultrasound energy transmitted and received by array 860 to avoid or mitigate obstruction caused by the presence of medical instruments or medical devices. Notably, a medical instrument or medical device may move within a region of the patient, presenting a movable source of obstruction for ultrasound imaging and guidance. As the instrument or device moves in the imaging region, it may transition from not causing obstruction to causing substantial obstruction in ultrasound images, or the area that is obstructed from view may move as the device is moved within the patient. Accordingly, it may be desirable to detect obstruction and adjust or select an ultrasound imaging mode to eliminate or mitigate the resulting obstruction. For example, controller 204 may detect an obstruction based on characteristics in reflected ultrasound energy, in an ultrasound image based on the reflected ultrasound energy or both as discussed above. As a medical instrument or medical device moves within an imaging region, controller 204 may detect obstruction and control array 860 to automatically steer and focus ultrasound energy to define a different field of view that does not include the medical instrument or medical device or, alternatively, does not present significant obstruction.

Each time that obstruction is detected, either by a user or automatically by controller 204, the controller may update the steering or shape of ultrasound energy to include a different field of view (or views) that avoids the medical instrument or medical device or, alternatively, does not present significant obstruction. This process may continue on an iterative basis so that system 10 may generally avoid generating images with obstruction. In some examples, controller 204 may continue to steer among different positions or shapes until an obstruction is eliminated or mitigated. In some examples, the different positions may be specified by a predefined set or sequence of positions of fields of view. Alternatively, the different positions may be selected based on the output of a machine learning algorithm that generates field of view positions for steering based on spatial or other characteristics of the obstruction, e.g., as indicated by analysis of received ultrasound energy or ultrasound images produced based on the ultrasound energy.

In some examples, the ultrasound imaging system may be configured to automatically steer the transmitted ultrasound energy and receive the reflected ultrasound energy in the field of view to avoid or mitigate the effects of visual obstruction, such as shadowing, caused by the medical instrument or medical device. For example, with machine learning, data sets indicative of the time immediately before a medical instrument or medical device causes visual obstructions and when the medical instrument or medical device begins causing visual obstructions may be analyzed to determine one or more characteristics of reflected ultrasound energy, or ultrasound images formed from reflected ultrasound energy, that are indicative of the beginning of such visual obstructions. For example, characteristics such as amplitude, frequency, spectral content or spatial information of ultrasound energy, or similar image information, such as contrast or pixelation, associated with obstruction by a foreign object may provide a signature that sets it apart from obstruction by a natural anatomic object. A medical instrument or medical device will typically include some material, such as metal, that is different from patient bone or tissue. This difference in material may yield different reflective characteristics that may be apparent in reflected ultrasound energy signals or ultrasound image data, for example, based on amplitude, frequency, spectral content, spatial information, contrast or pixelation.

The one or more processors of controller 204 may be configured to monitor for those determined characteristics in the reflected ultrasound energy or the ultrasound image to detect the onset of visual obstructions and, when obstruction or onset of obstruction is detected, automatically select a different imaging mode, e.g., split aperture or wide angle, or otherwise beam steer to avoid or mitigate the visual obstructions or begin displaying a reference image. In some examples, the ultrasound imaging system may provide a notification that a visual obstruction has been detected. This notification may be visual, audible, tactile, or the like and may be sent to a notification device, such as display device 110, display device 206, ultrasound workstation 150, computing system 100, ultrasound imager 140, ultrasound imager 142 or a speaker (not shown).

Figure 26:
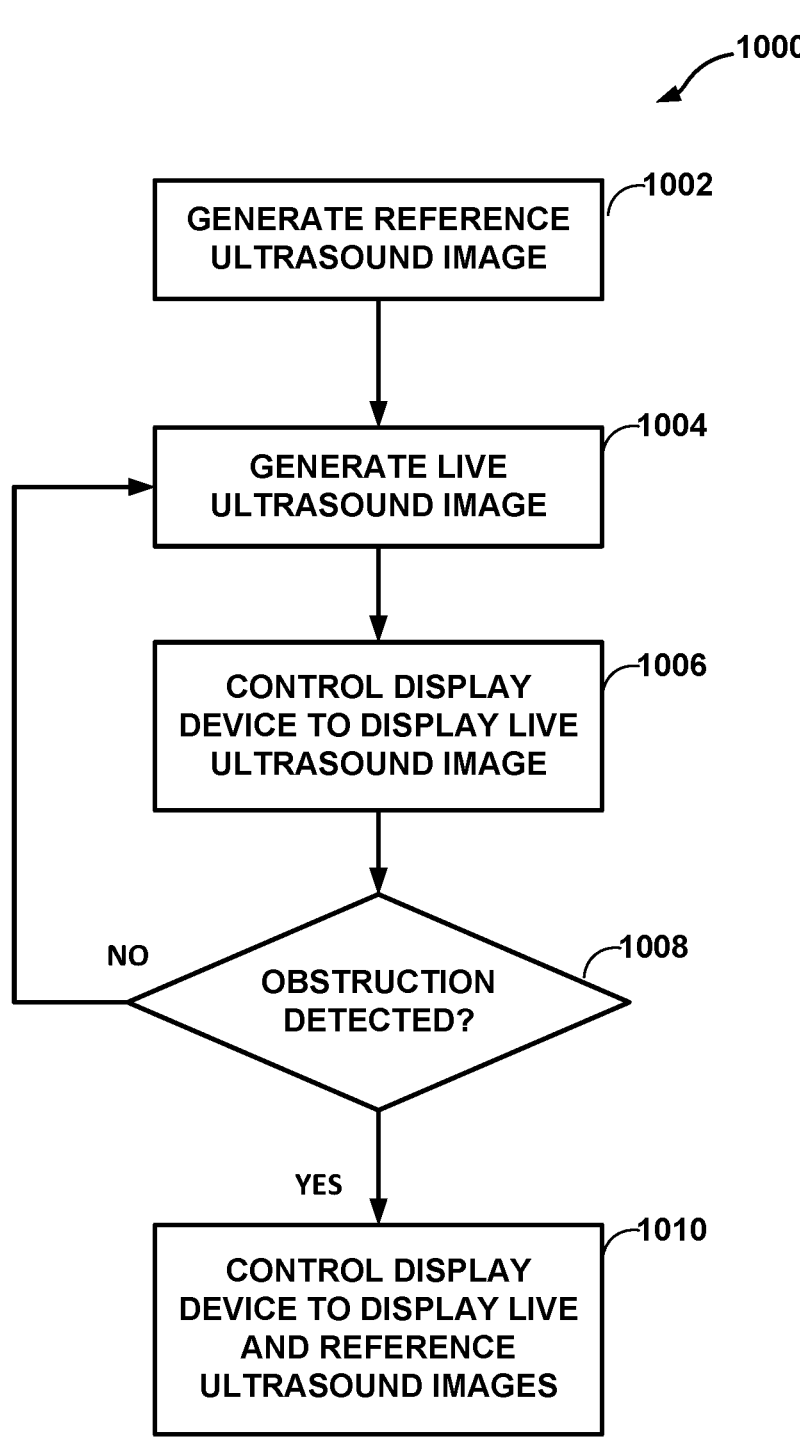
FIG. 26 is a flowchart of an example of automatically presenting a reference ultrasound image and a live ultrasound image upon detecting an obstruction.

FIG. 26 is a flowchart of an example (1000) of presenting a reference ultrasound image and a live ultrasound image upon detecting an obstruction caused by a medical instrument or medical device. As shown in FIG. 26, system 10 may generate a reference ultrasound image (1002). For example, controller 204 of ultrasound workstation 150 or guidance workstation 50 may control ultrasound transmit ultrasound imager 140 or 142 to transmit ultrasound energy. Ultrasound imager 140 or 142 may receive ultrasound energy reflected in the region of the patient. Ultrasound workstation 150 or guidance workstation 50 may generate a reference image based on the received reflected ultrasound energy prior to a medical instrument or medical device causing obstruction in the received ultrasound energy. In some examples, ultrasound workstation 150 or guidance workstation 50 may generate multiple reference images. In some examples, ultrasound workstation 150 or guidance workstation 50 may generate a reference image of a full cycle of a moving anatomical structure. In some examples, ultrasound workstation 150 or guidance workstation 50 may generate a reference image that is a motion picture loop.

Ultrasound workstation 150 or guidance workstation 50 may generate a live ultrasound image of a region of the patient (1004). For example, controller 204 of ultrasound workstation 150 or guidance workstation 50 may generate an ultrasound image of a region of the patient in real-time. Controller 204 may control display device 110 or display device 206 to display the live ultrasound image (1006). Controller 204 may then automatically detect an obstruction caused by a medical instrument or medical device (1008). For example, controller 204 may analyze amplitude, frequency or spatial information associated with the received ultrasound energy to detect information that correlates with obstruction such as shadowing or other artifacts. Alternatively, controller 204 may analyze pixel, voxel or other image information, e.g., amplitude or intensity information, within an image generated based on the received ultrasound energy to detect information that correlates with obstruction such as shadowing or other artifacts. In some examples, controller 204 may be configured to apply machine learning to match characteristics of the received energy or the generated image with characteristics known to correlate with presence of obstruction, such as shadowing or other artifacts.

If no obstruction is detected (the "NO" path in FIG. 26), controller 204 of ultrasound workstation 150 or guidance workstation 50 may continue to generate and display the live ultrasound image of a region of the patient (1004 and 1006). If an obstruction is detected (the "YES" path in FIG. 26), controller 204 of ultrasound workstation 150 or guidance workstation 50 may control display device 110 or display device 206 to display both the reference ultrasound image and the live ultrasound image (1010). In some examples, controller 204 may register the reference ultrasound image and the live ultrasound image as discussed above with respect to FIGS. 12-15.

Referring back to FIG. 17A, instructions for causing one or more processors of controller 204 to control the ultrasound probe to automatically avoid visual obstructions caused by a medical instrument or medical device may be part or all of application 216 stored in memory 202 and the one or more processors of controller 204 acting on those instructions may execute this method. In other examples, controller 204 may be one or more processors arranged as fixed function circuitry or a combination of programmable and fixed function circuitry. In various examples, the ultrasound probe to be controlled could be a probe 800A, 800B, 800D, 800F, as described herein. For example, one or more processors of controller 204 of ultrasound workstation 150 or guidance workstation 50 may automatically control ultrasound transducer array, such as an ultrasound transducer array described with reference to any of FIGS. 16A-16F, to transmit ultrasound energy (910). In general, the one or more processors associated with controller 204 may control suitable electronic circuitry to provide one or more excitation signals to the ultrasound probe.

Controller 204 may receive reflected ultrasound energy from the ultrasound probe in a field of view (920). Controller 204 processes the received ultrasound energy and generates one or more ultrasound images based on the received ultrasound energy (930). Such processing may include the processing described herein with respect to other described figures herein. Controller 204, e.g., of ultrasound workstation 150 or guidance workstation 50, may output image data to a display device, such as display device 206 or display device 110, to control the display device to present the one or more ultrasound images (940). As mentioned above, the steps in method 900 are not necessarily performed in the order shown in FIG. 17A. As one example, step 940 of outputting image data may be performed independently and out of order with other steps of method 900.

Controller 204, e.g., of ultrasound workstation 150 or guidance workstation 50, may detect whether there is an obstruction in the reflected ultrasound energy, e.g., due to presence of a medical instrument or medical device in the field of view (950). For example, controller 204 may analyze the reflected ultrasound energy or one or more ultrasound images generated based on the reflected ultrasound energy to determine whether there is an obstruction. If an obstruction is detected, e.g., in the reflected ultrasound energy or in the ultrasound image generated based on the reflected ultrasound energy, e.g., due to a medical instrument or medical device, controller 204 may automatically adjust transmission of ultrasound energy or reception of reflected ultrasound energy (960). For example, controller 204 of ultrasound workstation 150 or guidance workstation 50 may automatically overlay, underlay or otherwise present a reference image with a live image on display device 110 or 206. Alternatively, controller 204 may steer the ultrasound energy to a region away from the area in which a medical instrument or medical device is causing obstruction in such a way as to mitigate or avoid the visual obstruction. As another alternative, controller 204 may select a split aperture and control a transducer array to operate in the split aperture mode, as describe in this disclosure. As yet another alternative, controller 204 may control a transducer array to operate in a wide field of view mode. In still a further alternative, controller 204 may control a transducer array to operate in a toroidal field of view mode. Controller 204 may also automatically and dynamically steer the ultrasound energy in response to further obstruction detection due to movement of the medical instrument or device within a region of a patient anatomy. Controller 204 may also or alternatively send a notification to a notification device as discussed above.

Referring back to FIG. 17B, instructions for causing one or more processors of controller 204, e.g., of guidance workstation 50 or ultrasound workstation 150, to automatically control the ultrasound probe may be part or all of application 216 stored in memory 202 and the one or more processors of controller 204 acting on those instructions could execute this method. In other examples, controller 204 could be one or more processors arranged as fixed function circuitry or a combination of programmable and fixed function circuitry. In various examples, the ultrasound probe to be controlled could be a probe 800A, 800B, 800D, 800F, as described herein. For example, one or more processors of controller 204 may control the ultrasound transducer array of the ultrasound probe, such as an ultrasound transducer array described with reference to any of FIGS. 16A-16F, to automatically transmit first ultrasound energy in a first direction (970). Controller 204 may accomplish this by providing one or more excitation signals to the ultrasound transducer array of the ultrasound probe. Controller 204 may control the ultrasound transducer array to automatically transmit second ultrasound energy in a second direction (972). Again, controller 204 may accomplish this by providing one or more excitation signals to selected transducer elements of the ultrasound transducer array of the ultrasound probe.

Controller 204 may control the ultrasound transducer array to automatically receive first reflected ultrasound energy in a first field of view of a region of patient anatomy based at least in part on reflection of the first transmitted ultrasound energy (974). In addition, controller 204 may control the ultrasound transducer array to automatically receive second reflected ultrasound energy in a second field of view (976). As further shown in FIG. 17B, controller 204 may generate one or more ultrasound images based on the received ultrasound energy (978).

Controller 204, e.g., of guidance workstation 50 or ultrasound workstation 150, may automatically control the transducer array, according to a split aperture mode, so that the reflected ultrasound energy received in the first and second fields of view are not obstructed, e.g., by the presence of a medical instrument or medical device that reflects the transmitted ultrasound energy. Rather, in some examples, the first and second fields of view may be selected, in some examples, to include areas at different sides of a longitudinal axis of a medical instrument or medical device, and exclude an area in which the medical instrument or medical device resides. In other examples, the first and second field may be selected to include areas at different sides of a longitudinal axis of a medical instrument or medical device, and also include an area in which the medical instrument or medical device resides.

Hence, one or more processors of controller 204 may control the ultrasound transducer array to automatically transmit and receive ultrasound energy such that the first field of view is selected to include a first portion of the region of the patient anatomy on a first side of the longitudinal axis of a medical instrument or medical device when the medical instrument or medical device is introduced into the region of the patient anatomy and the second field of view is selected to include a second portion of the region of the patient anatomy on a second side of the longitudinal axis of a medical instrument or medical device when the medical instrument or medical device is introduced into the region of the patient anatomy. For this method, controller 204 may automatically control transducer elements in a single transducer array, transducer elements in two, separate transducer arrays, or transducer elements forming subsets of a single transducer array, e.g., as described with reference to probes 800A, 800B, 800D, 800F (FIGS. 16A-16F).

FIGS. 27A, 27B, 27C and 27D are schematic views of different example modes of operation of an ultrasound imaging system to produce ultrasound images when a medical instrument or medical device is causing obstruction of reflected ultrasound energy in a field of view. While ultrasound probe 800B is shown, the ultrasound probe may alternatively be any of ultrasound probe 800A, 800D or 800F. Ultrasound probe 800B may be part of or all of ultrasound imager 140 or 142 of FIGS. 3A and 3B.

In the example of FIG. 27A, controller 204, e.g., of guidance workstation 50 or ultrasound workstation 150, controls ultrasound transducer array 860 in a regular mode that produces an obstructed region 986. As shown in FIG. 27A, however, the presence of medical instrument 988 may cause visual obstructions such as shadowing, resulting in obstructed region 986. In this case, controller 204 may control transducer array 860 to automatically transition from the regular imaging mode to a different imaging mode selected to avoid or mitigate the effects of obstruction caused by medical instrument 988.

Controller 204 may, in some examples, select the different imaging mode in response to detection of an obstructed region. Controller 204 may automatically detect the presence of an obstructed region, e.g., by analyzing one or more characteristics of received ultrasound energy indicative of obstruction or by analyzing an image or images produced based on the received ultrasound energy.

For example, controller 204 may analyze amplitude, frequency or spatial information associated with the received ultrasound energy to detect information that correlates with obstruction such as shadowing or other artifacts. Alternatively, controller 204 may analyze pixel, voxel or other image information, e.g., amplitude or intensity information, within an image generated based on the received ultrasound energy to detect information that correlates with obstruction such as shadowing or other artifacts. In each case, in some examples, controller 204 may be configured to apply machine learning to match characteristics of the received energy or the generated image with characteristics known to correlate with presence of obstruction, such as shadowing or other artifacts.

In some examples, machine learning or other tools, which may be part of application 216 in memory 202, may be used to automatically distinguish between obstruction caused by natural anatomy, such as bone, and obstruction caused by foreign objects such as medical instruments or medical devices. Controller 204 may distinguish between characteristics of ultrasound energy, or characteristics of ultrasound image data, indicative of obstruction by natural anatomy or foreign objects. For example, characteristics such as amplitude, frequency, spectral content or spatial information of ultrasound energy, or similar image information, such as contrast or pixelation, associated with obstruction by a foreign object may provide a signature that sets it apart from obstruction by a natural anatomic object. A medical instrument or medical device will typically include some material, such as metal, that is different from patient bone or tissue. This difference in material may yield different reflective characteristics that may be apparent in reflected ultrasound energy signals or ultrasound image data, for example, based on amplitude, frequency, spectral content, spatial information, contrast or pixelation.

In the case of obstruction caused by foreign object such as medical instrument or medical device, controller 204 may notify a user of the source of obstruction, e.g., via a display or audible message, and may automatically select a different imaging mode or steer an ultrasound beam or beams to avoid or mitigate obstruction caused by the foreign object, or automatically overlay, underlay or otherwise present a reference image with a live image on display device 110 or 206. In the case of obstruction caused by natural anatomy, such as bone, controller 204 may notify a user of the source of obstruction, e.g., via a display or audible message, but take no action to select a different imaging mode or steer an ultrasound beam or beams, or automatically overlay, underlay or otherwise present a reference image with a live image on display device 110 or 206, as the natural anatomy may be considered a legitimate part of the image. In other examples, even in the case of natural anatomy, it may be desirable for controller 204 to automatically select a different imaging mode or steer an ultrasound beam or beams to avoid or mitigate obstruction caused by natural anatomic object, or automatically overlay, underlay or otherwise present a reference image with a live image on display device 110 or 206.

Upon automatic detection of obstruction, controller 204 may automatically select a different imaging mode to avoid or mitigate the effects of obstruction in images generated by system 10. As shown in FIGS. 27A-27D, for example, upon detection of obstruction, controller 204 may stop using a first, e.g., regular mode of imaging, and instead start to use a different mode, such as a split aperture imaging mode, e.g., as shown in FIG. 27B and described elsewhere in this disclosure, a wide field of view imaging mode where the field of view has a generally trapezoidal cross-section, e.g., as shown in FIG. 27C and described elsewhere in this disclosure, a toroidal field of view imaging mode where the field of view has a generally toroidal shape, e.g., as shown in FIG. 27D, or a dynamic steering imaging mode, e.g., as described in this disclosure with reference to FIGS. 22 and 23.

To steer transmitted stimulation energy in selected directions and define fields of view to receive reflected energy, as described in this disclosure, to thereby avoid or minimize obstructions caused by medical instruments or medical devices, controller 204 may be configured to apply any of a variety of well-known beamforming techniques established in the art. Some example ultrasound beamforming techniques are described, for example, in U.S. Pat. No. 5,322,068, issued Jun. 21, 1994, to Thiele et al., entitled "Method and apparatus for dynamically steering ultrasonic phased arrays," and U.S. Patent Application Publication No. 20180085096, to Brandl, entitled "Method and systems for adjusting a field of view for medical imaging systems," published Mar. 29, 2018.

In some examples, the controller 204 of system of FIG. 3A or FIG. 3B may overlay, underlay, merge or otherwise present one or more reference images of the target region of the patient with one or more live ultrasound images from the imaging system of the target region of the patient. In one or more examples, the controller is adapted to overlay, underlay, merge or otherwise present the reference image with the current, i.e., live, image such that the reference image is dynamic with the live image. In other words, the reference image is overlaid, underlaid, merged or otherwise presented with the current, live image such that the reference image moves in registration with the live image in the display. In some examples, the reference image(s) is a motion picture of a full cycle of a moving anatomical structure, such as a heart.

In some examples, each of the ultrasound transducer arrays described in this disclosure, such as the ultrasound transducer subsets or arrays described with reference to FIGS. 16A-16F, may be a phased array of transducer elements. Controller 204 may activate individual transducer elements of the phased array with controlled delays to control an angle and focus to steer pulses of ultrasound energy in a particular direction. In this manner, in a split aperture mode or a non-split aperture mode, controller 204 may control transducer elements in a first transducer subset or transducer array to transmit ultrasound energy in a first direction and control transducer elements in a second transducer subset or transducer array to transmit ultrasound energy in a second direction. The phased arrays may be controlled, in the split aperture mode, to target areas on different sides of a medical instrument or medical device in a region of interest, to avoid or mitigate effects of obstruction caused by reflections from the medical instrument or medical device.

Controller 204 also may control transducer elements in a subset or array of transducer elements to receive ultrasound energy in a desired field of view, e.g., based on adjustment of a virtual apex of virtual scan line of the field of view. For example, in a non-split aperture mode, controller 204 may control the virtual apex for the array of transducer elements to receive ultrasound energy in a field of view and adjust the virtual apex dynamically to change the field of view to avoid or mitigate the effects of obstruction caused by reflections from the medical instrument or medical device. Controller 204 may detect the obstruction based on characteristics in reflected ultrasound energy, in an ultrasound image based on the reflected ultrasound energy or both. The dynamic change to the field of view may be done while the medical instrument or device is moving so as to continuously avoid or mitigate the effects of obstruction caused by reflections from the medical instrument or medical device.

Controller 204 also may control transducer elements in a subset or array of transducer elements to receive ultrasound energy in a desired field of view, e.g., based on adjustment of a virtual apex of virtual scan line of the field of view. For example, in a split aperture mode, controller 204 may control the virtual apex for a first subset or array of transducer elements to receive ultrasound energy in a first field of view and control the virtual apex for a second subset or array of transducer elements to receive ultrasound energy in a second field of view different than the first field of view. The virtual apex, in each case, may be adjusted so that the respective fields of view include different sides of a longitudinal axis of a medical instrument or medical device in a region of interest, to avoid or mitigate the effects of obstruction caused by reflections from the medical instrument or medical device.

The virtual scan line may extend from a virtual apex located off the face of the transducer array, e.g., behind the face of the transducer array. Locating the virtual apex behind the face of the transducer array may provide a wider near field of view. Accordingly, for a wide angle mode such as a mode providing a field of view with a generally trapezoidal cross-section, in some examples, controller 204, e.g., of ultrasound workstation 150 or ultrasound imager 140 or 142, may control the virtual apex to be positioned behind the face of the pertinent transducer array. The virtual apex could also be shifted laterally by controller 204 to move the ultrasound energy around the medical instrument or medical device.

Controller 204 may, for example, control transducer array 860 to shut off transducer(s) located at or near the middle of transducer array 860 so as to generate a toroidal field of view. Controller 204 may adjust the transducer(s) that are shut off so that the field of view surrounds the a medical instrument or medical device, with the medical instrument or medical device being within the cavity of the toroidal field of view in a region of interest, to avoid or mitigate the effects of obstruction caused by reflections from the medical instrument or medical device.

The above techniques also may be used to dynamically steer ultrasound energy, e.g., automatically upon detection of an obstruction. Other techniques may be used alternatively or in combination with the above techniques of phased array steering and virtual apex adjustment to support dynamic steering, steering for split aperture mode, steering for wide angle mode, and steering for toroidal mode, including the control of aperture size and shape by selection of particular transducers to be activated, to optimize or dynamically adjust scan angle, direction, depth or field of view.

Various aspects of the techniques of this disclosure may enable one or more of the devices described above to perform the examples listed below.

Example 1. A system comprising: an ultrasound sensor configured to transmit ultrasound energy and receive ultrasound energy reflected in a region of a patient; and one or more processors configured to: generate a reference ultrasound image of the region of the patient based on a portion of the ultrasound energy that was received by the ultrasound sensor prior to a medical instrument or medical device causing obstruction in the received ultrasound energy; generate a live ultrasound image based on a current portion of the received ultrasound energy obtained by the ultrasound sensor; register the reference ultrasound image and the live ultrasound image; and control a display device to display the reference ultrasound image with at least a portion of the live ultrasound image.

Example 2. The system of example 1, wherein the one or more processors are configured to: receive EM tracking data from an EM tracking system; determine at least one of a position, orientation or trajectory of the medical instrument or medical device based on the EM tracking data; and generate a representation of the medical instrument or medical device based on the determined position, orientation or trajectory.

Example 3. The system of example 1 or example 2, wherein the portion of the received ultrasound energy received by the ultrasound sensor prior to the medical instrument or medical device causing the obstruction was received when the medical instrument or medical device was at least partially positioned within the region of the patient.

Example 4. The system of any combination of examples 1-3, wherein the portion of the received ultrasound energy received by the ultrasound sensor prior to the medical instrument or medical device causing the obstruction was received before the medical instrument or medical device was at least partially positioned within the region of the patient.

Example 5. The system of any combination of examples 1-4, wherein the reference ultrasound image includes a plurality of reference ultrasound images, and the one or more processors are configured to receive event data, select one of the reference ultrasound images based on correspondence with the event data, and control the display device to display the selected ultrasound image with the at least a portion of the live ultrasound image.

Example 6. The system of example 5, wherein the event data comprises cardiac event data.

Example 7. The system of example 6, wherein the cardiac event data includes a phase of a cardiac cycle, and the selected reference ultrasound image corresponds to the phase of the cardiac cycle.

Example 8. The system of example 7, wherein the one or more processors are configured to determine the phase of the cardiac cycle based on at least one of an ECG signal or the live ultrasound image.

Example 9. The system of any combination of examples 1-8, wherein the reference ultrasound image includes a plurality of reference ultrasound images, and the one or more processors are configured to: select one of the reference ultrasound images based on one of a spatial orientation of the live ultrasound image; and control the display device to display the at least a portion of the live ultrasound image with the selected reference ultrasound image.

Example 10. The system of example 9, wherein each of the reference ultrasound images corresponds to one of the spatial orientations of the live ultrasound image, and each of the spatial orientations includes at least one of a translation, rotation, or perspective of the live ultrasound image.

Example 11. The system of example 9, wherein the reference ultrasound image includes a plurality of reference ultrasound images, and the one or more processors are configured to receive event data, select one of the reference ultrasound images based on both the event data and one of a spatial orientations of the live ultrasound image, and control the display device to display the selected ultrasound image with the live ultrasound image.

Example 12. The system of any combination of examples 1-11, wherein the medical instrument or medical device comprises at least one of an implantable medical device, medical implant delivery device, therapy delivery device, surgical device, mechanical circulatory support device, coronary stent device, heart valve device, heart valve repair device, cardiac ablation device, cardiac lead device, drug delivery device, catheter delivery device, or endoscopic delivery device.

Example 13. The system of any combination of examples 1-12, wherein the medical instrument or medical device comprises a medical instrument configured for transcatheter heart valve repair or replacement.

Example 14. The system of any combination of examples 1-13, wherein the medical instrument or medical device further comprises a prosthetic heart valve.

Example 15. The system of example 14, wherein the prosthetic heart valve comprises a prosthetic mitral valve.

Example 16. The system of any combination of examples 1-15, wherein the one or more processors are configured to control the display device to display the reference ultrasound image with a representation of the medical instrument or medical device.

Example 17. The system of any combination of examples 1-16, wherein the one or more processors are configured to identify a physiological landmark of the region of the patient based on the live ultrasound image and register the reference ultrasound image with the physiological landmark.

Example 18. The system of any combination of examples 1-17, wherein the one or more processors are configured to control the display device to display the at least a portion of the live ultrasound image with the reference ultrasound image such that the reference ultrasound image moves in registration with the at least a portion of the live ultrasound image.

Example 19. The system of any combination of examples 1-18, wherein the one or more processors are further configured to: determine that at least one of a position, orientation, or trajectory of the medical instrument or medical device has changed; and control the display device to display at least one of an updated position, orientation, or trajectory of the medical instrument or medical device based on the determination that at least one of the position, orientation, or trajectory has changed.

Example 20. The system of any combination of examples 1-19, wherein the one or more processors are configured to control the display device to display the reference ultrasound image with a representation of the medical instrument or medical device.

Example 21. The system of any combination of examples 1-20, further comprising: an electromagnetic (EM) tracking system configured to collect EM tracking data representative of a position or orientation of each of the ultrasound sensor and the medical instrument or medical device relative to the region of the patient, wherein the one or more processors are further configured to: receive the EM tracking data from the EM tracking system; determine at least one of a position, orientation, or trajectory of the medical instrument or medical device based on the EM tracking data; and control the display device to display at least one of the position, orientation, or trajectory of the medical instrument or medical device with the reference ultrasound image.

Example 22. The system of any combination of examples 1-21, wherein the reference ultrasound image comprises a motion picture covering a full-cycle of a moving anatomical structure.

Example 23. The system of example 22, wherein moving anatomical structure is a heart.

Example 24. The system of any combination of examples 1-23, wherein the one or more processors are further configured to identify common anatomical structures in the reference ultrasound image and the live ultrasound image using image recognition prior to registering the reference ultrasound image and the live ultrasound image.

Example 25. A method comprising: transmitting ultrasound energy; receiving ultrasound energy reflected in a region of a patient; generating a reference ultrasound image of the region of the patient based on a portion of the received ultrasound energy that was received prior to a medical instrument or medical device causing obstruction in the received ultrasound energy; generating a live ultrasound image based on a current portion of the received ultrasound energy; registering the reference ultrasound image and the live ultrasound image; and controlling a display device to display the reference ultrasound image with at least a portion of the live ultrasound image.

Example 26. The method of example 25, further comprising: receiving EM tracking data from an EM tracking system; determining at least one of a position, orientation or trajectory of the medical instrument or medical device based on the EM tracking data; and generating the representation of the medical instrument or medical device based on the determined position, orientation or trajectory.

Example 27. The method of example 25 or 26, wherein the portion of the received ultrasound energy received by the ultrasound sensor prior to the medical instrument or medical device causing the obstruction was received when the medical instrument or medical device was at least partially positioned within the region of the patient.

Example 28. The method of any combination of examples 25-27, wherein the portion of the received ultrasound energy received by the ultrasound sensor prior to the medical instrument or medical device causing the obstruction was received before the medical instrument or medical device was at least partially positioned within the region of the patient.

Example 29. The method of any combination of examples 25-28, wherein the reference ultrasound image includes a plurality of reference ultrasound images, the method further comprising receiving event data, selecting one of the reference ultrasound images based on correspondence with the event data, and controlling the display device to display the selected ultrasound image with the at least a portion of the live ultrasound image or the representation of the medical instrument or medical device.

Example 30. The method of example 29, wherein the event data comprises cardiac event data.

Example 31. The method of example 30, wherein the cardiac event data includes a phase of a cardiac cycle, and the selected reference ultrasound image corresponds to the phase of the cardiac cycle.

Example 32. The method of example 31, further comprising determining the phase of the cardiac cycle based on at least one of an ECG signal or the live ultrasound image.

Example 33. The method of any combination of examples 25-32, wherein the reference ultrasound image includes a plurality of reference ultrasound images, the method further comprising selecting one of the reference ultrasound images based on one of a plurality of spatial orientations of the live ultrasound image, and controlling the display device to display the at least a portion of the live ultrasound image with the selected reference ultrasound image.

Example 34. The method of example 33, wherein each of the reference ultrasound images corresponds to one of the plurality of spatial orientations of the live ultrasound image, and wherein each of the spatial orientations includes at least one of a translation, rotation, or perspective of the live ultrasound image.

Example 35. The method of any combination of examples 25-34, wherein the reference ultrasound image includes a plurality of reference ultrasound images, the method further comprising receiving event data, selecting one of the reference ultrasound images based on both the event data and one of a plurality of spatial orientations of the live ultrasound image, and controlling the display device to display the selected ultrasound image with the least a portion of the live ultrasound image.

Example 36. The method of any combination of examples 25-35, wherein the medical instrument or medical device comprises at least one of an implantable medical device, medical implant delivery device, therapy delivery device, surgical device, mechanical circulatory support device, coronary stent device, heart valve device, heart valve repair device, cardiac ablation device, cardiac lead device, drug delivery device, catheter delivery device, or endoscopic delivery device.

Example 37. The method of any combination of examples 25-36, wherein the medical instrument or medical device comprises an instrument configured for transcatheter heart valve repair or replacement.

Example 38. The method of any combination of examples 25-37, wherein the medical instrument or medical device further comprises a prosthetic heart valve.

Example 39. The method of example 38, wherein the prosthetic heart valve comprises a prosthetic mitral valve.

Example 40. The method of any combination of examples 25-39, further comprising controlling the display device to display the reference ultrasound image with the representation of the medical instrument or medical device.

Example 41. The method of any combination of examples 25-40, further comprising identifying a physiological landmark of the region of the patient based on the live ultrasound image and registering the reference ultrasound image with the physiological landmark.

Example 42. The method of any combination of examples 25-41, further comprising controlling the display device to display the at least a portion of the live ultrasound image with the reference ultrasound image such that the reference ultrasound image moves in registration with the at least a portion of the live ultrasound image.

Example 43. The method of any combination of examples 25-42, further comprising: determining that at least one of a position, orientation, or trajectory of the medical instrument or medical device has changed; and controlling the display device to display at least one of an updated position, orientation, or trajectory of the medical instrument or medical device based on the determination that at least one of the position, orientation, or trajectory has changed.

Example 44. The method of any combination of examples 25-43, further comprising controlling the display device to display the reference ultrasound image with the representation of the medical instrument or medical device.

Example 45. The method of any combination of examples 25-44, further comprising: collecting EM tracking data representative of a position or orientation of each of the ultrasound sensor and the medical instrument or medical device relative to the region of the patient; receiving the EM tracking data from the EM tracking system; determining at least one of a position, orientation, or trajectory of the medical instrument or medical device based on the EM tracking data; and controlling the display device to display at least one of the position, orientation, or trajectory of the medical instrument or medical device with the reference ultrasound image.

Example 46. The method of any combination of examples 25-45, wherein the reference ultrasound image comprises a motion picture covering a full-cycle of a moving anatomical structure.

Example 47. The method of example 46, wherein moving anatomical structure is a heart.

Example 48. The method of any combination of examples 25-47, further comprising identifying common anatomical structures in the reference ultrasound image and the live ultrasound image using image recognition prior to registering the reference ultrasound image and the live ultrasound image.

Example 49. A non-transitory computer-readable medium comprising instructions, which when executed, cause one or more processors to: generate a reference ultrasound image of a region of a patient based on a portion of received ultrasound energy that was received prior to a medical instrument or medical device causing obstruction in the received ultrasound energy; generate a live ultrasound image based on a current portion of the received ultrasound energy; register the reference ultrasound image and the live ultrasound image; and control a display device to display the reference ultrasound image with at least a portion of the live ultrasound image.

Example 50. The non-transitory computer-readable medium of example 49, wherein the instructions, when executed, further cause the one or more processors to: receive EM tracking data from an EM tracking system; determine at least one of a position, orientation or trajectory of the medical instrument or medical device based on the EM tracking data; and generate the representation of the medical instrument or medical device based on the determined position, orientation or trajectory.

Example 51. The non-transitory computer-readable medium of example 49 or 50, wherein the portion of the received ultrasound energy received by the ultrasound sensor prior to the medical instrument or medical device causing the obstruction was received when the medical instrument or medical device was at least partially positioned within the region of the patient.

Example 52. The non-transitory computer-readable medium of any combination of examples 49-51, wherein the portion of the received ultrasound energy received by the ultrasound sensor prior to the medical instrument or medical device causing the obstruction was received before the medical instrument or medical device was at least partially positioned within the region of the patient.

Example 53. The non-transitory computer-readable medium of any combination of examples 49-52, wherein the reference ultrasound image includes a plurality of reference ultrasound images, the non-transitory computer-readable medium further comprising receiving event data, selecting one of the reference ultrasound images based on correspondence with the event data, and controlling the display device to display the selected ultrasound image with the at least a portion of the live ultrasound image or the representation of the medical instrument or medical device.

Example 54. The non-transitory computer-readable medium of example 53, wherein the event data comprises cardiac event data.

Example 55. The non-transitory computer-readable medium of example 54, wherein the cardiac event data includes a phase of a cardiac cycle, and the selected reference ultrasound image corresponds to the phase of the cardiac cycle.

Example 56. The non-transitory computer-readable medium of example 55, wherein the instructions, when executed further cause the one or more processors to determine the phase of the cardiac cycle based on at least one of an ECG signal or the live ultrasound image.

Example 57. The non-transitory computer-readable medium of any combination of examples 49-56, wherein the reference ultrasound image includes a plurality of reference ultrasound images, and wherein the instructions, when executed, further cause the one or more processors to select one of the reference ultrasound images based on one of a plurality of spatial orientations of the live ultrasound image, and control the display device to display the at least a portion of the live ultrasound image with the selected reference ultrasound image.

Example 58. The non-transitory computer-readable medium of example 57, wherein each of the reference ultrasound images corresponds to one of the plurality of spatial orientations of the live ultrasound image, and wherein each of the spatial orientations includes at least one of a translation, rotation, or perspective of the live ultrasound image.

Example 59. The non-transitory computer-readable medium of any combination of examples 49-58, wherein the reference ultrasound image includes a plurality of reference ultrasound images, and wherein the instructions, when executed, further cause the one or more processors to receive event data, select one of the reference ultrasound images based on both the event data and one of a plurality of spatial orientations of the live ultrasound image, and control the display device to display the selected ultrasound image with the least a portion of the live ultrasound image.

Example 60. The non-transitory computer-readable medium of any combination of examples 49-59, wherein the medical instrument or medical device comprises at least one of an implantable medical device, medical implant delivery device, therapy delivery device, surgical device, mechanical circulatory support device, coronary stent device, heart valve device, heart valve repair device, cardiac ablation device, cardiac lead device, drug delivery device, catheter delivery device, or endoscopic delivery device.

Example 61. The non-transitory computer-readable medium of any combination of examples 49-60, wherein the medical instrument or medical device comprises an instrument configured for transcatheter heart valve repair or replacement.

Example 62. The non-transitory computer-readable medium of any combination of examples 49-61, wherein the medical instrument or medical device further comprises a prosthetic heart valve.

Example 63. The non-transitory computer-readable medium of example 62, wherein the prosthetic heart valve comprises a prosthetic mitral valve.

Example 64. The non-transitory computer-readable medium of any combination of examples 49-63, wherein the instructions, when executed, further cause the one or more processors to control the display device to display the reference ultrasound image with the representation of the medical instrument or medical device.

Example 65. The non-transitory computer-readable medium of any combination of examples 49-64, wherein the instructions, when executed, further cause the one or more processors to: identify a physiological landmark of the region of the patient based on the live ultrasound image; and register the reference ultrasound image with the physiological landmark.

Example 66. The non-transitory computer-readable medium of any combination of examples 49-65, wherein the instructions, when executed, further cause the one or more processors to control the display device to display the at least a portion of the live ultrasound image with the reference ultrasound image such that the reference ultrasound image moves in registration with the at least a portion of the live ultrasound image.

Example 67. The non-transitory computer-readable medium of any combination of examples 49-66, wherein the instructions, when executed, further cause the one or more processors to: determine that at least one of a position, orientation, or trajectory of the medical instrument or medical device has changed; and control the display device to display at least one of an updated position, orientation, or trajectory of the medical instrument or medical device based on the determination that at least one of the position, orientation, or trajectory has changed.

Example 68. The non-transitory computer-readable medium of any combination of examples 49-67, wherein the instructions, when executed, further cause the one or more processors to control the display device to display the reference ultrasound image with the representation of the medical instrument or medical device.

Example 69. The non-transitory computer-readable medium of any combination of examples 49-68, wherein the instructions, when executed, further cause the one or more processors to: collect EM tracking data representative of a position or orientation of each of the ultrasound sensor and the medical instrument or medical device relative to the region of the patient; receive the EM tracking data from the EM tracking system; determine at least one of a position, orientation, or trajectory of the medical instrument or medical device based on the EM tracking data; and control the display device to display at least one of the position, orientation, or trajectory of the medical instrument or medical device with the reference ultrasound image.

Example 70. The non-transitory computer-readable medium of any combination of examples 49-69, wherein the reference ultrasound image comprises a motion picture covering a full-cycle of a moving anatomical structure.

Example 71. The non-transitory computer-readable medium of example 70, wherein moving anatomical structure is a heart.

Example 72. The non-transitory computer-readable medium of any combination of examples 49-71, wherein the instructions, when executed, further cause the one or more processors to identify common anatomical structures in the reference ultrasound image and the live ultrasound image using image recognition prior to registering the reference ultrasound image and the live ultrasound image.

Example 73. A system comprising: an ultrasound transducer array; and one or more processors configured to: control the ultrasound transducer array to transmit first ultrasound energy in a first direction and transmit second ultrasound energy in a second direction substantially simultaneously, wherein the second direction is different than the first direction; control the ultrasound transducer array to receive first reflected ultrasound energy in a first field of view of a region of patient anatomy based at least in part on reflection of the first transmitted ultrasound energy and receive second reflected ultrasound energy in a second field of view of the region of patient anatomy based at least in part on reflection of the second transmitted ultrasound energy substantially simultaneously, wherein the second field of view is different than the first field of view; and generate one or more ultrasound images based on the first reflected ultrasound energy and the second reflected ultrasound energy.

Example 74. The system of example 73, wherein the one or more processors are configured to: control the ultrasound transducer array to transmit third ultrasound energy in a third direction different than the first and second directions and receive third reflected ultrasound energy in a third field of view of the region of patient anatomy based at least in part on reflection of the third ultrasound energy, wherein the third field of view is different than the first and second fields of view; detect an obstruction in the third ultrasound image data in the third field of view; and control the ultrasound transducer array to transmit the first and second ultrasound energy and receive the first and second reflected ultrasound energy based on detection of the obstruction in the third reflected ultrasound energy in the third field of view.

Example 75. The system of example 74, wherein the first ultrasound energy and the second ultrasound energy are higher in frequency than the third ultrasound energy.

Example 76. The system of example 74 or 75, wherein the one or more processors are configured to detect the obstruction in the third reflected ultrasound energy in the third field of view based on detection of obstruction by at least a portion of a medical instrument or medical device in the region of patient anatomy.

Example 77. The system of example 76, wherein the one or more processors are configured to detect the obstruction in the third reflected ultrasound energy based on at least one of one or more characteristics of the third reflected ultrasound energy received in the third field of view or one or more characteristics of an ultrasound image generated based on processing of the third reflected ultrasound energy received in the third field of view.

Example 78. The system of example 76 or 77, wherein the third field of view is selected to include at least a portion of the region of the patient anatomy in which the medical instrument or medical device is introduced.

Example 79. The system of any combination of examples 73-78, wherein the first field of view is selected to include a first portion of the region of the patient anatomy on a first side of a medical instrument or medical device when the medical instrument or medical device is introduced into the region of the patient anatomy and the second field of view is selected to include a second portion of the region of the patient anatomy on a second side of the medical instrument or medical device when the medical instrument or medical device is introduced into the region of the patient anatomy.

Example 80. The system of any combination of examples 73-79, wherein the first and second fields of view are selected to exclude at least a portion of the region of the patient anatomy in which the medical instrument or medical device is introduced.

Example 81. The system of any combination of examples 73-80, wherein the first and second fields of view are selected to exclude at least a portion of the region of the patient anatomy in which obstruction in received reflected ultrasound energy is caused by the medical instrument or medical device.

Example 82. The system of example 81, wherein the medical instrument or medical device comprises at least one of an implantable medical device, medical implant delivery device, therapy delivery device, surgical device, mechanical circulatory support device, coronary stent device, heart valve device, heart valve repair device, cardiac ablation device, cardiac lead device, drug delivery device, catheter delivery device, or endoscopic delivery device.

Example 83. The system of example 81 or 82, wherein the medical instrument or medical device comprises an instrument configured for transcatheter heart valve repair or replacement.

Example 84. The system of any combination of examples 81-83, wherein the medical instrument or medical device further comprises a prosthetic heart valve.

Example 85. The system of example 84, wherein the prosthetic heart valve comprises a prosthetic mitral valve.

Example 86. The system of any combination of examples 73-85, wherein the first and second fields of view are selected to exclude entirely a portion of the region of the patient anatomy in which obstruction in received reflected ultrasound energy is caused by at least one of the medical instrument or medical device.

Example 87. The system of any combination of examples 73-86, wherein the ultrasound transducer array comprises a one-dimensional array of ultrasound transducer elements.

Example 88. The system of any combination of examples 73-86, wherein the ultrasound transducer array comprises a two-dimensional array of ultrasound transducer elements.

Example 89. The system of any combination of examples 73-88, wherein the one or more processors are configured to control selected subsets of transducer elements in the ultrasonic transducer array to transmit the first and second ultrasound energy and receive the first and second reflected ultrasound energy.

Example 90. The system of any combination of examples 73-89, wherein the one or more processors are configured to control the ultrasound transducer array to transmit the first ultrasound energy in a first direction and transmit the second ultrasound energy in a second direction through beamforming.

Example 91. The system of any combination of examples 73-90, wherein the one or more processors are configured to control transducer elements in the ultrasonic transducer array to steer at least one of the first or second ultrasound energy transmitted by the ultrasonic transducer array and at least one of the first or second reflected ultrasound energy received by the ultrasonic transducer array in response to at least one of user input or automatic detection of an obstruction in at least one of the first or second reflected ultrasound energy received by the ultrasound transducer array.

Example 92. The system of any combination of examples 73-91, wherein the ultrasound transducer array comprises: a first ultrasound transducer array comprising a first plurality of ultrasound transducer elements, wherein the one or more processors are configured to control the first transducer array to transmit the first ultrasound energy in the first direction and to receive the first reflected ultrasound energy in the first field of view; and a second ultrasound transducer array, separate from the first ultrasound transducer array, comprising a second plurality of ultrasound transducer elements, wherein the one or more processors are configured to control the second transducer array to transmit the second ultrasound energy in the second direction and to receive the second reflected ultrasound energy in the second field of view.

Example 93. The system of 92, wherein the one or more processors are configured to control at least one of the first or second ultrasound transducer arrays to steer at least one of the first ultrasound energy or the second ultrasound energy in the first or second directions, respectively.

Example 94. The system of example 92, wherein the one or more processors are configured to automatically control at least one of the first ultrasound transducer array or the second ultrasound transducer array to steer at least one of the first or second ultrasound energy in the first or second directions in response to the detection of obstruction in one or both of the first reflected ultrasound energy or second reflected ultrasound energy by the introduction of the medical instrument or medical device into the patient anatomy.

Example 95. The system of example 94, wherein the one or more processors are further configured to automatically and dynamically control at least one of the first ultrasound transducer array or the second ultrasound transducer array to steer at least one of the first or second ultrasound energy in the first or second directions in response to the automatic detection of obstruction in one or both of the first reflected ultrasound energy or second reflected ultrasound energy by the movement of the medical instrument or medical device in the patient anatomy.

Example 96. The system of example 92, wherein the first ultrasound transducer array is spatially separated from the second ultrasound transducer array.

Example 97. The system of any combination of examples 73-96, wherein the first field of view and the second field of view overlap, and the one or more processors are configured to generate the one or more ultrasound images based on a combination of the first and second reflected ultrasound energy in the first field of view and the second field of view.

Example 98. The system of any combination of examples 73-97, wherein the first field of view and the second field of view do not overlap, and the one or more processors are configured to generate the one or more ultrasound images based on a combination of the first and second reflected ultrasound energy in the first field of view and the second field of view.

Example 99. The system of any combination of examples 73-98, wherein the one or more ultrasound images comprise a first ultrasound image and a separate second ultrasound image.

Example 100. The system of any combination of examples 73-99, further comprising a transesophageal ultrasound probe, wherein the ultrasound transducer array is carried within a portion of the transesophageal ultrasound probe.

Example 101. The system of any combination of examples 73-99, wherein the ultrasound transducer array is configured for use outside of a patient.

Example 102. The system of any combination of examples 73-100, wherein the ultrasound transducer array is configured for use inside a patient.

Example 103. The system of any combination of examples 73-102, wherein the one or more processors are configured to control a display device to display the one or more ultrasound images.

Example 104. The system of any combination of examples 73-103, further comprising a display device configured to display the one or more ultrasound images.

Example 105. The system of any combination of examples 73-104, wherein the at least one ultrasound image is a first ultrasound image, and wherein the one or more processors are configured to: generate a reference ultrasound image of the region of the patient anatomy based on reflected ultrasound energy that was received by the ultrasound transducer array prior to at the least one of a medical instrument or medical device causing obstruction in the reflected ultrasound energy; and control a display device to display at least a portion of the reference ultrasound image with at least a portion of the first ultrasound image.

Example 106. The system of example 105, wherein the one or more processors are configured to at least partially register the at least a portion of the reference ultrasound image and the at least a portion of the first ultrasound image.

Example 107. A method comprising: controlling an ultrasound transducer array to transmit first ultrasound energy in a first direction and transmit second ultrasound energy in a second direction substantially simultaneously, wherein the second direction is different than the first direction; controlling the ultrasound transducer array to receive first reflected ultrasound energy in a first field of view of a region of patient anatomy based at least in part on reflection of the first transmitted ultrasound energy and receive second reflected ultrasound energy in a second field of view of the region of patient anatomy based at least in part on reflection of the second transmitted ultrasound energy substantially simultaneously, wherein the second field of view is different than the first field of view; and generating one or more ultrasound images based on the first reflected ultrasound energy and the second reflected ultrasound energy.

Example 108. The method of example 107, further comprising: controlling the ultrasound transducer array to transmit third ultrasound energy in a third direction different than the first and second directions and receive third reflected ultrasound energy in a third field of view of the region of patient anatomy based at least in part on reflection of the third ultrasound energy, wherein the third field of view is different than the first and second fields of view; detecting an obstruction in the third ultrasound image data in the third field of view; and controlling the ultrasound transducer array to transmit the first and second ultrasound energy and receive the first and second reflected ultrasound energy based on detection of the obstruction in the third reflected ultrasound energy in the third field of view.

Example 109. The method of example 108, wherein the first ultrasound energy and the second ultrasound energy are higher in frequency than the third ultrasound energy.

Example 110. The method of any combination of examples 107-109, further comprising detecting the obstruction in the third reflected ultrasound energy in the third field of view based on detection of obstruction by at least a portion of at least one medical instrument or medical device in the region of patient anatomy.

Example 111. The method of example 110, further comprising detecting the obstruction in the third reflected ultrasound energy based on at least one of one or more characteristics of the third reflected ultrasound energy received in the third field of view or one or more characteristics of an ultrasound image generated based on processing of the third reflected ultrasound energy received in the third field of view.

Example 112. The method of example 110 or 111, wherein the third field of view is selected to include at least a portion of the region of the patient anatomy in which the medical instrument or medical device is introduced.

Example 113. The method of any combination of examples 107-112, wherein the first field of view is selected to include a first portion of the region of the patient anatomy on a first side of a medical instrument or medical device when the medical instrument or medical device is introduced into the region of the patient anatomy and the second field of view is selected to include a second portion of the region of the patient anatomy on a second side of the medical instrument or medical device when the medical instrument or medical device is introduced into the region of the patient anatomy.

Example 114. The method of any combination of examples 107-113, wherein the first and second fields of view are selected to exclude at least a portion of the region of the patient anatomy in which the at least one of the medical instrument or medical device is introduced.

Example 115. The method of any combination of examples 107-114, wherein the first and second fields of view are selected to exclude at least a portion of the region of the patient anatomy in which obstruction in received reflected ultrasound energy is caused by the medical instrument or medical device.

Example 116. The method of example 115, wherein the medical instrument or medical device comprises at least one of an implantable medical device, medical implant delivery device, therapy delivery device, surgical device, mechanical circulatory support device, coronary stent device, heart valve device, heart valve repair device, cardiac ablation device, cardiac lead device, drug delivery device, catheter delivery device, or endoscopic delivery device.

Example 117. The method of example 115, wherein the medical instrument or medical device comprises an instrument configured for transcatheter heart valve repair or replacement.

Example 118. The method of example 115, wherein the medical instrument or medical device further comprises a prosthetic heart valve.

Example 119. The method of example 118, wherein the prosthetic heart valve comprises a prosthetic mitral valve.

Example 120. The method of any combination of examples 107-119, wherein the first and second fields of view are selected to exclude entirely a portion of the region of the patient anatomy in which obstruction in received reflected ultrasound energy is caused by at least one of the medical instrument or medical device.

Example 121. The method of any combination of examples 107-120, wherein the ultrasound transducer array comprises a one-dimensional array of ultrasound transducer elements.

Example 122. The method of any combination of examples 107-120, wherein the ultrasound transducer array comprises a two-dimensional array of ultrasound transducer elements.

Example 123. The method of any combination of examples 107-122, further comprising controlling selected subsets of transducer elements in the ultrasonic transducer array to transmit the first and second ultrasound energy and receive the first and second reflected ultrasound energy.

Example 124. The method of any combination of examples 107-122, wherein the controlling the ultrasound transducer array to transmit the first ultrasound energy in a first direction and transmit the second ultrasound energy in a second direction is through beamforming.

Example 125. The method of any combination of examples 107-123, further comprising controlling transducer elements in the ultrasonic transducer array to steer at least one of the first or second ultrasound energy transmitted by the ultrasonic transducer array and at least one of the first or second reflected ultrasound energy received by the ultrasonic transducer array in response to at least one of user input or automatic detection of an obstruction in at least one of the first or second reflected ultrasound energy received by the ultrasound transducer array.

Example 126. The method of any combination of examples 107-125, wherein the ultrasound transducer array comprises: a first ultrasound transducer array comprising a first plurality of ultrasound transducer elements, wherein the one or more processors are configured to control the first transducer array to transmit the first ultrasound energy in the first direction and to receive the first reflected ultrasound energy in the first field of view; and a second ultrasound transducer array, separate from the first ultrasound transducer array, comprising a second plurality of ultrasound transducer elements, wherein the one or more processors are configured to control the second transducer array to transmit the second ultrasound energy in the second direction and to receive the second reflected ultrasound energy in the second field of view.

Example 127. The method of example 126, further comprising controlling at least one of the first or second ultrasound transducer arrays to steer at least one of the first ultrasound energy or the second ultrasound energy in the first or second directions, respectively.

Example 128. The method of example 126, further comprising automatically controlling at least one of the first ultrasound transducer array or the second ultrasound transducer array to steer at least one of the first or second ultrasound energy in the first or second directions in response to the detection of obstruction in one or both of the first reflected ultrasound energy or second reflected ultrasound energy by the introduction of the medical instrument or medical device into the patient anatomy.

Example 129. The method of example 126, further comprising automatically and dynamically controlling at least one of the first ultrasound transducer array or the second ultrasound transducer array to steer at least one of the first or second ultrasound energy in the first or second directions in response to the automatic detection of obstruction in one or both of the first reflected ultrasound energy or second reflected ultrasound energy by the movement of the medical instrument or medical device in the patient anatomy.

Example 130. The method of any combination of examples 126-129, wherein the first ultrasound transducer array is spatially separated from the second ultrasound transducer array.

Example 131. The method of any combination of examples 107-130, wherein the first field of view and the second field of view overlap, the method further comprising generating the one or more ultrasound images based on a combination of the first and second reflected ultrasound energy in the first field of view and the second field of view.

Example 132. The method of any combination of examples 107-131, wherein the first field of view and the second field of view do not overlap, the method further comprising generating the one or more ultrasound images based on a combination of the first and second reflected ultrasound energy in the first field of view and the second field of view.

Example 133. The method of any combination of examples 107-133, wherein the one or more ultrasound images comprise a first ultrasound image and a separate second ultrasound image.

Example 134. The method of any combination of examples 107-133, wherein the ultrasound transducer array is carried within a portion of a transesophageal ultrasound probe.

Example 135. The method of any combination of examples 107-132, wherein the ultrasound transducer array is configured for use outside of a patient.

Example 136. The method of any combination of examples 107-133, wherein the ultrasound transducer array is configured for use inside a patient.

Example 137. The method of any combination of examples 107-136, further comprising controlling a display device to display the ultrasound image.

Example 138. The method of any combination of examples 107-137, wherein the at least one ultrasound image is a first ultrasound image, the method further comprising: generating a reference ultrasound image of the region of the patient anatomy based on reflected ultrasound energy that was received by the ultrasound transducer array prior to at the least one of a medical instrument or medical device causing obstruction in the reflected ultrasound energy; and controlling a display device to display at least a portion of the reference ultrasound image with at least a portion of the first ultrasound image.

Example 139. The method of example 138, further comprising at least partially registering the at least a portion of the reference ultrasound image and the at least a portion of the first ultrasound image.

Example 140. A non-transitory computer-readable medium comprising instructions to cause one or more processors to: control an ultrasound transducer array to transmit first ultrasound energy in a first direction and transmit second ultrasound energy in a second direction substantially simultaneously, wherein the second direction is different than the first direction; control the ultrasound transducer array to receive first reflected ultrasound energy in a first field of view of a region of patient anatomy based at least in part on reflection of the first transmitted ultrasound energy and receive second reflected ultrasound energy in a second field of view of the region of patient anatomy based at least in part on reflection of the second transmitted ultrasound energy substantially simultaneously, wherein the second field of view is different than the first field of view; and generate one or more ultrasound images based on the first reflected ultrasound energy and the second reflected ultrasound energy.

Example 141. A system comprising: an ultrasound transducer array; and one or more processors configured to: control the ultrasound transducer array to transmit first ultrasound energy in a first direction; control the ultrasound transducer array to receive first reflected ultrasound energy in a first field of view of a region of patient anatomy based at least in part on reflection of the first transmitted ultrasound energy; control the ultrasound transducer array to cease transmitting first ultrasound energy in the first direction; control the ultrasound transducer array to transmit second ultrasound energy in a second direction; and control the ultrasound transducer array to receive second reflected ultrasound energy in a second field of view of the region of patient anatomy based at least in part on reflection of the second transmitted ultrasound energy, wherein the second field of view is of a different shape than the first field of view.

Example 142. The system of example 141, wherein the second field of view is generally trapezoidal in cross section and wider than the first field of view.

Example 143. The system of example 141, wherein the second field of view is generally toroidal in shape.

Example 144. The system of any combination of examples 141-143, wherein the one or more processors are further configured to detect an obstruction in the first reflected ultrasound energy in the first field of view or in an ultrasound image based on the first reflected ultrasound energy in the first field of view.

Example 145. The system of any combination of examples 141-144, wherein the one or more processors are further configured to send a notification to a clinician upon the detection of the obstruction via a notification device.

Example 146. The system of any combination of examples 141-145, wherein the one or more processors are further configured to transmit the second ultrasound energy upon detection of the obstruction in the first reflected ultrasound energy.

Example 147. The system of example 146, wherein the transmission of the second ultrasound energy upon the detection of the obstruction is automatic.

Example 148. A method comprising: controlling an ultrasound transducer array to transmit first ultrasound energy in a first direction; controlling the ultrasound transducer array to receive first reflected ultrasound energy in a first field of view of a region of patient anatomy based at least in part on reflection of the first transmitted ultrasound energy in a region of patient anatomy; controlling the ultrasound transducer array to cease transmitting first ultrasound energy in the first direction; controlling the ultrasound transducer array to transmit second ultrasound energy in a second direction; and controlling the ultrasound transducer array to receive second reflected ultrasound energy in a second field of view of the region of patient anatomy based at least in part on reflection of the second transmitted ultrasound energy, wherein the second field of view is of a different shape than the first field of view.

Example 149. The method of example 148, wherein the second field of view is generally trapezoidal in cross section.

Example 150. The method of example 148, wherein the second field of view is generally toroidal in shape.

Example 151. The method of any combination of examples 148-150, further comprising detecting an obstruction in the first reflected ultrasound energy in the first field of view or in an ultrasound image based on the first reflected ultrasound energy in the first field of view.

Example 152. The method of example 151, further comprising sending a notification to a clinician upon the detection of the obstruction via a notification device.

Example 153. The method of example 151, further comprising transmitting the second ultrasound energy upon detection of the obstruction in the first reflected ultrasound energy.

Example 154. The method of example 153, wherein the transmission of the second ultrasound energy upon the detection of the obstruction is automatic.

Example 155. A non-transitory computer-readable medium comprising instructions, that when executed, cause one or more processors to: control an ultrasound transducer array to transmit first ultrasound energy in a first direction; control the ultrasound transducer array to receive first reflected ultrasound energy in a first field of view of a region of patient anatomy based at least in part on reflection of the first transmitted ultrasound energy in a region of patient anatomy; control the ultrasound transducer array to cease transmitting the first ultrasound energy in the first direction; control the ultrasound transducer array to transmit second ultrasound energy in a second direction; and control the ultrasound transducer array to receive second reflected ultrasound energy in a second field of view of the region of patient anatomy based at least in part on reflection of the second transmitted ultrasound energy, wherein the second field of view is of a different shape than the first field of view.

Example 156. The non-transitory computer-readable medium of example 155, wherein the second field of view is generally trapezoidal in cross section.

Example 157. The non-transitory computer-readable medium of example 155, wherein the second field of view is generally toroidal in shape.

Example 158. The non-transitory computer-readable medium of any combination of examples 155-157, further comprising detecting an obstruction in the first reflected ultrasound energy in the first field of view or in an ultrasound image based on the first reflected ultrasound energy in the first field of view.

Example 159. The non-transitory computer-readable medium of example 158, further comprising sending a notification to a clinician upon the detection of the obstruction via a notification device.

Example 160. The non-transitory computer-readable medium of example 158, further comprising transmitting the second ultrasound energy upon detection of the obstruction in the first reflected ultrasound energy.

Example 161. The non-transitory computer-readable medium of example 160, wherein the transmission of the second ultrasound energy upon the detection of the obstruction is automatic.

Example 162. A system comprising: an ultrasound transducer array; and one or more processors configured to: control the ultrasound transducer array to transmit ultrasound energy in a direction; control the ultrasound transducer array to receive reflected ultrasound energy in a field of view of a region of patient anatomy based at least in part on reflection of the transmitted ultrasound energy; automatically detect an obstruction in the reflected ultrasound energy in the field of view; and control the ultrasound transducer array to automatically steer the transmitted ultrasound energy in a direction away from the obstruction based on detection of the obstruction in the reflected ultrasound energy in the field of view so as to change the field of view.

Example 163. The system of example 162, wherein the one or more processors are configured to detect the obstruction in the reflected ultrasound energy in the field of view based on detection of obstruction by at least a portion of a medical instrument or medical device in the region of patient anatomy.

Example 164. The system of example 162, wherein the one or more processors are configured to detect the obstruction in the reflected ultrasound energy based on at least one of one or more characteristics of the reflected ultrasound energy received in the field of view or one or more characteristics of an ultrasound image generated based on processing of the reflected ultrasound energy received in the field of view.

Example 165. The system of any combination of examples 162-164, wherein the one or more processors are further configured to dynamically control the ultrasound transducer array to steer the ultrasound energy away from the obstruction in response to the detection of the obstruction in the reflected ultrasound energy in the field of view as the medical instrument or medical device moves in the patient anatomy.

Example 166. The system of any combination of examples 162-165, wherein the one or more processors are further configured to generate an ultrasound image based on the reflected ultrasound energy.

Example 167. The system of any combination of examples 162-166, wherein the one or more processors are configured to control the ultrasound transducer array to automatically steer the transmitted ultrasound energy in a direction away from the obstruction by transmitting via split apertures ultrasound energy in a plurality of directions.

Example 168. The system of any combination of examples 162-167, wherein the one or more processors are configured to control the ultrasound transducer array to automatically steer the transmitted ultrasound energy in a direction away from the obstruction by widening the field of view and making the field of view more shallow.

Example 169. The system of example 162, wherein the one or more processors are configured to control the ultrasound transducer array to automatically steer the transmitted ultrasound energy in a direction away from the obstruction by transmitting in a toroidal mode.

Example 169.1. The system of any combination of examples 162-169, wherein the changed field of view is selected to avoid obstruction caused by the medical instrument or medical device.

Example 169.2. The system of any combination of examples 163-169.1, wherein the changed field of view excludes at least a portion of the medical instrument or medical device.

Example 170. A method comprising: controlling an ultrasound transducer array to transmit ultrasound energy in a direction; controlling the ultrasound transducer array to receive reflected ultrasound energy in a field of view of a region of patient anatomy based at least in part on reflection of the transmitted ultrasound energy in a region of patient anatomy; automatically detecting an obstruction in the reflected ultrasound energy in the field of view; and controlling the ultrasound transducer array to automatically steer the transmitted ultrasound energy in a direction away from the obstruction based on detection of the obstruction in the reflected ultrasound energy in the field of view so as to change the field of view.

Example 171. The method of example 170, wherein detecting the obstruction in the reflected ultrasound energy in the field of view is based on detection of obstruction by at least a portion of at least one medical instrument or medical device in the region of patient anatomy.

Example 172. The method of example 170, wherein detecting the obstruction in the reflected ultrasound energy is based on at least one of one or more characteristics of the reflected ultrasound energy received in the field of view or one or more characteristics of an ultrasound image generated based on processing of the reflected ultrasound energy received in the field of view.

Example 173. The method of any combination of examples 170-172, further comprising dynamically controlling the ultrasound transducer array to steer the ultrasound energy away from the obstruction in response to the detection of the obstruction in the reflected ultrasound energy in the field of view as the medical instrument or medical device moves in the patient anatomy.

Example 174. The method of any combination of examples 170-173, further comprising generating an ultrasound image based on the reflected ultrasound energy.

Example 175. The method of any combination of examples 170-174, wherein controlling the ultrasound transducer array to automatically steer the transmitted ultrasound energy in a direction away from the obstruction comprises transmitting via split apertures ultrasound energy in a plurality of directions.

Example 176. The method of any combination of examples 170-175, wherein controlling the ultrasound transducer array to automatically steer the transmitted ultrasound energy in a direction away from the obstruction comprises widening the field of view.

Example 177. The method of any combination of examples 170-176, wherein controlling the ultrasound transducer array to automatically steer the transmitted ultrasound energy in a direction away from the obstruction comprises transmitting in a toroidal mode.

Example 178. A non-transitory computer-readable medium comprising instructions, that when executed, cause one or more processors to: control an ultrasound transducer array to transmit ultrasound energy in a direction; control the ultrasound transducer array to receive reflected ultrasound energy in a field of view of a region of patient anatomy based at least in part on reflection of the transmitted ultrasound energy in a region of patient anatomy; automatically detect an obstruction in the reflected ultrasound energy in the field of view; and control the ultrasound transducer array to automatically steer the transmitted ultrasound energy in a direction away from the obstruction based on detection of the obstruction in the reflected ultrasound energy in the field of view so as to change the field of view.

Example 179. The non-transitory computer-readable medium of example 178, wherein detecting the obstruction in the reflected ultrasound energy in the field of view is based on detection of obstruction by at least a portion of at least one medical instrument or medical device in the region of patient anatomy.

Example 180. The non-transitory computer-readable medium of example 178, wherein detecting the obstruction in the reflected ultrasound energy is based on at least one of one or more characteristics of the reflected ultrasound energy received in the field of view or one or more characteristics of an ultrasound image generated based on processing of the reflected ultrasound energy received in the field of view.

Example 181. The non-transitory computer-readable medium of any combination of examples 178-180, further comprising instructions, that when executed, cause one or more processors to dynamically control the ultrasound transducer array to steer the ultrasound energy away from the obstruction in response to the detection of the obstruction in the reflected ultrasound energy in the field of view as the medical instrument or medical device moves in the patient anatomy.

Example 182. The non-transitory computer-readable medium of any combination of examples 178-181, further comprising instructions, that when executed, cause one or more processors to generate an ultrasound image based on the reflected ultrasound energy.

Example 183. The non-transitory computer-readable medium of any combination of examples 178-182, wherein the controlling the ultrasound transducer array to automatically steer the transmitted ultrasound energy in a direction away from the obstruction comprises transmitting via split apertures ultrasound energy in a plurality of directions.

Example 184. The non-transitory computer-readable medium of any combination of examples 178-183, wherein the controlling the ultrasound transducer array to automatically steer the transmitted ultrasound energy in a direction away from the obstruction comprises widening the field of view.

Example 185. The non-transitory computer-readable medium of any combination of examples 178-184, wherein the controlling the ultrasound transducer array to automatically steer the transmitted ultrasound energy in a direction away from the obstruction comprises transmitting in a toroidal mode.

Example 186. A system comprising: an ultrasound sensor configured to transmit ultrasound energy and receive ultrasound energy reflected in a region of a patient; and one or more processors configured to: generate a reference ultrasound image of the region of the patient based on a portion of the ultrasound energy that was received by the ultrasound sensor prior to a medical instrument or medical device causing obstruction in the received ultrasound energy; generate a live ultrasound image based on a current portion of the received ultrasound energy obtained by the ultrasound sensor; control a display device to display the live ultrasound image; automatically detect the obstruction; and upon detecting the obstruction, automatically control the display device to display the reference ultrasound image with the live ultrasound image.

Example 187. The system of example 186, wherein the one or more processors are further configured to automatically register the reference ultrasound image and the live ultrasound image.

Example 188. The system of example 187, wherein the one or more processors are further configured to control the display device to display the reference ultrasound image overlaid, underlaid or merged with the live ultrasound image.

Example 189. A method comprising: transmitting ultrasound energy; receiving ultrasound energy reflected in a region of a patient; generating a reference ultrasound image of the region of the patient based on a portion of the received ultrasound energy that was received prior to a medical instrument or medical device causing obstruction in the received ultrasound energy; generating a live ultrasound image based on a current portion of the received ultrasound energy; automatically detecting the obstruction; and upon detecting the obstruction, automatically controlling the display device to display the reference ultrasound image with the live ultrasound image.

Example 190. The method of example 189, further comprising automatically registering the reference ultrasound image and the live ultrasound image.

Example 191. The method of example 190, further comprising controlling the display device to display the reference ultrasound image overlaid, underlaid or merged with the live ultrasound image.

Example 192. A non-transitory computer-readable medium comprising instructions, which when executed, cause one or more processors to: generate a reference ultrasound image of a region of the patient based on a portion of ultrasound energy that was received by an ultrasound sensor prior to a medical instrument or medical device causing obstruction in the received ultrasound energy; generate a live ultrasound image based on a current portion of the received ultrasound energy obtained by the ultrasound sensor; control a display device to display the live ultrasound image; automatically detect the obstruction; and upon detecting the obstruction, automatically control the display device to display the reference ultrasound image with the live ultrasound image.

Example 193. The non-transitory computer-readable medium of example 192, wherein the instructions, when executed, automatically register the reference ultrasound image and the live ultrasound image.

Example 194. The non-transitory computer-readable medium of example 193, wherein the instructions, when executed, control the display device to display the reference ultrasound image overlaid, underlaid or merged with the live ultrasound image.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The terms "controller", "processor", or "processing circuitry" may generally refer to any of the foregoing logic circuitry, alone or in combination with other logic circuitry, or any other equivalent circuitry. A control unit comprising hardware may also perform one or more of the techniques of this disclosure. Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), or electronically erasable programmable read only memory (EEPROM), or other computer readable media.

Various examples have been described. These and other examples are within the scope of the following claims.

What is claimed is:

1. A system comprising:
an ultrasound transducer array; and
one or more processors configured to:
control the ultrasound transducer array to transmit third ultrasound energy in a third direction different than a first direction and a second direction and receive third reflected ultrasound energy in a third field of view of a region of patient anatomy based at least in part on reflection of the third ultrasound energy;
detect an obstruction in the third reflected ultrasound energy in the third field of view;
control, based on detecting the obstruction in the third reflected ultrasound energy, the ultrasound transducer array to transmit first ultrasound energy in the first direction and transmit second ultrasound energy in the second direction at a same time and to cease transmitting the third ultrasound energy in the third direction, wherein the second direction is different than the first direction;
control the ultrasound transducer array to receive first reflected ultrasound energy in a first field of view of a region of patient anatomy based at least in part on reflection of the first transmitted ultrasound energy and receive second reflected ultrasound energy in a second field of view of the region of patient anatomy based at least in part on reflection of the second transmitted ultrasound energy, wherein the second field of view is different than the first field of view; and
generate one or more ultrasound images based on the first reflected ultrasound energy and the second reflected ultrasound energy.

2. The system of claim 1, wherein the first ultrasound energy and the second ultrasound energy are higher in frequency than the third ultrasound energy.

3. The system of claim 1, wherein the one or more processors are configured to detect the obstruction in the third reflected ultrasound energy in the third field of view based on detection of obstruction by at least a portion of a medical instrument or medical device in the region of patient anatomy.

4. The system of claim 3, wherein the one or more processors are configured to detect the obstruction in the third reflected ultrasound energy based on at least one of one or more characteristics of the third reflected ultrasound energy received in the third field of view or one or more characteristics of an ultrasound image generated based on processing of the third reflected ultrasound energy received in the third field of view.

5. The system of claim 3, wherein the third field of view is selected to include at least a portion of the region of the patient anatomy in which the medical instrument or medical device is introduced.

6. The system of claim 1, wherein the first field of view is selected to include a first portion of the region of the patient anatomy on a first side of a medical instrument or medical device when the medical instrument or medical device is introduced into the region of the patient anatomy and the second field of view is selected to include a second portion of the region of the patient anatomy on a second side of the medical instrument or medical device when the medical instrument or medical device is introduced into the region of the patient anatomy.

7. The system of claim 1, wherein the first and second fields of view are selected to exclude at least a portion of the region of the patient anatomy in which a medical instrument or medical device is introduced.

8. The system of claim 1, wherein the first and second fields of view are selected to exclude at least a portion of the region of the patient anatomy in which obstruction in received reflected ultrasound energy is caused by a medical instrument or medical device such that the first and second fields of view do not include any obstruction.

9. The system of claim 8, wherein the medical instrument or medical device comprises at least one of an implantable medical device, medical implant delivery device, therapy delivery device, surgical device, mechanical circulatory support device, coronary stent device, heart valve device, heart valve repair device, cardiac ablation device, cardiac lead device, drug delivery device, catheter delivery device, or endoscopic delivery device.

10. The system of claim 8, wherein the medical instrument or medical device comprises an instrument configured for transcatheter heart valve repair or replacement.

11. The system of claim 8, wherein the medical instrument or medical device further comprises a prosthetic heart valve.

12. The system of claim 11, wherein the prosthetic heart valve comprises a prosthetic mitral valve.

13. The system of claim 1, wherein the first and second fields of view are selected to exclude an entirety of a portion of the region of the patient anatomy in which obstruction in received reflected ultrasound energy is caused by at least one of a medical instrument or medical device.

14. The system of claim 1, wherein the ultrasound transducer array comprises a one-dimensional array of ultrasound transducer elements.

15. The system of claim 1, wherein the ultrasound transducer array comprises a two-dimensional array of ultrasound transducer elements.

16. The system of claim 1, wherein the one or more processors are configured to control selected subsets of transducer elements in the ultrasound transducer array to transmit the first and second ultrasound energy and receive the first and second reflected ultrasound energy.

17. The system of claim 1, wherein the one or more processors are configured to control the ultrasound transducer array to transmit the first ultrasound energy in a first direction and transmit the second ultrasound energy in a second direction through beamforming.

18. The system of claim 1, wherein the one or more processors are configured to control transducer elements in the ultrasound transducer array to steer at least one of the first and second ultrasound energy transmitted by the ultrasonic transducer array and at least one of the first and second reflected ultrasound energy received by the ultrasonic transducer array in response to at least one of user input or automatic detection of an obstruction in at least one of the first or second reflected ultrasound energy received by the ultrasound transducer array.

19. The system of claim 1, wherein the ultrasound transducer array comprises:

a first ultrasound transducer array comprising a first plurality of ultrasound transducer elements, wherein the one or more processors are configured to control a first transducer array to transmit the first ultrasound energy in the first direction and to receive the first reflected ultrasound energy in the first field of view; and a second ultrasound transducer array, separate from the first ultrasound transducer array, comprising a second plurality of ultrasound transducer elements, wherein the one or more processors are configured to control a second transducer array to transmit the second ultrasound energy in the second direction and to receive the second reflected ultrasound energy in the second field of view.

20. The system of claim 19, wherein the one or more processors are configured to control at least one of the first and second ultrasound transducer arrays to steer at least one of the first ultrasound energy and the second ultrasound energy in the first and second directions.

21. The system of claim 19, wherein the one or more processors are configured to automatically control at least one of the first ultrasound transducer array and the second ultrasound transducer array to steer at least one of the first and second ultrasound energy in the first and second directions in response to the detection of obstruction in one or both of the first reflected ultrasound energy or second reflected ultrasound energy by introduction of a medical instrument or medical device into the patient anatomy.

22. The system of claim 19, wherein the one or more processors are further configured to automatically and dynamically control at least one of the first ultrasound transducer array and the second ultrasound transducer array to steer at least one of the first and second ultrasound energy in the first and second directions in response to the automatic detection of obstruction in one or both of the first reflected ultrasound energy or second reflected ultrasound energy by movement of a medical instrument or medical device in the patient anatomy.

23. The system of claim 19, wherein the first ultrasound transducer array is spatially separated from the second ultrasound transducer array.

24. The system of claim 1, wherein the first field of view and the second field of view overlap, and the one or more processors are configured to generate the one or more ultrasound images based on a combination of the first and second reflected ultrasound energy in the first field of view and the second field of view.

25. The system of claim 1, wherein the first field of view and the second field of view do not overlap, and the one or more processors are configured to generate the one or more ultrasound images based on a combination of the first and second reflected ultrasound energy in the first field of view and the second field of view.

26. The system of claim 1, wherein the one or more ultrasound images comprise a first ultrasound image and a separate second ultrasound image.

27. The system of claim 1, further comprising a transesophageal ultrasound probe, wherein the ultrasound transducer array is carried within a portion of the transesophageal ultrasound probe.

28. The system of claim 1, wherein the ultrasound transducer array is configured for use outside of a patient.

29. The system of claim 1, wherein the ultrasound transducer array is configured for use inside a patient.

30. The system of claim 1, wherein the one or more processors are configured to control a display device to display the one or more ultrasound images.

31. The system of claim 1, further comprising a display device configured to display the one or more ultrasound images.

32. The system of claim 1, wherein the one or more ultrasound images comprise a first ultrasound image, and wherein the one or more processors are configured to:

generate a reference ultrasound image of the region of the patient anatomy based on reflected ultrasound energy that was received by the ultrasound transducer array prior to at the least one of a medical instrument or medical device causing obstruction in the reflected ultrasound energy; and control a display device to display at least a portion of the reference ultrasound image with at least a portion of the first ultrasound image.

33. The system of claim 32, wherein the one or more processors are configured to at least partially register the at least a portion of the reference ultrasound image and the at least a portion of the first ultrasound image.

34. A method comprising:

controlling an ultrasound transducer array to transmit third ultrasound energy in a third direction different than a first direction and a second direction and receive third reflected ultrasound energy in a third field of view of a region of patient anatomy based at least in part on reflection of the third ultrasound energy;

detect an obstruction in the third reflected ultrasound energy in the third field of view;

controlling, based on detecting the obstruction in the third reflected ultrasound energy, the ultrasound transducer array to transmit first ultrasound energy in the first direction and transmit second ultrasound energy in the second direction at a same time and to cease transmitting the third ultrasound energy in the third direction, wherein the second direction is different than the first direction;

controlling the ultrasound transducer array to receive first reflected ultrasound energy in a first field of view of a region of patient anatomy based at least in part on reflection of the first transmitted ultrasound energy and receive second reflected ultrasound energy in a second field of view of the region of patient anatomy based at least in part on reflection of the second transmitted ultrasound energy, wherein the second field of view is different than the first field of view; and generating one or more ultrasound images based on the first reflected ultrasound energy and the second reflected ultrasound energy.

35. The method of claim 34, wherein the first ultrasound energy and the second ultrasound energy are higher in frequency than the third ultrasound energy.

36. The method of claim 34, further comprising detecting the obstruction in the third reflected ultrasound energy in the third field of view based on detection of obstruction by at least a portion of at least one medical instrument or medical device in the region of patient anatomy.

37. The method of claim 36, further comprising detecting the obstruction in the third reflected ultrasound energy based on at least one of one or more characteristics of the third reflected ultrasound energy received in the third field of view or one or more characteristics of an ultrasound image generated based on processing of the third reflected ultrasound energy received in the third field of view.

38. The method of claim 36, wherein the third field of view is selected to include at least a portion of the region of the patient anatomy in which the medical instrument or medical device is introduced.

39. The method of claim 34, wherein the first field of view is selected to include a first portion of the region of the patient anatomy on a first side of a medical instrument or medical device when the medical instrument or medical device is introduced into the region of the patient anatomy and the second field of view is selected to include a second portion of the region of the patient anatomy on a second side of the medical instrument or medical device when the medical instrument or medical device is introduced into the region of the patient anatomy.

40. The method of claim 34, wherein the first and second fields of view are selected to exclude at least a portion of the region of the patient anatomy in which at least one of a medical instrument or medical device is introduced.

41. The method of claim 34, wherein the first and second fields of view are selected to exclude at least a portion of the region of the patient anatomy in which obstruction in received reflected ultrasound energy is caused by a medical instrument or medical device such that the first and second fields of view do not include any obstruction.

42. The method of claim 41, wherein the medical instrument or medical device comprises at least one of an implantable medical device, medical implant delivery device, therapy delivery device, surgical device, mechanical circulatory support device, coronary stent device, heart valve device, heart valve repair device, cardiac ablation device, cardiac lead device, drug delivery device, catheter delivery device, or endoscopic delivery device.

43. The method of claim 41, wherein the medical instrument or medical device comprises an instrument configured for transcatheter heart valve repair or replacement.

44. The method of claim 41, wherein the medical instrument or medical device further comprises a prosthetic heart valve.

45. The method of claim 44, wherein the prosthetic heart valve comprises a prosthetic mitral valve.

46. The method of claim 34, wherein the first and second fields of view are selected to exclude an entirety of a portion of the region of the patient anatomy in which obstruction in received reflected ultrasound energy is caused by at least one of a medical instrument or medical device.

47. The method of claim 34, wherein the ultrasound transducer array comprises a one-dimensional array of ultrasound transducer elements.

48. The method of claim 34, wherein the ultrasound transducer array comprises a two-dimensional array of ultrasound transducer elements.

49. The method of claim 34, further comprising controlling selected subsets of transducer elements in the ultrasound transducer array to transmit the first and second ultrasound energy and receive the first and second reflected ultrasound energy.

50. The method of claim 34, wherein the controlling the ultrasound transducer array to transmit the first ultrasound energy in a first direction and transmit the second ultrasound energy in a second direction is through beamforming.

51. The method of claim 34, further comprising controlling transducer elements in the ultrasound transducer array to steer at least one of the first and second ultrasound energy transmitted by the ultrasonic transducer array and at least one of the first and second reflected ultrasound energy received by the ultrasonic transducer array in response to at least one of user input or automatic detection of an obstruction in at least one of the first or second reflected ultrasound energy received by the ultrasound transducer array.

52. The method of claim 34, wherein the ultrasound transducer array comprises:

a first ultrasound transducer array comprising a first plurality of ultrasound transducer elements, wherein one or more processors are configured to control the first transducer array to transmit the first ultrasound energy in the first direction and to receive the first reflected ultrasound energy in the first field of view; and a second ultrasound transducer array, separate from the first ultrasound transducer array, comprising a second plurality of ultrasound transducer elements, wherein the one or more processors are configured to control the second transducer array to transmit the second ultrasound energy in the second direction and to receive the second reflected ultrasound energy in the second field of view.

53. The method of claim 52, further comprising controlling at least one of the first and second ultrasound transducer arrays to steer at least one of the first ultrasound energy and the second ultrasound energy in the first and second directions.

54. The method of claim 52, further comprising automatically controlling at least one of the first ultrasound transducer array and the second ultrasound transducer array to steer at least one of the first and second ultrasound energy in the first and second directions in response to the detection of obstruction in one or both of the first reflected ultrasound energy or second reflected ultrasound energy by introduction of a medical instrument or medical device into the patient anatomy.

55. The method of claim 52, further comprising automatically and dynamically controlling at least one of the first ultrasound transducer array and the second ultrasound transducer array to steer at least one of the first and second ultrasound energy in the first and second directions in response to the automatic detection of obstruction in one or both of the first reflected ultrasound energy or second reflected ultrasound energy by movement of a medical instrument or medical device in the patient anatomy.

56. The method of claim 52, wherein the first ultrasound transducer array is spatially separated from the second ultrasound transducer array.

57. The method of claim 34, wherein the first field of view and the second field of view overlap, the method further comprising generating the one or more ultrasound images based on a combination of the first and second reflected ultrasound energy in the first field of view and the second field of view.

58. The method of claim 34, wherein the first field of view and the second field of view do not overlap, the method further comprising generating the one or more ultrasound images based on a combination of the first and second reflected ultrasound energy in the first field of view and the second field of view.

59. The method of claim 34, wherein the one or more ultrasound images comprise a first ultrasound image and a separate second ultrasound image.

60. The method of claim 34, wherein the ultrasound transducer array is carried within a portion of a transesophageal ultrasound probe.

61. The method of claim 34, wherein the ultrasound transducer array is configured for use outside of a patient.

62. The method of claim 34, wherein the ultrasound transducer array is configured for use inside a patient.

63. The method of claim 34, further comprising controlling a display device to display the ultrasound image.

64. The method of claim 34, wherein the one or more ultrasound images comprise a first ultrasound image, the method further comprising:

generating a reference ultrasound image of the region of the patient anatomy based on reflected ultrasound energy that was received by the ultrasound transducer array prior to at the least one of a medical instrument or medical device causing obstruction in the reflected ultrasound energy; and controlling a display device to display at least a portion of the reference ultrasound image with at least a portion of the first ultrasound image.

65. The method of claim 64, further comprising at least partially registering the at least a portion of the reference ultrasound image and the at least a portion of the first ultrasound image.

66. Non-transitory computer-readable media comprising instructions to cause one or more processors to:

control an ultrasound transducer array to transmit third ultrasound energy in a third direction different than a first direction and a second direction and receive third reflected ultrasound energy in a third field of view of a region of patient anatomy based at least in part on reflection of the third ultrasound energy;

detect an obstruction in the third reflected ultrasound energy in the third field of view;

control, based on detecting the obstruction in the third reflected ultrasound energy, an ultrasound transducer array to transmit first ultrasound energy in the first direction and transmit second ultrasound energy in the second direction at a same time and to cease transmitting the third ultrasound energy in the third direction, wherein the second direction is different than the first direction;

control the ultrasound transducer array to receive first reflected ultrasound energy in a first field of view of a region of patient anatomy based at least in part on reflection of the first transmitted ultrasound energy and receive second reflected ultrasound energy in a second field of view of the region of patient anatomy based at least in part on reflection of the second transmitted ultrasound energy, wherein the second field of view is different than the first field of view; and generate one or more ultrasound images based on the first reflected ultrasound energy and the second reflected ultrasound energy.

* * * * *